United States Patent
Plant et al.

(10) Patent No.: US 7,179,806 B2
(45) Date of Patent: *Feb. 20, 2007

(54) Δ1-PYRROLINES USED AS PESTICIDES

(75) Inventors: Andrew Plant, Winnersh (GB);
Thomas Seitz, Langenfeld (DE);
Johannes Rudolf Jansen, Monheim (DE); Christoph Erdelen, Leichlingen (DE); Andreas Turberg, Haan (DE); Olaf Hansen, Leichlingen (DE)

(73) Assignee: Bayer Cropscience AG, Monheim (DE)

( * ) Notice: Subject to any disclaimer, the term of this patent is extended or adjusted under 35 U.S.C. 154(b) by 317 days.

This patent is subject to a terminal disclaimer.

(21) Appl. No.: 10/433,443

(22) PCT Filed: Nov. 22, 2001

(86) PCT No.: PCT/EP01/13585

§ 371 (c)(1),
(2), (4) Date: Nov. 10, 2003

(87) PCT Pub. No.: WO02/46151

PCT Pub. Date: Jun. 13, 2002

(65) Prior Publication Data

US 2004/0082586 A1    Apr. 29, 2004

(30) Foreign Application Priority Data

Dec. 5, 2000    (DE) ............... 100 60 412

(51) Int. Cl.
C07D 207/20 (2006.01)
C07D 401/10 (2006.01)
C07D 403/10 (2006.01)
A01N 43/36 (2006.01)
C07D 239/42 (2006.01)

(52) U.S. Cl. ............... 514/235.8; 514/236.5; 514/237.2; 514/252.05; 514/252.19; 514/256; 514/274; 514/275; 514/343; 544/114; 544/122; 544/124; 544/238; 544/315; 544/331; 544/333; 546/276.4

(58) Field of Classification Search ............... 544/114, 544/122, 124, 238, 315, 331, 333; 546/276.4; 514/235.8, 256, 236.5, 274, 237.2, 275, 252.05, 514/343, 252.19; 548/565

See application file for complete search history.

(56) References Cited

U.S. PATENT DOCUMENTS

| 7,074,785 | B2 | 7/2006 | Seitz et al. | ............... 514/235.5 |
| 2005/0014650 | A1 | 1/2005 | Seitz et al. | ............... 504/283 |
| 2006/0142369 | A1 | 6/2006 | Seitz et al. | ............... 514/408 |

FOREIGN PATENT DOCUMENTS

| DE | 198 22 245 | 11/1999 |
| DE | 198 22 247 | 11/1999 |
| DE | 198 47 076 | 4/2000 |
| WO | 94/29268 | 12/1994 |
| WO | 98/22438 | 5/1998 |
| WO | 03/040092 A2 | 5/2003 |
| WO | 03/040132 A1 | 5/2003 |

OTHER PUBLICATIONS

Tetrahedron Letters, vol. 38, No. 22, (month unavailable) 1997, pp. 3841-3844, A. Giroux et al "One Pot Biaryl Synthesis *via in situ* Boronate Formation".
Aust. J. Chem, vol. 17 (month unavailable) 1964, pp. 794-802, D. J. Brown et al, "Pyrimidine Reactions VI. The Amination of Chloropyrimidines with n-Alkylamines".
Chem. Ber., (month unavailable) 1992, 125, pp. 1169-1190, C. Bolm et al, "Enantioselective Synthesis of Optically Active Pyridine Derivatives and $C_2$-Symmetric 2,2'-Bipyridines".
Chem. Pharm. Bull, 43(2) Feb. 1995, pp. 247-255, T. Seki et al, "Studies of Agents with Vasodilator and β-Blocking Activities. II[1]".
Eur. J. Med. Chem. 24, (month unavailable) 1989, pp. 249-258, Robert J. Ife et al, "Non-basic histamine $H_1$-antagonists. I. Synthesis and biological evaluation of some substituted 2-(2-pyridylaminoalkylamino) pyrimidones and related compounds".
J. Chem. Soc. (C) (month unavailable) 1971, pp. 1889-1891, B. W. Arantz et al, "Pyrimidine Reactions. Part XXII.[1] The Relative Reactivities of Some Corresponding Chloro-, Bromo-, and Iodo-pyrimidines in Aminolysis".
J. Chem. Soc. Perkin Trans., 1, (month unavailable) 1995, pp. 2497-2502, K. Matsumoto et al, "$Ag^+$Ion-selective lariat ethers: high pressure syntheses and cation recognition properties".
J. Med. Chem., 34, (month unavailable) 1991, pp. 315-319, W. Tjarks et al, "Boron-Containing Thiouracil Derivatives for Neutron-Capture Therapy of Melanoma".
J. Org. Chem., 49, (month unavailable) 1984, pp. 2240-2245, D. L. Boger et al, "Intramolecular Diels-Alfer Reactions of 1,2-Diazones: General Indoline Synthesis. Studies on the Preparation of the Central and Right-Hand Segments of CC-1065".
J. Org. Chem., 55, (month unavailable) 1990, pp. 69-73, D. L. Comins et al, "Lithiation of Methoxypyridines Directed by α-Amino Alkoxides".

(Continued)

Primary Examiner—Deepak Rao
(74) Attorney, Agent, or Firm—Richard E. L. Henderson

(57) ABSTRACT

The invention relates to novel $\Delta^1$-pyrrolines of the formula (I)

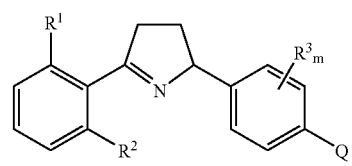

in which $R^1$, $R^2$, $R^3$, m, and Q have the meanings given in the disclosure, to a plurality of processes for preparing these substances, and to their use for controlling pests.

23 Claims, No Drawings

OTHER PUBLICATIONS

Organic Preparations and Procedures Int., 30(4), (month unavailable) 1998, H. Wojtowicz-Rajchel et al, "Facile Synthesis of 5-(Dihydroxyboryl)-2,4-*bis*(Alkoxy)Pyrimidines and N(1)-Substituted 5-(dihydroxyboryl)uracils".

Synthesis; No. 7, (month unavailable) 1999, pp. 1163-1168, I. Parrot et al, "Synthesis of Substituted 3-Amino-6-arylpyridazines via Suzuki Reaction".

Tetrahedron Letters 40 (month unavailable) 1999, pp. 7975-7978, I. Parrot et al, "Resin-bound thiophenols as $S_NAR$-labile linkers: application to the solid phase synthesis of aminopyridazines".

Tetrahedron Letters, vol. 37, No. 26, (month unavailable) 1996, pp. 4447-4450, C. Z. Ding et al, "Synthesis of 4-(N-Alkyl-N-Heteroaryl)amino-3,4-Dihydro-3-Hydroxy-2,2-Dimethyl-2H-1-Benzopyran-6-Carbonitrile Derivatives via an Unusual 1,4-Oxygen to Nitrogen Heteroaryl Migration".

Tetrahedron Letters, 41, (month unavailable) 2000, pp. 4335-4338, X. Wang et al, "Selective monolithiation of 2,5-dibromopyridine with butyllithium".

J. Org. Chem., 60 (month unavailable) 1995, pp. 7508-7510, T. Ishiyama et al, "Palladium(o)-Catalyzed Cross-Coupling Reaction of Alkoxydiboron with Haloarenes: A Direct Procedure for Arylboronic Esters".

Tetrahedron Letters, vol. 38, No. 19, (month unavailable) 1997, pp. 3477-3478, H. Zhang et al, "A Suite of Odd and Even Carbon-Numbered Spiroacetals in *Bactrocera latifrons*. Synthesis and Stereochemistry".

Chem. Ind., 37, (month unavailable) 1985, pp. 730-732, H. R. Ungerer, "Schiffsfarben—eine Spezialität der seenahen Lackindustrie".

Δ1-PYRROLINES USED AS PESTICIDES

This application is a 371 of PCT/EP01/13585 filed Nov. 22, 2001.

The present invention relates to novel $\Delta^1$-pyrrolines, to a plurality of processes for their preparation and to their use as pesticides.

It is already known that numerous $\Delta^1$-pyrrolines have insecticidal properties (cf. WO 00/21958, WO 99/59968, WO 99/59967 and WO 98/22438). The activity of these substances is good; however, in some cases it is unsatisfactory.

This invention now provides novel $\Delta^1$-pyrrolines of the formula (I)

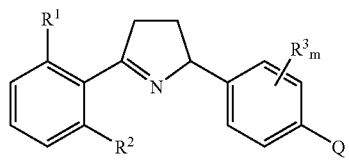

in which
$R^1$ represents halogen or methyl,
$R^2$ represents hydrogen or halogen,
$R^3$ represents halogen, represents in each case optionally substituted alkyl, alkoxy or alkylthio,
m represents 0, 1, 2, 3 or 4,
Q represents one of the groupings below

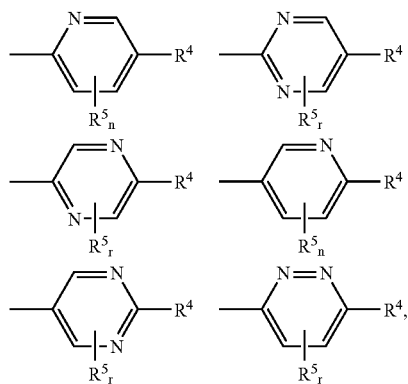

$R^4$ represents hydrogen, halogen, cyano, formyl, nitro, trialkylsilyl; represents in each case optionally substituted alkyl, alkenyl, alkoxy, alkenyloxy; represents pentafluorothio, —S(O)$_p$R$^6$, —NR$^7$R$^8$, —COR$^6$, —CO$_2$R$^6$, —CONR$^9$R$^{10}$, —N(R$^{11}$)COR$^{12}$ or —C(R$^3$)=N—OR$^{14}$; or represents in each case optionally substituted cycloalkyl, cycloalkylalkyl, aryl, arylalkyl, saturated or unsaturated heterocyclyl or heterocyclylalkyl,
$R^4$ furthermore represents —CH=NOH, formyl; represents in each case optionally substituted cycloalkyloxy or cycloalkylalkoxy,
$R^5$ represents halogen, cyano, formyl, nitro, trialkylsilyl; represents in each case optionally substituted alkyl, alkenyl, alkoxy, alkenyloxy; represents pentafluorothio, —S(O)$_p$R$^6$, —NR$^7$R$^8$, —COR$^6$, —CO$_2$R$^6$, —CONR$^9$R$^{10}$, —N(R$^{11}$)COR$^{12}$ or —C(R$^{13}$)=N—OR$^{14}$; or represents in each case optionally substituted cycloalkyl, cycloalkylalkyl, aryl, arylalkyl, saturated or unsaturated heterocyclyl or heterocyclylalkyl,
p represents 0, 1 or 2,
n represents 0, 1, 2 or 3, where the substituents $R^5$ can be identical or different if n represents 2 or 3,
r represents 0, 1 or 2, where the substituents $R^5$ can be identical or different if r represents 2,
$R^6$ represents in each case optionally substituted alkyl, cycloalkyl, aryl or arylalkyl,
$R^7$ and $R^8$ independently of one another represent hydrogen, —SO$_2$R$^6$, —COR$^6$, —CO$_2$R$^6$, represent in each case optionally substituted alkyl, alkenyl, cycloalkyl, cycloalkylalkyl, aryl, arylalkyl, saturated or unsaturated heterocyclyl or heterocyclylalkyl,
$R^7$ and $R^8$ furthermore together represent in each case optionally substituted alkenylene or alkylene, where the alkylene chain may in each case be interrupted by —O—, —S— or —NR$^{15}$—;
$R^7$ and $R^8$ furthermore together represent in each case optionally substituted alkylene, where the alkylene chain is interrupted either by C=O or by C=NO-alkyl,
$R^9$ and $R^{10}$ independently of one another represent hydrogen, —SO$_2$R$^6$, represent in each case optionally substituted alkyl, alkenyl, cycloalkyl, cycloalkylalkyl, aryl, arylalkyl, saturated or unsaturated heterocyclyl or heterocyclylalkyl,
$R^9$ and $R^{10}$ furthermore together represent optionally substituted alkylene, where the alkylene chain may in each case be interrupted by —O—, —S— or —NR$^{15}$—,
$R^{11}$ and $R^{12}$ independently of one another represent hydrogen, represent in each case optionally substituted alkyl, cycloalkyl, cycloalkylalkyl, aryl or arylalkyl,
$R^{11}$ and $R^{12}$ furthermore together represent in each case optionally substituted alkylene or alkenylene,
$R^{13}$ and $R^{14}$ independently of one another represent hydrogen, represent in each case optionally substituted alkyl or alkenyl,
$R^{15}$ represents hydrogen, —SO$_2$R$^6$, —COR$^6$ or —CO$_2$R$^6$; represents in each case optionally substituted alkyl, alkenyl, cycloalkyl, cycloalkylalkyl, aryl, arylalkyl, saturated or unsaturated heterocyclyl or heterocyclylalkyl.

Depending on the type and number of substituents, the compounds of the formula (I) can, if appropriate, be present as geometrical and/or optical isomers, regioisomers or isomer mixtures thereof in varying compositions. What is claimed by the invention are both the pure isomers and the isomer mixtures.

Furthermore, it has been found that $\Delta^1$-pyrrolines of the formula (I) can be prepared by A) reacting $\Delta^1$-pyrrolines of the formula (II)

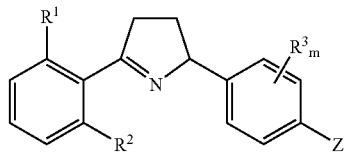

in which
$R^1$, $R^2$, $R^3$ and m have the meanings given above and
Z represents chlorine, bromine, iodine, —OSO$_2$CF$_3$ or —OSO$_2$(CF$_2$)$_3$CF$_3$, in a tandem reaction with heterocycles of the formula (III)

Q—X  (III)

in which

Q has the meaning given above and

X represents chlorine, bromine, iodine, —OSO$_2$CF$_3$ or —OSO$_2$(CF$_2$)$_3$CF$_3$, in the presence of a catalyst, in the presence of a diboronic acid ester and, if appropriate, in the presence of an acid binder and, if appropriate, in the presence of a diluent, or B) reacting Δ$^1$-pyrrolines of the formula (IV)

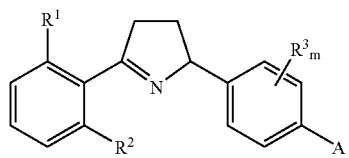
(IV)

in which

R$^1$, R$^2$, R$^3$ and m have the meanings given above and

A represents —B(OH)$_2$, (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl, with heterocycles of the formula (III)

Q—X  (III)

in which

Q and X have the meanings given above, in the presence of a catalyst, if appropriate in the presence of an acid binder and, if appropriate, in the presence of a diluent, or C) reacting Δ$^1$-pyrrolines of the formula (II)

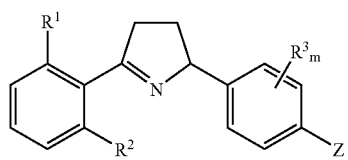
(II)

in which

R$^1$, R$^2$, R$^3$, m and Z have the meanings given above with boronic acid derivatives of the formula (V)

Q—A  (V)

in which

Q and A have the meanings given above, in the presence of a catalyst, if appropriate in the presence of an acid binder and, if appropriate, in the presence of a diluent, or D) reacting Δ$^1$-pyrrolines of the formula (II-a)

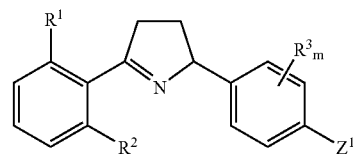
(II-a)

in which

R$^1$, R$^2$, R$^3$ and m have the meanings given above,

Z$^1$ represents bromine or iodine, with organometallic compounds of the formula (VI)

Q—M  (VI)

in which

Q has the meanings given above, and

M represents ZnCl, Sn(Me)$_3$ or Sn(n-Bu)$_3$, in the presence of a catalyst, if appropriate in the presence of an acid binder and, if appropriate, in the presence of a diluent.

Finally, it has been found that the compounds of the formula (I) according to the invention have very good insecticidal properties and can be used both in crop protection and in the protection of materials for controlling undesirable pests, such as insects.

The formula (I) provides a general definition of the Δ$^1$-pyrrolines according to the invention.

R$^1$ preferably represents halogen or methyl.

R$^2$ preferably represents hydrogen or halogen.

R$^3$ preferably represents halogen, represents in each case optionally halogen-substituted alkyl, alkoxy or alkylthio.

m preferably represents 0, 1, 2, 3 or 4.

Q preferably represents one of the groupings below

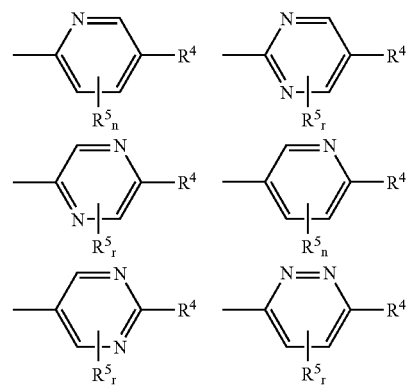

R$^4$ preferably represents hydrogen, halogen, cyano, formyl, nitro, trialkylsilyl; represents alkyl, alkenyl, alkoxy or alkenyloxy, each of which is optionally mono- or polysubstituted by identical or different substituents from the group consisting of halogen, cyano and —NR$^7$R$^8$; represents pentafluorothio, —S(O)$_p$R$^6$, —NR$^7$R$^8$, —COR$^6$, —CO$_2$R$^6$, —CONR$^9$R$^{10}$, —N(R$^{11}$)COR$^{12}$ or —C(R$^{13}$)═N—OR$^{14}$; or represents cycloalkyl, cycloalkylalkyl, aryl, arylalkyl, saturated or unsaturated, 5- to 10-membered heterocyclyl or heterocyclylalkyl, each of which is optionally mono- or polysubstituted by identical or different substituents from the group consisting of halogen, cyano, nitro, alkyl, halogenoalkyl, alkenyl, halogenoalkenyl, alkoxy, halogenoalkoxy, alkylthio and halogenoalkylthio.

$R^4$ furthermore preferably represents —CH=NOH, formyl; represents cycloalkyloxy or cycloalkylalkoxy, each of which is optionally mono- or polysubstituted by identical or different substituents from the group consisting of halogen and alkyl.

$R^5$ preferably represents halogen, cyano, formyl, nitro, trialkylsilyl; represents alkyl, alkenyl, alkoxy or alkenyloxy, each of which is optionally mono- or polysubstituted by identical or different substituents from the group consisting of halogen, cyano and —$NR^7R^8$; represents pentafluorothio, —$S(O)_pR^6$, —$NR^7R^8$, —$COR^6$, —$CO_2R^6$, —$CONR^9R^{10}$, —$N(R^{11})COR^{12}$ or —$C(R^{13})$=N—$OR^{14}$; or represents cycloalkyl, cycloalkylalkyl, aryl, arylalkyl, saturated or unsaturated, 5- to 10-membered heterocyclyl or heterocyclylalkyl, each of which is optionally mono- or polysubstituted by identical or different substituents from the group consisting of halogen, alkyl, halogenoalkyl, alkenyl, halogenoalkenyl, alkoxy, halogenoalkoxy, alkylthio and halogenoalkylthio.

p preferably represents 0, 1 or 2.

n preferably represents 0, 1, 2 or 3, where the substituents $R^5$ may be identical or different if n represents 2 or 3.

r preferably represents. 0, 1 or 2, where the substituents $R^5$ may be identical or different if r represents 2.

$R^6$ preferably represents alkyl which is optionally mono- or polysubstituted by identical or different substituents from the group consisting of halogen and —$NR^7R^8$, represents cycloalkyl, aryl or arylalkyl, each of which is optionally mono- or polysubstituted by identical or different substituents from the group consisting of halogen, cyano, alkyl, halogenoalkyl, alkoxy, halogenoalkoxy, alkylthio and halogenoalkylthio.

$R^6$ furthermore preferably represents alkyl which is mono- or polysubstituted by identical or different substituents, where the substituents may additionally be selected from the group consisting of alkoxy, alkylthio, halogenoalkoxy and halogenoalkylthio.

$R^7$ and $R^8$ independently of one another preferably represent hydrogen, —$SO_2R^6$, —$COR^6$, —$CO_2R^6$, represent alkyl or alkenyl, each of which is optionally mono- or polysubstituted by identical or different substituents from the group consisting of halogen, alkylcarbonyl, alkylcarbonyloxy, alkylamino, dialkylamino, alkoxy, halogenoalkoxy, alkylthio and halogenoalkylthio; represents cycloalkyl, cycloalkylalkyl, aryl, arylalkyl, saturated or unsaturated 5- to 10-membered heterocyclyl or heterocyclylalkyl, each of which is optionally mono- or polysubstituted by identical or different substituents from the group consisting of halogen, cyano, alkyl, halogenoalkyl, alkoxy, halogenoalkoxy, alkylthio and halogenoalkylthio.

$R^7$ and $R^8$ furthermore together preferably represent alkenylene which is optionally mono- or polysubstituted by identical or different substituents from the group consisting of halogen, cyano, alkoxy, halogenoalkoxy, alkylthio and halogenoalkylthio or represent alkylene which is optionally mono- or polysubstituted by identical or different substituents from the group consisting of halogen, cyano, alkyl, halogenoalkyl, alkoxy, halogenoalkoxy, alkylthio and halogenoalkylthio, where the alkylene chain may in each case be interrupted by —O—, —S— or —$NR^{15}$—, $R^7$ and $R^8$ furthermore together preferably represent alkylene which is mono- or polysubstituted by identical or different substituents, where the substituents may additionally be selected from the group consisting of alkoxycarbonyl and oxyalkyleneoxy.

$R^7$ and $R^8$ furthermore together preferably represent alkylene, where the alkylene chain is interrupted either by C=O or by C=NO-alkyl.

$R^9$ and $R^{10}$ independently of one another preferably represent hydrogen, —$SO_2R^6$, represent alkyl or alkenyl, each of which is optionally mono- or polysubstituted by identical or different substituents from the group consisting of halogen, alkylamino, dialkylamino, alkoxy and alkylthio; represent cycloalkyl, cycloalkylalkyl, aryl, arylalkyl, saturated or unsaturated 5- to 10-membered heterocyclyl or heterocyclylalkyl, each of which is optionally mono- or polysubstituted by identical or different substituents from the group consisting of halogen, cyano, alkyl, halogenoalkyl, alkoxy, halogenoalkoxy, alkylthio and halogenoalkylthio.

$R^9$ and $R^{10}$ furthermore together preferably represent alkylene which is optionally mono- or polysubstituted by identical or different substituents from the group consisting of halogen, cyano, alkyl, halogenoalkyl, alkoxy, halogenoalkoxy, alkylthio and halogenoalkylthio, where the alkylene chain may in each case be interrupted by —O—, —S— or —$NR^{15}$—, $R^{11}$ and $R^{12}$ independently of one another preferably represent hydrogen, represent alkyl which is optionally mono- or polysubstituted by identical or different substitutents from the group consisting of halogen, cyano, alkoxy and alkylthio, represent cycloalkyl, cycloalkylalkyl, aryl or arylalkyl, each of which is optionally mono- or polysubstituted by identical or different substituents from the group consisting of halogen, cyano, alkyl, halogenoalkyl, alkoxy, halogenoalkoxy, alkylthio and halogenoalkylthio.

$R^{11}$ and $R^{12}$ furthermore together preferably represent alkylene or alkenylene, each of which is optionally mono- or polysubstituted by identical or different substituents from the group consisting of halogen, alkyl, halogenoalkyl, alkoxy, halogenoalkoxy, alkylthio and halogenoalkylthio.

$R^{13}$ and $R^{14}$ independently of one another preferably represent hydrogen, represent alkyl or alkenyl, each of which is optionally mono- or polysubstituted by halogen.

$R^{15}$ preferably represents hydrogen, —$SO_2R^6$, —$COR^6$ or —$CO_2R^6$; represents alkyl or alkenyl, each of which is optionally mono- or polysubstituted by identical or different substituents from the group consisting of halogen, cyano, alkylamino, dialkylamino, alkoxy, halogenoalkoxy, alkylthio and halogenoalkylthio; represents cycloalkyl, cycloalkylalkyl, aryl, arylalkyl, saturated or unsaturated 5- to 10-membered heterocyclyl or heterocyclylalkyl, each of which is optionally mono- or polysubstituted by identical or different substituents from the group consisting of halogen, cyano, alkyl, halogenoalkyl, alkoxy, halogenoalkoxy, alkylthio and halogenoalkylthio.

$R^1$ particularly preferably represents fluorine, chlorine, bromine or methyl.

$R^2$ particularly preferably represents hydrogen, fluorine, chlorine or bromine.

$R^3$ particularly preferably represents fluorine, chlorine, bromine, represents $C_1$–$C_6$-alkyl, $C_1$–$C_6$-alkoxy or $C_1$–$C_6$-alkylthio, each of which is optionally mono- to octasubstituted by halogen.

m particularly preferably represents 0, 1, 2 or 3.

Q particularly preferably represents one of the groupings below

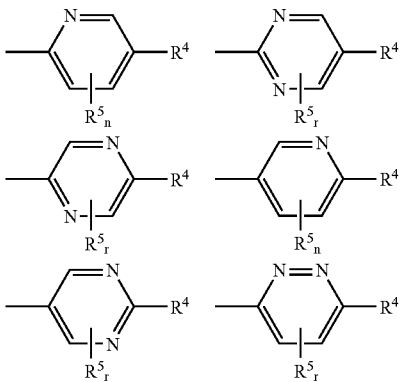

R⁴ particularly preferably represents hydrogen, fluorine, chlorine, bromine, cyano, formyl, nitro, tri-($C_1$–$C_6$-alkyl)silyl; represents $C_1$–$C_{20}$-alkyl, $C_2$–$C_{20}$alkenyl, $C_1$–$C_{20}$-alkoxy, $C_2$–$C_{20}$-alkenyloxy, each of which is optionally mono- or polysubstituted by identical or different substituents from the group consisting of halogen, cyano and —NR⁷R⁸; represents pentafluorothio, —S(O)$_n$R⁶, —NR⁷R⁸, —COR⁶, —CO₂R⁶, —CONR⁹R¹⁰, —N(R¹¹)COR¹² or —C(R¹³)=N—OR¹⁴; or represents $C_3$–$C_{12}$-cycloalkyl, $C_3$–$C_7$-cyclo-$C_1$–$C_4$-alkyl, aryl, aryl-$C_1$–$C_4$-alkyl, saturated or unsaturated, 5- to 10-membered heterocyclyl or heterocyclyl-$C_1$–$C_4$-alkyl having 1 to 4 heteroatoms, which comprise 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl or isoquinolinyl), each of which is optionally mono- to tetrasubstituted by identical or different substituents from the group consisting of halogen, cyano, nitro, $C_1$–$C_6$-alkyl, $C_1$–$C_6$-halogenoalkyl, $C_2$–$C_6$-alkenyl, $C_2$–$C_6$-halogenoalkenyl, $C_1$–$C_6$-alkoxy, $C_1$–$C_6$-halogenoalkoxy, $C_1$–$C_6$-alkylthio and $C_1$–$C_6$-halogenoalkylthio.

R⁴ furthermore particularly preferably represents —CH=NOH, formyl; represents $C_3$–$C_6$-cycloalkyloxy or $C_3$–$C_6$-cycloalkyl-$C_1$–$C_4$-alkoxy, each of which is optionally mono- to tetrasubstituted by identical or different substituents from the group consisting of fluorine, chlorine, bromine and $C_1$–$C_2$-alkyl.

R⁵ particularly preferably represents fluorine, chlorine, bromine, cyano, formyl, nitro, tri-($C_1$–$C_6$-alkyl)silyl; represents $C_1$–$C_6$-alkyl, $C_2$–$C_6$-alkenyl, $C_1$–$C_6$alkoxy, $C_2$–$C_6$-alkenyloxy, each of which is optionally mono- to tridecasubstituted by halogen; represents pentafluorothio, —S(O)$_p$R⁶, —NR⁷R⁸, —COR⁶, —CO₂R⁶, —CONR⁹R¹⁰ or —N(R¹¹)COR¹².

p particularly preferably represents 0, 1 or 2.

n particularly preferably represents 0, 1, 2 or 3, where the substituents R⁵ may be identical or different if n represents 2 or 3, r particularly preferably represents 0, 1 or 2, where the substituents R⁵ may be identical or different if r represents 2.

R⁶ particularly preferably represents $C_1$–$C_{20}$-alkyl which is optionally mono- or polysubstituted by identical or different substituents from the group consisting of halogen and —NR⁷R⁸, represents $C_3$–$C_6$-cycloalkyl, aryl or aryl-$C_1$–$C_4$-alkyl, each of which is optionally mono- to octasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

R⁶ furthermore particularly preferably represents $C_1$–$C_{20}$-alkyl which is mono- or polysubstituted by identical or different substituents, where the substituents may additionally be selected from the group consisting of $C_1$–$C_6$-alkoxy, $C_1$–$C_6$-alkylthio, $C_1$–$C_6$-halogenoalkoxy and $C_1$–$C_6$-halogenoalkylthio.

R⁷ and R⁸ independently of one another particularly preferably represent hydrogen, —SO₂R⁶, —COR⁶, —CO₂R⁶, represent $C_1$–$C_{20}$-alkyl or $C_2$–$C_{20}$-alkenyl, each of which is optionally mono- or polysubstituted by identical or different substituents from the group consisting of halogen, $C_1$–$C_6$-alkylcarbonyl, $C_1$–$C_6$-alkylcarbonyloxy, $C_1$–$C_6$-alkylamino, di-($C_1$–$C_6$-alkyl)amino, $C_1$–$C_6$alkoxy, $C_1$–$C_6$-halogenoalkoxy, $C_1$–$C_6$-alkylthio and $C_1$–$C_6$-halogenoalkylthio; represent $C_3$–$C_{12}$-cycloalkyl, $C_3$–$C_7$-cycloalkyl-$C_1$–$C_4$-alkyl, aryl, aryl-$C_1$–$C_4$alkyl, saturated or unsaturated 5- to 10-membered heterocyclyl or heterocyclyl-$C_1$–$C_4$-alkyl having 1 to 4 heteroatoms, which comprise 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl), each of which is optionally mono- to tetrasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

R⁷ and R⁸ furthermore independently of one another particularly preferably represent heterocyclyl-$C_1$–$C_4$-alkyl having 1 to 4 heteroatoms, which comprise 0 to 4 nitrogen atoms, 0 to 2 nonadjacent oxygen atoms and/or 0 to 2 nonadjacent sulphur atoms (in particular pyridinylmethyl, pyridinylethyl, pyrimidinylmethyl, pyrimidinylethyl, pyridazylmethyl, pyridazylethyl, pyrazinylmethyl or pyrazinylethyl), each of which is optionally mono- to tetrasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

R⁷ and R⁸ furthermore together particularly preferably represent $C_2$–$C_{12}$-alkenylene which is optionally mono- or polysubstituted by identical or different substituents from the group consisting of halogen, cyano, $C_1$–$C_6$-alkoxy, $C_1$–$C_6$-halogenoalkoxy, $C_1$–$C_6$-alkylthio and $C_1$–$C_6$-halogenoalkylthio or represent $C_3$–$C_{12}$-alkylene which is optionally mono- or polysubstituted in the alkylene moiety by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, where the alkylene chain may in each case be interrupted by —O—, —S— or —NR¹⁵—.

R[7] and R[8] furthermore together particularly preferably represent $C_3$–$C_{12}$-alkylene which is optionally mono- or polysubstituted by identical or different substituents, where the substituents may additionally be selected from the group consisting of $C_1$–$C_4$-alkoxycarbonyl and oxy-($C_1$–$C_4$-alkylene)-oxy.

R[7] and R[8] furthermore together particularly preferably represent $C_3$–$C_8$-alkylene, where the alkylene chain is interrupted either by C=O or C=NO—($C_1$–$C_6$alkyl).

R[9] and R[10] independently of one another particularly preferably represent hydrogen, —$SO_2R^6$, represent $C_1$–$C_6$-alkyl or $C_2$–$C_6$-alkenyl, each of which is optionally mono- to tridecasubstituted by identical or different substituents from the group consisting of halogen, $C_1$–$C_6$-alkyl)amino, di-($C_1$–$C_6$-alkyl)amino, $C_1$–$C_6$-alkoxy, $C_1$–$C_6$-halogenoalkoxy, $C_1$–$C_6$-alkylthio and $C_1$–$C_6$-halogenoalkylthio; represent $C_3$–$C_7$-cycloalkyl, $C_3$–$C_7$-cycloalkyl-$C_1$–$C_4$-alkyl, aryl, aryl-$C_1$–$C_4$-alkyl, saturated or unsaturated 5- to 10-membered heterocyclyl or heterocyclyl-$C_1$–$C_4$-alkyl having 1 to 4 heteroatoms, which comprise 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl), each of which is optionally mono- to tetrasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

R[9] and R[10] furthermore together particularly preferably represent $C_3$–$C_6$-alkylene, —$(CH_2)_2$—O—$(CH_2)_2$—, —$(CH_2)_2$—S—$(CH_2)_2$— or —$(CH_2)_2$—$N(R^{15})$—$(CH_2)_2$—, each of which is optionally mono- to tetrasubstituted in the alkylene moiety by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

R[11] and R[12] independently of one another particularly preferably represent hydrogen, represent $C_1$–$C_6$-alkyl which is optionally mono- to tridecasubstituted by identical or different substituents from the group consisting of halogen, cyano, $C_1$–$C_6$-alkoxy and $C_1$–$C_6$-alkylthio, represent $C_3$–$C_7$-cycloalkyl, $C_3$–$C_7$-cycloalkyl-$C_1$–$C_4$-alkyl, aryl or aryl-$C_1$–$C_4$-alkyl, each of which is optionally mono- to octasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

R[11] and R[12] furthermore together particularly preferably represent $C_3$–$C_{10}$-alkylene or $C_3$–$C_{10}$-alkenylene, each of which is optionally mono- to octasubstituted by identical or different substituents from the group consisting of halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

R[13] and R[14] independently of one another particularly preferably represent hydrogen, represent $C_1$–$C_6$-alkyl or $C_2$–$C_6$-alkenyl, each of which is optionally mono- or polysubstituted by halogen.

R[15] particularly preferably represents hydrogen, —$SO_2R^6$, —$COR^6$ or —$CO_2R^6$; represents $C_1$–$C_{20}$-alkyl or $C_2$–$C_{20}$-alkenyl, each of which is optionally mono- or polysubstituted by identical or different substituents from the group consisting of halogen, cyano, $C_1$–$C_6$-alkylamino, di-($C_1$–$C_6$-alkyl)amino, $C_1$–$C_6$-alkoxy, $C_1$–$C_6$-halogenoalkoxy, $C_1$–$C_6$-alkylthio and $C_1$–$C_6$-halogenoalkylthio; represents $C_3$–$C_{12}$-cycloalkyl, $C_3$–$C_7$-cycloalkyl-$C_1$–$C_4$alkyl, aryl, aryl-$C_1$–$C_4$-alkyl, saturated or unsaturated 5- to 10-membered heterocyclyl or heterocyclyl-$C_1$–$C_4$-alkyl having 1 to 4 heteroatoms, which comprise 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl), each of which is optionally mono- to tetrasubstituted by identical or different substituents from the group consisting of halogen, cyano, $C_1$–$C_6$-alkyl, $C_1$–$C_6$-halogenoalkyl, $C_1$–$C_6$alkoxy, $C_1$–$C_6$-halogenoalkoxy, $C_1$–$C_6$-alkylthio and $C_1$–$C_6$-halogenoalkylthio.

R[1] very particularly preferably represents fluorine, chlorine or methyl.

R[2] very particularly preferably represents hydrogen, fluorine or chlorine.

R[3] very particularly preferably represents fluorine, chlorine, $C_1$–$C_4$-alkyl, $C_1$–$C_4$alkoxy, $C_1$–$C_4$-alkylthio; $C_1$–$C_4$-halogenoalkyl, $C_1$–$C_4$-halogenoalkoxy, $C_1$–$C_4$-halogenoalkylthio having in each case 1 to 9 fluorine, chlorine and/or bromine atoms.

m very particularly preferably represents 0, 1 or 2.

Q very particularly preferably represents one of the groupings below

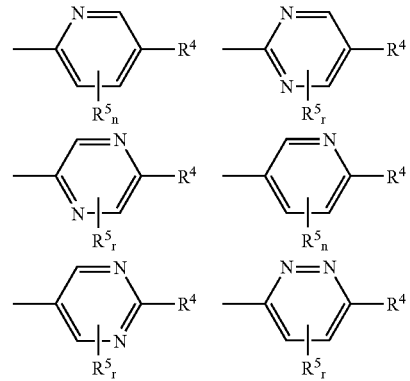

R[4] very particularly preferably represents hydrogen, fluorine, chlorine, bromine, cyano, formyl, nitro, tri-($C_1$–$C_4$-alkyl)silyl; represents $C_1$–$C_{16}$-alkyl, $C_2$–$C_{16}$alkenyl, $C_1$–$C_{16}$-alkoxy or $C_2$–$C_{16}$-alkenyloxy, each of which is optionally mono- or polysubstituted by identical or different substituents from the group consisting of fluorine, chlorine, bromine, cyano and —$NR^7R^8$; represents —$S(O)_pR^6$, —$NR^7R^8$, —$COR^6$, —$CO_2R^6$, —$CONR^9R^{10}$ or —$N(R^{11})COR^{12}$; or represents $C_3$–$C_{10}$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_2$–$C_6$-alkenyl, $C_2$–$C_6$-halogenoalkenyl, $C_1$–$C_4$-alkoxy, $C_1$–$C_4$-halogenoalkoxy, $C_1$–$C_4$-alkylthio and $C_1$–$C_4$-halogenoalkylthio.

$R^4$ furthermore very particularly preferably represents —CH=NOH, formyl; represents cyclopropyloxy, cyclobutyloxy, cyclopentyloxy, cyclohexyloxy, cyclopropylmethoxy, cyclobutylmethoxy, cyclopentylmethoxy or cyclohexylmethoxy, each of which is optionally mono- to trisubstituted by identical or different substituents from the group consisting of fluorine, chlorine and methyl.

$R^5$ very particularly preferably represents fluorine, chlorine, trimethylsilyl, represents $C_1$–$C_4$-alkyl, $C_2$–$C_6$-alkenyl, $C_1$–$C_4$-alkoxy or $C_2$–$C_6$-alkenyloxy, each of which is optionally mono- to nonasubstituted by identical or different substituents from the group consisting of fluorine, chlorine and bromine, represents —S(O)$_p$R$^6$, —NR$^7$R$^8$, —COR$^6$, —CO$_2$R$^6$ or —CONR$^9$R$^{10}$.

p very particularly preferably represents 0, 1 or 2.

n very particularly preferably represents 0, 1 or 2, where the substituents $R^5$ can be identical or different if n represents 2.

r very particularly preferably represents 0, 1 or 2, where the substituents $R^5$ can be identical or different if r represents 2.

$R^6$ very particularly preferably represents $C_1$–$C_{10}$-alkyl which is optionally mono- or polysubstituted by identical or different substituents from the group consisting of fluorine, chlorine, bromine and —NR$^7$R$^8$, represents cyclopropyl, cyclopentyl, cyclohexyl, phenyl or benzyl, each of which is optionally mono- to tetrasubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^6$ furthermore very particularly preferably represents $C_1$–$C_{10}$-alkyl which is mono- to trisubstituted by identical or different substituents, where the substituents may additionally be selected from the group consisting of $C_1$–$C_4$alkoxy, $C_1$–$C_4$-alkylthio, $C_1$–$C_4$-halogenoalkoxy and $C_1$–$C_4$-halogenoalkylthio.

$R^7$ and $R^8$ independently of one another very particularly preferably represent hydrogen, —SO$_2$R$^6$, —COR$^6$, —CO$_2$R$^6$, represent $C_1$–$C_{16}$-alkyl or $C_2$–$C_{16}$-alkenyl, each of which is optionally mono- or polysubstituted by identical or different substituents from the group consisting of fluorine, chlorine, bromine, $C_1$–$C_4$alkylcarbonyl, $C_1$–$C_4$-alkylcarbonyloxy, $C_1$–$C_4$-alkylamino, di-($C_1$–$C_4$-alkyl)amino, $C_1$–$C_4$-alkoxy, $C_1$–$C_4$-halogenoalkoxy, $C_1$–$C_4$-alkylthio and $C_1$–$C_4$-halogenoalkylthio; represent $C_3$–$C_{10}$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^7$ and $R^8$ furthermore independently of one another very particularly preferably represent pyridinylmethyl, pyridinylethyl, pyrimidinylmethyl, pyrimidinylethyl, pyridazylmethyl, pyridazylethyl, pyrazinylmethyl or pyrazinylethyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^7$ and $R^8$ furthermore together very particularly preferably represent $C_2$–$C_{10}$-alkenylene, which is optionally mono- or polysubstituted by identical or different substituents from the group consisting of fluorine, chlorine, bromine, $C_1$–$C_4$-alkoxy, $C_1$–$C_4$-halogenoalkoxy, $C_1$–$C_4$-alkylthio and $C_1$–$C_4$-halogenoalkylthio or represent $C_3$–$C_{10}$-alkylene, which is optionally mono- or polysubstituted in the alkylene moiety by identical or different substituents from the group consisting of fluorine, chlorine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio, where the alkylene chain may in each case be interrupted by —O—, —S— or —NR$^{15}$—, $R^7$ and $R^8$ furthermore together very particularly preferably represent $C_3$–$C_{10}$alkylene which is mono- to trisubstituted by identical or different substituents, where the substituents may additionally be selected from n-propoxycarbonyl, isopropoxycarbonyl, ethoxycarbonyl, methoxycarbonyl, oxypropyleneoxy, oxyethyleneoxy and oxymethyleneoxy.

$R^7$ and $R^8$ furthermore together very particularly preferably represent $C_3$–$C_6$-alkylene, where the alkylene chain is interrupted either by C=O or by C=NO—($C_1$–$C_4$-alkyl).

$R^9$ and $R^{10}$ independently of one another very particularly preferably represent hydrogen, —SO$_2$R$^6$, represent $C_1$–$C_4$-alkyl or $C_2$–$C_6$-alkenyl, each of which is optionally mono- to nonasubstituted by identical or different substituents from the group consisting of fluorine, chlorine, bromine, $C_1$–$C_4$-alkylamino, di-($C_1$–$C_4$-alkyl)amino, $C_1$–$C_4$-alkoxy, $C_1$–$C_4$-halogenoalkoxy, $C_1$–$C_4$-alkylthio and $C_1$–$C_4$-halogenoalkylthio; represent $C_3$–$C_6$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, $C_1$–$C_4$-alkyl, cyano, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^9$ and $R^{10}$ furthermore together very particularly preferably represent $C_4$–$C_5$alkylene, —(CH$_2$)$_2$—O—(CH$_2$)$_2$—, —(CH$_2$)$_2$—S—(CH$_2$)$_2$—, —(CH$_2$)$_2$—N(R$^{15}$)—(CH$_2$)$_2$—, each of which is optionally mono- to tetrasubstituted in the alkylene moiety by identical or different substituents from the group consisting of fluorine, chlorine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^{11}$ and $R^{12}$ independently of one another very particularly preferably represent hydrogen, represent $C_1$–$C_6$-alkyl which is optionally mono- to nonasubstituted by identical or different substituents from the group consisting of fluorine, chlorine, bromine, $C_1$–$C_4$-alkoxy and $C_1$–$C_4$-alkylthio, represent $C_3$–$C_6$-cycloalkyl, $C_3$–$C_6$-cycloalkyl-$C_1$–$C_4$-alkyl, phenyl, benzyl or phenylethyl, each of which is optionally mono- to tetrasubstituted by identical or different substituents from the group consisting of fluorine, chlorine, bromine, $C_1$–$C_4$alkyl, $C_1$–$C_4$-halogenoalkyl, $C_1$–$C_4$-alkoxy, $C_1$–$C_4$-halogenoalkoxy, $C_1$–$C_4$alkylthio and $C_1$–$C_4$-halogenoalkylthio.

$R^{11}$ and $R^{12}$ furthermore together very particularly preferably represent $C_3$–$C_8$alkylene or $C_3$–$C_8$-alkenylene, each of which is optionally mono- to tetrasubstituted by identical or different substituents from the group consisting of fluorine, chlorine, bromine, $C_1$–$C_4$-alkyl, $C_1$–$C_4$-halogenoalkoxy, $C_1$–$C_4$alkoxy, $C_1$–$C_4$-halogenoalkoxy, $C_1$–$C_4$-alkylthio and $C_1$–$C_4$-halogenoalkylthio.

$R^{15}$ very particularly preferably represents hydrogen, —$SO_2R^6$, represents —$COR^6$ or —$CO_2R^6$; represents $C_1$–$C_{16}$-alkyl or $C_2$–$C_{16}$-alkenyl, each of which is optionally mono- or polysubstituted by identical or different substituents from the group consisting of fluorine, chlorine, bromine, cyano, methylamino, ethylamino, di-($C_1$–$C_6$-alkyl)amino, $C_1$–$C_4$-alkoxy, $C_1$–$C_4$-halogenoalkoxy, $C_1$–$C_4$-alkylthio and $C_1$–$C_4$-halogenoalkylthio; represents $C_3$–$C_{10}$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^1$ especially preferably represents fluorine or chlorine.

$R^2$ especially preferably represents hydrogen or fluorine.

$R^3$ especially preferably represents fluorine, chlorine, methyl, ethyl, n-propyl, isopropyl, n-butyl, isobutyl, sec-butyl, tert-butyl, trifluoromethyl, trifluoroethyl, methoxy, ethoxy, n-propoxy, isopropoxy, n-butoxy, isobutoxy, sec-butoxy, tert-butoxy, trifluoromethoxy, trifluoroethoxy, methylthio, ethylthio, n-propylthio, isopropylthio, n-butylthio, isobutylthio, sec-butylthio, tert-butylthio, trifluoromethylthio or trifluoroethylthio.

m especially preferably represents 0 or 1.

Q especially preferably represents one of the groupings below

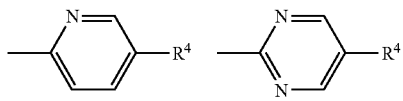

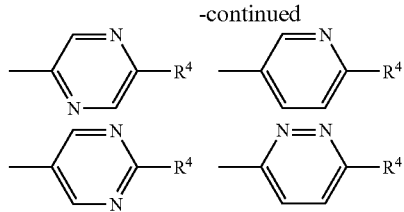

$R^4$ especially preferably represents hydrogen, fluorine, chlorine, bromine, cyano, formyl, represents $C_1$–$C_{16}$-alkyl, $C_2$–$C_{16}$-alkenyl, $C_1$–$C_{16}$-alkoxy, $C_2$–$C_{16}$-alkenyloxy, each of which is optionally mono- or polysubstituted by identical or different substituents from the group consisting of fluorine, chlorine, bromine, cyano and —$NR^7R^8$; represents —$S(O)_pR^6$, —$NR^7R^8$, —$COR^6$, —$CO_2R^6$, —$CONR^9R^{10}$, —$N(R^{11})COR^{12}$;
or represents cyclopropyl, cyclopentyl, cyclohexyl, cyclopropylmethyl, cyclopentylmethyl, cyclohexylmethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl or isoquinolinyl, each of which is optionally mono- to trisubstituted by identical or different substituents from the group consisting of fluorine, chlorine, bromine, cyano, methyl, ethyl, n-propyl, isopropyl, —$CF_3$, —$CHF_2$, —$CClF_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, vinyl, allyl, 1-propenyl, butenyl, —CF=CHF, —CF=$CH_2$, —CF=$CCl_2$, —CH=$CF_2$, —$CF_2$CF=$CF_2$, —CH=CFH, —$CH_2$CF=$CF_2$, —CF=$CF_2$, —$CF_2$CH=$CF_2$, methoxy, ethoxy, n-propoxy, isopropoxy, n-butoxy, isobutoxy, sec-butoxy, tert-butoxy, trifluoromethoxy, difluoromethoxy, chlorodifluoromethoxy, trifluoroethoxy, methylthio, ethylthio, n-propylthio, isopropylthio, n-butylthio, isobutylthio, sec-butylthio, tert-butylthio, trifluoromethylthio, difluoromethylthio, chlorodifluoromethylthio and trifluoroethylthio.

$R^4$ furthermore especially preferably represents —CH=NOH, formyl, cyclopropyloxy, cyclobutyloxy, cyclopentyloxy, cyclohexyloxy, cyclopropylmethoxy, cyclobutylmethoxy, cyclopentylmethoxy or cyclohexylmethoxy.

p especially preferably represents 0, 1 or 2.

$R^6$ especially preferably represents methyl, ethyl, n-propyl, isopropyl, n-butyl, isobutyl, sec-butyl, tert-butyl, pentyl, hexyl, —$CF_3$, —$CHF_2$, —$CCl_3$, —$CCl_2F$, dimethylaminomethyl, dimethylaminoethyl, diethylaminomethyl, diethylaminoethyl, cyclopropyl, cyclopentyl, cyclohexyl, phenyl or benzyl.

$R^6$ furthermore especially preferably represents methoxymethyl, trifluoromethoxymethyl, methylthiomethyl or trifluoromethylthiomethyl.

$R^7$ and $R^8$ independently of one another especially preferably represent hydrogen, —$SO_2R^6$, —$COR^6$, —$CO_2R^6$, represent $C_1$–$C_{16}$-alkyl or $C_2$–$C_{16}$-alkenyl, each of which is optionally mono- or polysubstituted by identical or different substituents from the group consisting of fluorine, chlorine, bromine, $C_1$–$C_4$alkylcarbonyl, $C_1$–$C_4$- alkylcarbonyloxy, $C_1$–$C_4$-alkylamino, di-($C_1$–$C_4$alkyl)amino, $C_1$–$C_4$-alkoxy, $C_1$–$C_4$-halogenoalkoxy, $C_1$–$C_4$-alkylthio or $C_1$–$C_4$-halogenoalkylthio; represent $C_3$–$C_8$-cycloalkyl, cyclopropylmethyl, cyclopentylmethyl, cyclohexylmethyl, cyclopropylethyl, cyclopentylethyl, cyclohexylethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^7$ and $R^8$ furthermore independently of one another especially preferably represent pyridinylmethyl, pyrimidinylmethyl, pyridazylmethyl or pyrazinylmethyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^7$ and $R^8$ furthermore together especially preferably represent $C_2$–$C_8$-alkenylene, which is optionally mono- or polysubstituted by identical or different substituents from the group consisting of fluorine, chlorine, bromine, $C_1$–$C_4$alkoxy, $C_1$–$C_4$-halogenoalkoxy, $C_1$–$C_4$-alkylthio and $C_1$–$C_4$-halogenoalkylthio or represent $C_3$–$C_8$-alkylene, which is optionally mono- or polysubstituted in the alkylene moiety by identical or different substituents from the group consisting of fluorine, chlorine, cyano, methyl, ethyl, n-propyl, isopropyl, n-butyl, isobutyl, sec-butyl, tert-butyl, $C_1$–$C_4$-halogenoalkyl, methoxy, ethoxy, n-propoxy, isopropoxy, n-butoxy, isobutoxy, sec-butoxy, tert-butoxy, $C_1$–$C_4$-halogenoalkoxy, methylthio, ethylthio, n-propylthio, isopropylthio, n-butylthio, isobutylthio, sec-butylthio, tert-butylthio and $C_1$–$C_4$-halogenoalkylthio, where the alkylene chain may in each case be interrupted by —O—, —S— or —$NR^{15}$—.

$R^7$ and $R^8$ furthermore together especially preferably represent $C_3$–$C_8$-alkylene which is mono- or disubstituted by identical or different substituents, where the substituents may additionally be selected from the group consisting of ethoxycarbonyl, methoxycarbonyl and oxyethyleneoxy.

$R^7$ and $R^8$ furthermore together especially preferably represent —$CH_2$—$CH_2$—C(=O)—$CH_2$—$CH_2$—, —$CH_2$—$CH_2$—C(=NO-Me)—$CH_2$—$CH_2$—, —$CH_2$—$CH_2$—C(=NO-Et)-$CH_2$—$CH_2$— or —$CH_2$—$CH_2$—C(=NO-iPr)—$CH_2$—$CH_2$—.

$R^9$ and $R^{10}$ independently of one another especially preferably represent hydrogen, —$SO_2CF_3$, methyl, ethyl, n-propyl, isopropyl, n-butyl, isobutyl, sec-butyl, tert-butyl, pentyl, hexyl, —$CF_3$, —$CH_2CF_3$, —$(CF_2)_3CF_3$, cyclopropyl, cyclopentyl, cyclohexyl, methoxymethyl, methoxyethyl, or represent phenyl or benzyl, each of which is optionally substituted by fluorine, chlorine, bromine, methyl, trifluoromethyl, methoxy or trifluoromethoxy.

$R^9$ and $R^{10}$ furthermore together especially preferably represent —$(CH_2)_4$—, —$(CH_2)_5$—, —$(CH_2)_6$—, —$CH_2$—CH($CH_3$)—$CH_2$—CH($CH_3$)—$CH_2$—, —$(CH_2)_2$—O—$(CH_2)_2$—, —$(CH_2)_2$—S—$(CH_2)_2$— or —$(CH_2)_2$—N($R^{15}$)—$(CH_2)_2$—.

$R^{11}$ and $R^{12}$ independently of one another especially preferably represent methyl, ethyl, n-propyl, isopropyl, n-butyl, isobutyl, sec-butyl, tert-butyl, n-hexyl, trifluoromethyl, trifluoroethyl, cyclopropyl, cyclopentyl, cyclohexyl, or represent phenyl or benzyl, each of which is optionally substituted by fluorine, chlorine, bromine, methyl, trifluoromethyl, methoxy or trifluoromethoxy.

$R^{11}$ and $R^{12}$ furthermore together especially preferably represent —$(CH_2)_3$—, —$(CH_2)_4$—, —$(CH_2)_5$— or —$(CH_2)_6$—, each of which is optionally substituted by fluorine, chlorine, bromine, methyl, ethyl, methoxy, ethoxy, methylthio, ethylthio, trifluoromethyl, trifluoromethoxy or trifluoromethylthio.

$R^{15}$ especially preferably represents hydrogen, —$SO_2R^6$, represents —$COR^6$ or —$CO_2R^6$; represents $C_1$–$C_{16}$-alkyl, $C_2$–$C_{16}$-alkenyl, each of which is optionally mono- or polysubstituted by identical or different substituents from the group consisting of fluorine, chlorine, bromine, cyano, methylamino, ethylamino, di-($C_1$–$C_6$-alkyl)amino, $C_1$–$C_4$-alkoxy, $C_1$–$C_4$-halogenoalkoxy, $C_1$–$C_4$-alkylthio and $C_1$–$C_4$-halogenoalkylthio;

represents $C_3$–$C_8$-cycloalkyl, cyclopropylmethyl, cyclopentylmethyl, cyclohexylmethyl, cyclopropylethyl, cyclopentylethyl, cyclohexylethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, methyl, ethyl, n-propyl, isopropyl, n-butyl, isobutyl, sec-butyl, tert-butyl, $C_1$–$C_4$-halogenoalkyl, methoxy, ethoxy, n-propoxy, isopropoxy, n-butoxy, isobutoxy, sec-butoxy, tert-butoxy, $C_1$–$C_4$-halogenoalkoxy, methylthio, ethylthio, n-propylthio, isopropylthio, n-butylthio, isobutylthio, sec-butylthio, tert-butylthio and $C_1$–$C_4$-halogenoalkylthio.

Very particular preference is furthermore given to compounds of the formulae (I-a) to (I-f)

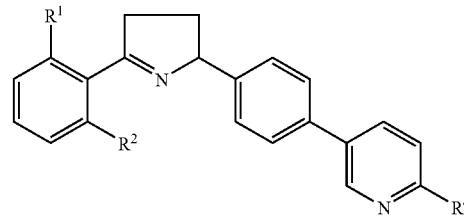

(I-a)

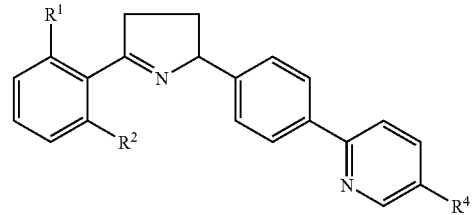

(I-b)

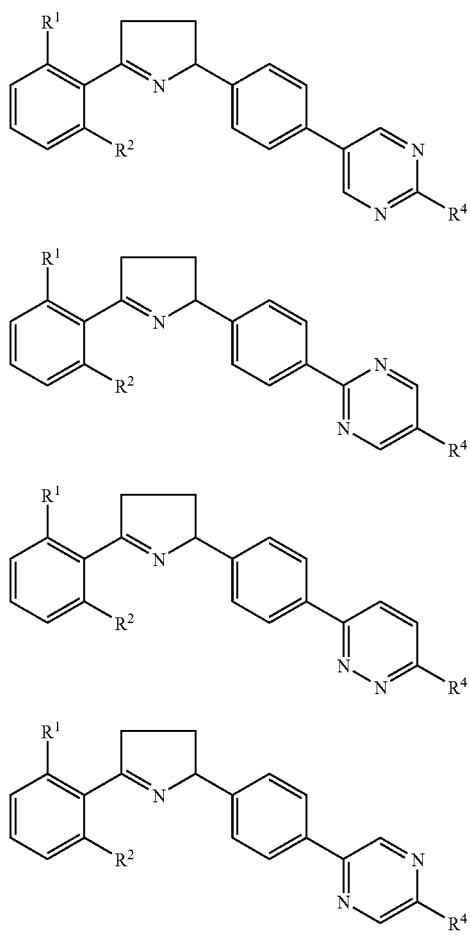

in which in each case
R¹ represents fluorine or chlorine,
R² represents hydrogen or fluorine and
R⁴ has the meanings given above.

Very particular preference is furthermore given to (R)-configured compounds of the formulae (I-g) to (I-l)

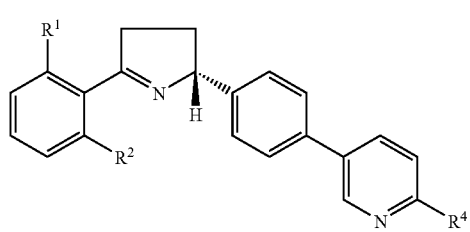

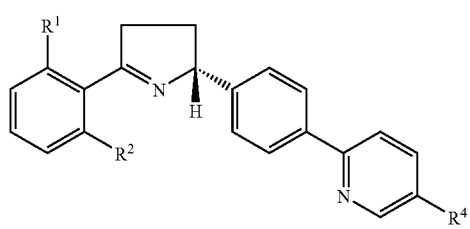

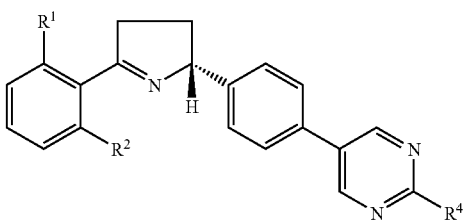

in which in each case
R¹ represents fluorine or chlorine,
R² represents hydrogen or fluorine and
R⁴ has the meanings given above.

Compounds of the formulae (I-g) to (I-l) are obtained by customary processes for optical resolution, such as, for example, by chromatographing the corresponding racemates on a chiral stationary phase. In this manner, it is possible to separate both racemic end products and racemic intermediates into the two enantiomers.

Saturated hydrocarbon radicals, such as alkyl, can in each be straight-chain or branched as far as this is possible, including in combination with heteroatoms, such as, for example, in alkoxy.

Halogen-substituted radicals, for example halogenoalkyl, are mono- or polyhalogenated, up to the maximum number of possible substituents. In the case of polyhalogenation, the halogen atoms can be identical or different. Halogen represents fluorine, chlorine, bromine or iodine, in particular fluorine, chlorine or bromine.

However, the abovementioned general or preferred radical definitions or illustrations can also be combined with one another as desired, i.e. between the respective ranges and preferred ranges. They apply both to the end products and, correspondingly, to the precursors and intermediates.

Using 5-(2,6-difluorophenyl)-2-(4-bromophenyl)-3,4-dihydro-2H-pyrrole, N-(5-bromo-2-pyrimidinyl)-N-ethyl-N- propylamine and 4,4,4',4',5,5,5',5'-octamethyl-2,2'-bis-1,3,2-dioxaborolane as starting materials and a palladium catalyst, the course of the process (A) according to the invention can be illustrated by the equation below.

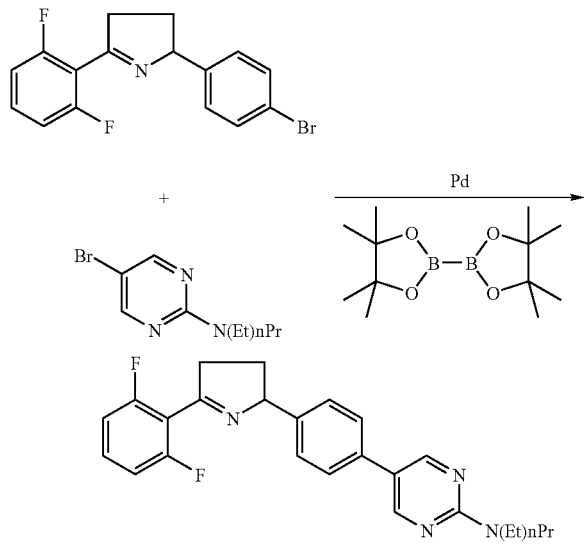

Using 5-(2,6-difluorophenyl)-2-[4-(4,4,5,5-tetramethyl-1,3,2-dioxaborolan-2-yl)phenyl]-3,4-dihydro-2H-pyrrole and 5-bromo-2-(2,2,2-trifluoroethoxy)pyrimidine starting materials and a palladium catalyst, the course of the process (B) according to the invention can be illustrated by the equation below.

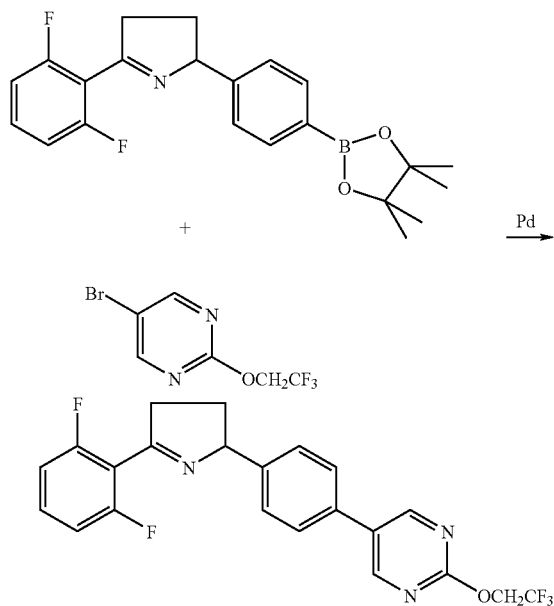

Using 5-(2,6-difluorophenyl)-2-[4-(trifluoromethylsulphonyloxy)phenyl]-3,4-dihydro-2H-pyrrole and 6-(dimethylamino)-3-pyridazinylboronic acid as starting materials and a palladium catalyst, the course of process (C) according to the invention can be illustrated by the equation below.

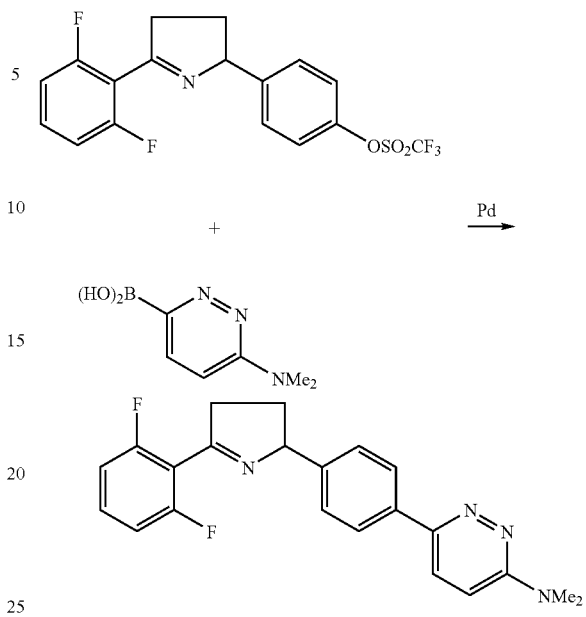

Using 5-(2,6-difluorophenyl)-2-(4-bromophenyl)-3,4-dihydro-2H-pyrrole and 2-trifluoromethyl-5-(tributylstannyl)pyridine as starting materials and a palladium catalyst, the course of the process (D) according to the invention can be illustrated by the equation below.

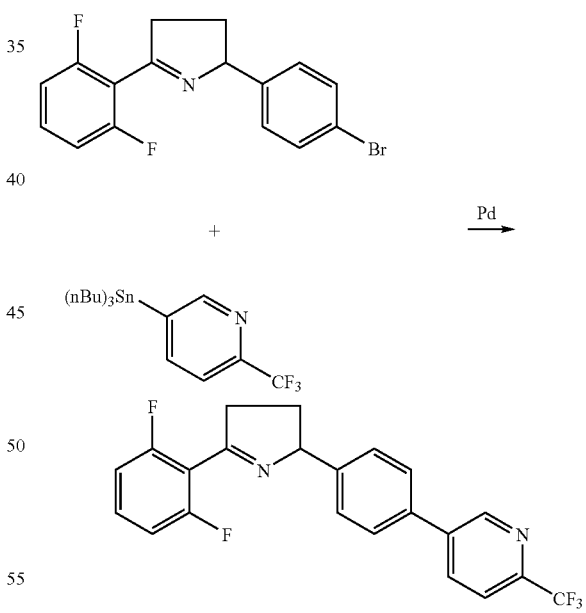

Explanation of the Process and Intermediates

Process (A)

In a first reaction step, a compound of the formula (II) is coupled with a diboronic acid ester in the presence of a palladium catalyst, if appropriate in the presence of an acid binder and if appropriate in the presence of a solvent. Without any isolation of the intermediate, a compound of the formula (III) is coupled in the same reaction vessel in a second reaction step in the presence of a catalyst, if appropriate in the presence of an acid binder and if appropriate in the presence of a solvent (cf., for example, Tetrahedron Lett. 1997, 38, 3841).

The process (A) according to the invention can be carried out in two variants. It is possible either to initially charge a compound of the formula (II) or to initially charge a compound of the formula (m). Process (A) is to be considered a tandem reaction of the processes (B) and (C) described below.

The formula (II) provides a general definition of the $\Delta^1$-pyrrolines required as starting materials for carrying out the process (A). In this formula, $R^1$, $R^2$, $R^3$ and m preferably, particularly preferably and very particularly preferably have those meanings which have already been mentioned in connection with the description of the compounds of the formula (I) as being preferred, particularly preferred, etc., for these radicals. Z preferably represents bromine, iodine, —$OSO_2CF_3$ or —$OSO_2(CF_2)_3CF_3$, particularly preferably bromine, —$OSO_2CF_3$ or —$OSO_2(CF_2)_3CF_3$, very particularly preferably bromine or —$OSO_2CF_3$.

$\Delta^1$-Pyrrolines of the formula (II) can be prepared by known processes (cf. WO 98/22438).

The formula (III) provides a general definition of the heterocycles required as starting materials for carrying out the process (A) according to the invention. In this formula, Q preferably, particularly preferably and very particularly preferably has those meanings which have already been mentioned in connection with the description of the compounds of the formula (I) according to the invention as being preferred, particularly preferred, etc., for these radicals. X preferably represents bromine, chlorine, iodine or —$OSO_2CF_3$, particularly preferably bromine, chlorine or iodine, very particularly preferably bromine or chlorine.

The heterocycles of the formula (III) are known or can be prepared by known processes (cf. Aust. J. Chem. 1964, 17, 794; Chem. Ber. 1992, 125, 1169; Chem. Pharm. Bull. 1995, 43, 247; Eur. J. Med. Chem. 1989, 24, 249; J. Chem. Soc. C 1971, 1889; J. Chem. Soc. Perkin Trans. 1 1995, 2497; J. Med. Chem. 1991, 34, 315; J. Org. Chem. 1984, 49 2240; J. Org. Chem. 1990, 55, 69; Org. Prep. Proced. Int. 1998, 30, 433; Synthesis 1999, 1163; Tetrahedron 1999, 40, 7975; Tetrahedron Lett. 1996, 37, 4447; Tetrahedron Lett. 2000, 41, 4335).

Suitable diboronic acid esters for carrying out process (A) according to the invention are 4,4',4',5,5,5',5'-octamethyl-2,2'-bis-1,3,2-dioxaborolane, 5,5,5',5'-tetramethyl-2,2'bis-1,3,2-dioxaborinane, 4,4,4',4',6,6'-hexamethyl-2,2'-bis-1,3,2-dioxaborinane or 2,2'-bis-1,3,2-benzodioxaborole. Preference is given to using 4,4,4',4',5,5,5',5'octamethyl-2,2'-bis-1,3,2-dioxaborolane, 5,5,5',5'-tetramethyl-2,2'-bis-1,3,2-dioxaborinane or 4,4,4',4',6,6'-hexamethyl-2,2'-bis-1,3,2-dioxaborinane, particularly preferably 4,4,4',4',5,5,5',5'-octamethyl-2,2'-bis-1,3,2-dioxaborolane or 5,5,5',5'tetramethyl-2,2'-bis-1,3,2-dioxaborinan, very particularly preferably 4,4,4',4',5,5,5',5'octamethyl-2,2'-bis-1,3,2-dioxaborolane.

When carrying out the process (A) according to the invention, in general 1 mol or a slight excess of a diboronic ester and 1 mol or slight excess of a compound of the formula (III), and 3% of a palladium catalyst, are employed per mole of the compound of the formula (II). However, it is also possible to employ the reaction components in other ratios. It is possible to initially charge the compound of the formula (II) or, alternatively, the compound of the formula (III). Work-up is carried out by customary methods. In general, the reaction mixture is diluted with water and extracted with ethyl acetate. The organic phase is washed, dried, filtered and concentrated. The residue is, if appropriate, freed from any impurities that may still be present using customary methods, such as chromatography or recrystallization.

Process (B)

The formula (IV) provides a general definition of the $\Delta^1$-pyrrolines required as starting materials for carrying out the process (B) according to the invention. In this formula, $R^1$, $R^2$, $R^3$ and m preferably, particularly preferably and very particularly preferably have those meanings which have already been mentioned in connection with the description of the compounds of the formula (1) according to the invention as being preferred, particularly preferred, etc., for these radicals. A preferably represents (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl, particularly preferably (4,4,5,5-tetramethyl-1,3,2-dioxaborolan)-2-yl, (5,5-dimethyl-1,3,2-dioxaborinan)-2-yl or (4,4,6-trimethyl-1,3,2-dioxaborinan)-2-yl, very particularly preferably (4,4,5,5-tetramethyl-1,3,2-dioxaborolan)-2-yl or (5,5-dimethyl-1,3,2-dioxaborinan)-2-yl.

$\Delta^1$-Pyrrolines of the formula (IV) can be prepared by
a) reacting compounds of the formula (II)

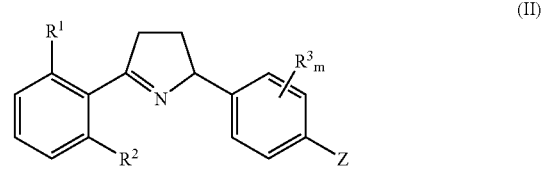

(II)

in which
$R^1$, $R^2$, $R^3$, m and Z have the meanings given above,
with a diboronic acid ester in the presence of a catalyst, if appropriate in the presence of an acid binder and if appropriate in the presence of a diluent (cf.
J. Org. Chem. 1995, 60, 7508; Tetrahedron Lett. 1997, 38, 3447).

Diboronic acid esters suitable for carrying out the process (a) have already been mentioned in the description of the process (A) according to the invention.

The heterocycles of the formula (m) required as starting materials for carrying out the process (B) according to the invention have already been described above in the description of process (A).

When carrying out the process (B) according to the invention, in general 1 mol or a slight excess of a compound of the formula (III) is employed per mole of the compound of the formula (IV). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. The residue is, if appropriate, freed from any impurities that may still be present using customary methods, such as chromatography or recrystallization.

Process (C)

The $\Delta^1$-pyrrolines of the formula (II) required as starting materials for carrying out the process (C) according to the invention have already been described in the description of process (A).

The formula (V) provides a general definition of the boronic acid derivatives required as starting materials for carrying out the process (C) according to the invention. In this formula, Q preferably, particularly preferably and very particularly preferably has those meanings which have already been mentioned in connection with the description of the compounds of the formula (I) according to the invention as being preferred, particularly preferred, etc., for these radicals. A preferably represents (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl, particularly preferably (4,4,5,5-tetramethyl-1,3,2-dioxaborolan)-2-yl, (5,5-dimethyl-1,3,2-dioxaborinan)-2-yl or (4,4,6-trimethyl-1,3,2-dioxaborinan)-2-yl, very particularly preferably (4,4,5,5-tetramethyl-1,3,2-dioxaborolan)-2-yl or (5,5-dimethyl-1,3,2-dioxaborinan)-2-yl.

The compounds of the formula (V) are known or can be prepared by known processes (cf. J. Org. Chem. 1995, 60, 7508, Tetrahedron lett. 1997, 38, 3447).

When carrying out the process (C) according to the invention, in general 1 mol or a slight excess of a compound of the formula (V) is employed per mole of the compound of the formula (II). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. The residue is, if appropriate, freed from any impurities that may still be present using customary methods, such as chromatography or recrystallization.

Process (D)

The formula (II-a) provides a general definition of the $\Delta^1$-pyrrolines required as starting materials for carrying out the process (D) according to the invention. In this formula, $R^1$, $R^2$, $R^3$ and m preferably, particularly preferably and very particularly preferably have those meanings which have already been mentioned in connection with the description of the compounds of the formula (I) according to the invention as being preferred, particularly preferred, etc., for these radicals. $Z^1$ preferably represents bromine or iodine.

$\Delta^1$-Pyrrolines of the formula (II-a) can be prepared by known processes (cf. WO 98/22438).

The formula (VI) provides a general definition of the organometallic compounds required as starting materials for carrying out the process (D) according to the invention. In this formula, Q preferably, particularly preferably and very particularly preferably has those meanings which have already been mentioned in connection with the description of the compounds of the formula (I) according to the invention as being preferred, particularly preferred, etc., for these radicals. M preferably represents ZnCl, Sn(Me)$_3$ or Sn(n-Bu)$_3$.

Some of the organometallic compounds of the formula (VI) are already known, or can be prepared by known methods. It is possible, for example, to prepare compounds of the formula (VI) in situ from the corresponding compounds of the formula (III) in which X represents —OSO$_2$CF$_3$ (cf. Tetrahedron Lett. 1995, 36, 9085).

When carrying out the process (D) according to the invention, in general 1 mol or a slight excess of a compound of the formula (VI) is employed per mole of the compound of the formula (II-a). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. The residue is, if appropriate, freed from any impurities that may still be present using customary methods, such as chromatography or recrystallization.

Chiral Compounds of the Formulae (I-g) to (I-l)

To prepare chiral compounds of the formulae (I-g) to (I-l), it is possible, for example, to subject $\Delta^1$-pyrrolines of the formula (1'-b)

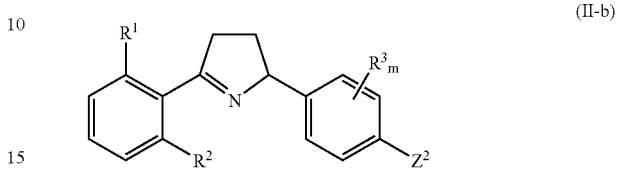

(II-b)

in which $R^1$, $R^2$, $R^3$ and m have the meanings given above and $Z^2$ represents chlorine, bromine or iodine to an optical resolution. To this end, for example, methods of preparative chromatography, preferably the high performance liquid chromagraphy (HPLC) method, are employed. Here, a chiral stationary silica gel phase is used. A tris(3,5-dimethylphenylcarbamate)-cellulose-modified silica gel has been found to be particularly suitable for separating the compounds of the formula (II-b) into the two enantiomers. This separating material is commercially available. However, it is also possible to use other stationary phases. Suitable mobile phases are all customary inert organic solvents, and mixtures of these. Preference is given to using optionally halogenated aliphatic, alicyclic or aromatic hydrocarbons, such as petroleum ether, hexane, heptane, cyclohexane; dichloromethane, chloroform; alcohols, such as methanol, ethanol, propanol; nitriles, such as acetonitrile; esters, such as methyl acetate or ethyl acetate. Particular preference is given to using aliphatic hydrocarbons, such as hexane or heptane, and alcohols, such as methanol or propanol, very particularly preferably n-heptane and isopropanol or mixtures of these. In general, the separation is carried out at temperatures between 10° C. and 60° C., preferably between 10° C. and 40° C., particularly preferably at room temperature. The (R)-configured enantiomers obtained in this manner are then used as starting materials for the processes (A), (C) or (D).

When carrying out the processes (A), (B), (C) and (D) according to the invention, in each case a palladium catalyst is employed, which for its part can be used with or without addition of further ligands. The catalyst used is preferably PdCl$_2$(dppf) [dppf=1,1'-bis(diphenylphosphino)ferrocene], Pd(PPh$_3$)$_4$, PdCl$_2$(PPh$_3$)$_2$, PdCl$_2$(CH$_3$CN)$_2$, Pd$_2$(dba)$_3$ [dba=dibenzylideneacetone] or Pd(OAc)$_2$, particularly preferably PdCl$_2$(dppf), Pd(PPh$_3$)$_4$, PdCl$_2$(PPh$_3$)$_2$ or Pd(OAc)$_2$, very particularly preferably PdCl$_2$(dppf) or PdCl$_2$(PPh$_3$)$_2$.

Suitable ligands are triarylphosphines, trialkylphosphines or arsines. Preference is given to using dppf, PPh$_3$, P(t-Bu)$_3$, Pcy$_3$ or AsPh$_3$, particularly preferably dppf.

Suitable diluents for carrying out the processes (A), (B) and (C) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, tetrachloromethane, dichlorethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane. Particular preference is given to using acetone, dimethoxyethane, dioxane, tetrahydrofuran, dimethylformamide, dimethylacetamide, dimethyl sulphoxide, ethanol, toluene or, if appropriate, mixtures of the diluents mentioned with water.

Suitable diluents for carrying out the process (D) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichlorethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole. Particular preference is given to using dioxane, tetrahydrofuran or toluene.

Suitable acid binders for carrying out the processes (A), (B), (C) and (D) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, alkali metal fluorides, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to operate without additional acid binder, or to employ an excess of the amine component, so that it simultaneously acts as acid binder. Barium hydroxide, sodium hydroxide, potassium hydroxide, tripotassium phosphate, caesium carbonate, potassium carbonate, sodium carbonate, potassium acetate, triethylamine, potassium tert-butoxide, caesium fluoride or potassium fluoride are used with particular preference.

When carrying out the processes (A), (B) and (C) according to the invention, the reaction temperatures can in each case be varied within a relatively wide range. In general, the reactions are carried out at temperatures between 0° C. and 140° C., preferably between 20° C. and 120° C., particularly preferably between 60° C. and 100° C.

When carrying out the process (D) according to the invention, the reaction temperatures can in each case be varied within a relatively wide range. In general, the reaction is carried out at temperatures between 0° C. and 140° C., preferably between 20° C. and 120° C.

All processes according to the invention are generally carried out under atmospheric pressure. However, in each case it is also possible to operate under elevated or reduced pressure.

The active compounds according to the invention are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp.; *Psylliodes chrysocephala, Epilachna*

*varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus* siro, *Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

In particular, the compounds of the formula (I) according to the invention have excellent activity against caterpillars, beetle larvae, spider mites, aphids and leaf-mining flies.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds according to the invention can be converted into the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds according to the invention with extenders, that is liquid solvents and/or solid carriers, optionally with the use of surfactants, that is emulsifiers and/or dispersants and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks;

suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates;

suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used in customary commerical form or in their formulations as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly advantageous co-components are, for example, the following:

Fungicides:
aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberdazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB),
sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole,
validamycin A, vinclozolin, viniconazole, zarilamide, zineb, ziram and also Dagger G, OK-8705, OK-8801, α-(1,1-dimethylethyl)-β-(2-phenoxyethyl)-1H-1,2,4-triazole-1-ethanol, α-(2,4-dichlorophenyl)-β-fluoro-α-propyl-1H-1,2,4-triazole-1-ethanol, α-(2,4-dichlorophenyl)-β-methoxy-α-methyl-1H-1,2,4-triazole-1-ethanol, α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl {2-methyl-1-[[[1-(4-methylphenyl)-ethyl]-amino]-carbonyl]-propyl}carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran-3'-one Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopernethrin, BPMC, bromophos A, bufencarb, buprofezin, butathiofos, butocarboxim, butylpyridaben,
cadusafos, carbaryl, carbofuran, carbophenothion, carbosulphan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, *Entomopfthora* spp., eprinomectin, esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses,
halofenozide, HCH, heptenophos, hexaflumuron, hexythiazox, hydroprene,
imidacloprid, isazofos, isofenphos, isoxathion, ivermectin, nuclear polyhedrosis viruses,
lambda-cyhalothrin, lufenuron,
malathion, mecarbam, metaldehyde, methamidophos, *Metharhizium anisopliae, Metharhizium flavoviride,* methidathion, methiocarb, methomyl, methoxyfenozide, metolcarb, metoxadiazone, mevinphos, milbemectin, monocrotophos,
naled, nitenpyram, nithiazine, novaluron,
omethoate, oxamyl, oxydemethon M,
*Paecilomyces fumosoroseus,* parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, selamectin, silafluofen, spinosad, sulphotep, sulprofos,
tau-fluvalinate, tebufenozide, tebufenpyrad, tebupirimphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii,*
YI 5302,
zeta-cypermethrin, zolaprofos,
(1R-cis)-[5-(phenylmethyl)-3-furanyl]-methyl-3-[(dihydro-2-oxo-3(2H)furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate.
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]3(2H)-pyridazinone,
4-chloro-2-(2-chloro-2-methylpropyl)-5-[(6-iodo-3-pyridinyl)methoxy]-3(2H)pyridazinone,
4-chloro-5-[(6-chloro-3-pyridinyl)methoxy]-2-(3,4-dichlorophenyl)-3(2H)pyridazinone,

*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5] dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]4,5-dihydro-4-phenyl-1H-pyrazole-1-carboxamide,
N-[(2-chloro-5-thiazolyl)methyl]-N'-methyl-N''-nitroguanidine,
N-methyl-N'-(1–methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds according to the invention, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The preferred transgenic plants or plant cultivars (i.e. those obtained by genetic engineering) which are to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryRIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), Star-Link® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still to be developed genetic traits, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

They have, for example, excellent activity against the development stages of ticks such as, for example, *Amblyomma hebraeum*, against parasitic flies such as, for example, *Lucilia cuprina* and against fleas such as, for example, *Ctenocephalides felis*.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) according to the invention can be used as formulations (for example powders, emulsions, free-flowing compositions), which comprise the active compounds according to the invention in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning nonliving materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden window frames and doors, plywood, chipboard, joinery or wooden products which are used quite generally in house-building or in building joinery.

The active compounds according to the invention can be used as such, in the form of concentrates or in generally customary formulations, such as powders, granules, solutions, suspensions, emulsions or pastes.

The formulations mentioned can be prepared in a manner known per se, for example by mixing the active compounds according to the invention with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octylisothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as
benzo[b]thiophenecarboxylic acid cyclohexylamide S,S-dioxide, dichlofluanid, fluorfolpet, 3-iodo-2-propinyl butyl-carbamate, tolylfluanid and azoles such as azaconazole, cyproconazole, epoxyconazole, hexaconazole, metconazole, propiconazole and tebuconazole;

molluscicides such as
fentin acetate, metaldehyde, methiocarb, niclosamid, thiodicarb and trimethacarb; or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/-styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all development stages.

These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus* and *Dermatophagoides forinae*.

From the order of the Araneae, for example, *Aviculariidae* and *Araneidae*.

From the order of the Opiliones, for example, *Pseudoscorpiones chelifer, Pseudoscorpiones cheiridium* and *Opiliones phalangium*.

From the order of the Isopoda, for example, *Oniscus asellus* and *Porcellio scaber*.

From the order of the Diplopoda, for example, *Blaniulus guttulatus* and *Polydesmus* spp.

From the order of the Chilopoda, for example, *Geophilus* spp.

From the order of the Zygentoma, for example, *Ctenolepisma* spp., *Lepisma saccharina* and *Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa* and *Supella longipalpa*.

From the order of the Saltatoria, for example, *Acheta domesticus*.

From the order of the Dermaptera, for example, *Forficula auricularia*.

From the order of the Isoptera, for example, *Kalotermes* spp. and *Reticulitermes* spp.

From the order of the Psocoptera, for example, *Lepinatus* spp. and *Liposcelis* spp.

From the order of the Coleptera, for example, *Anthrenus* spp., *Attagenus* spp., *Dermestes* spp., *Latheticus oryzae*, *Necrobia* spp., *Ptinus* spp., *Rhizopertha dominica*, *Sitophilus granarius*, *Sitophilus oryzae*, *Sitophilus zeamais* and *Stegobium paniceum*.

From the order of the Diptera, for example, *Aedes aegypti*, *Aedes albopictus*, *Aedes taeniorhynchus*, *Anopheles* spp., *Calliphora erythrocephala*, *Chrysozona pluvialis*, *Culex quinquefasciatus*, *Culex pipiens*, *Culex tarsalis*, *Drosophila* spp., *Fannia canicularis*, *Musca domestica*, *Phlebotomus* spp., *Sarcophaga camaria*, *Simulium* spp., *Stomoxys calcitrans* and *Tipula paludosa*.

From the order of the Lepidoptera, for example, *Achroia grisella*, *Galleria mellonella*, *Plodia interpunctella*, *Tinea cloacella*, *Tinea pellionella* and *Tineola bisselliella*.

From the order of the Siphonaptera, for example, *Ctenocephalides canis*, *Ctenocephalides felis*, *Pulex irritans*, *Tunga penetrans* and *Xenopsylla cheopis*.

From the order of the Hymenoptera, for example, *Camponotus herculeanus*, *Lasius fuliginosus*, *Lasius niger*, *Lasius umbratus*, *Monomorium pharaonis*, *Paravespula* spp. and *Tetramorium caespitum*.

From the order of the Anoplura, for example, *Pediculus humanus capitis*, *Pediculus humanus corporis* and *Phthirus pubis*.

From the order of the Heteroptera, for example, *Cimex hemipterus*, *Cimex lectularius*, *Rhodinus prolixus* and *Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive evaporation systems, moth papers, moth bags and moth gels, as granules or dusts, in baits for spreading or in bait stations.

The preparation and use of the substances according to the invention is shown in the examples below.

PREPARATION EXAMPLES

Example 1

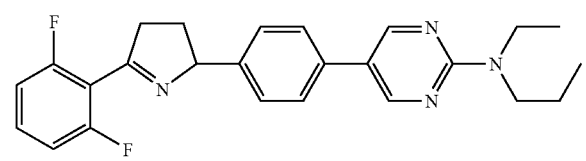

Process (A)

2-(4-Bromophenyl)-5-(2,6-difluorophenyl)-3,4-dihydro-2H-pyrrole (8.40 g, 0.025 mol), bis(pinacolato)diboron (7.60 g, 0.03 mol), potassium acetate (7.40 g, 0.075 mol), PdCl$_2$[dppf] (0.56 g, 75 mmol) and dimethylacetamide (150 ml) are stirred at 80° C. for 3 h. The reaction mixture is cooled to room temperature. N-(5-Bromo-2-pyrimidinyl)-N-ethyl-N-propylamine (6.30 g, 0.026 mol), PdCl$_2$[dppf] (0.56 g, 75 mmol) and 2 M aqueous sodium carbonate solution (75 ml) are then added, and the mixture is stirred at 80° C. for 16 h. The reaction mixture is cooled to room temperature, diluted with water and filtered off with suction through Celite. The filter cake is washed with ethyl acetate. The organic phase is washed with water, dried over sodium sulphate and filtered. Florisil (60 g) is added, and the solvent is removed under reduced pressure. The crude product is purified by silica gel chromatography (mobile phase: n-hexane/ethyl acetate, 4:1, v/v).

This gives 5.10 g (57% of theory) of N-(5-{4-[5-(2,6-difluorophenyl)-3,4-dihydro-2H-pyrrol-2-yl]phenyl}-2-pyrimidinyl)-N-ethyl-N-propylamine.

HPLC: log P (pH 2.3)=3.57 (purity: 99%) m.p. 88–89° C.

Example 2

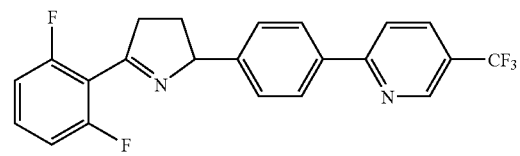

Process (A)

4-[5-(2,6-Difluorophenyl)-3,4-dihydro-2H-pyrrol-2-yl] phenyltrifluoromethanesulphonate (10.10 g, 0.025 mol), bis(pinacolato)diboron (7.60 g, 0.03 mol), potassium acetate (7.40 g, 0.075 mol), PdCl$_2$[dppf] (0.56 g, 75 mmol) and dimethylacetamide (150 ml) are stirred at 80° C. for 3 h. The reaction mixture is cooled to room temperature. 2-Bromo-5-trifluoromethylpyridine (4.72 g, 0.026 mol), PdCl$_2$[dppf] (0.56, 75 mmol) and 2 M aqueous sodium carbonate solution (75 ml) are then added, and the mixture is stirred at 80° C. for 16 h. The reaction mixture is cooled to room temperature and diluted with water, and the precipitate is filtered off with suction. This solid residue is taken up in ethyl acetate, washed with water, dried over sodium sulphate and filtered. Florisil (60 g) is added, and the solvent is removed under reduced pressure. The crude product is purified by silica gel chromatography (mobile phase: n-hexane/ethyl acetate, 4:1, v/v).

This gives 7.10 g (71% of theory) of 2-{(4-[5-(2,6-difluorophenyl)-3,4-dihydro-2H-pyrrol-2-yl]phenyl}-5-(trifluoromethyl)pyridine.

HPLC: log P (pH 2.3)=3.25 (purity: 97.90%) m.p. 125° C.

Example 3

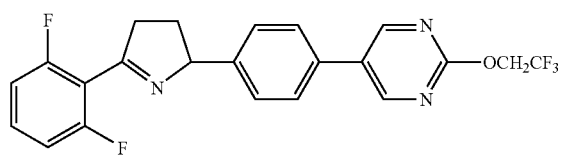

Process (B)

5-(2,6-Difluorophenyl)-2-[4-(4,4,5,5-tetramethyl-1,3,2-dioxaborolan-2-yl)phenyl]3,4-dihydro-2H-pyrrole (0.96 g, 2.50 mmol) is initially charged in dimethoxyethane (15 ml). 5-Bromo-2-(2,2,2-trifluoroethoxy)pyrimidine (0.71 g, 2.75 mmol), PdCl$_2$[dppf] (56 mg, 0.075 mmol) and aqueous saturated sodium carbonate solution (3.75 ml) are added successively, and the reaction mixture is heated at 80° C. for 16 hours. After cooling to room temperature, water and ethyl acetate are added to the reaction mixture. The organic phase is separated off and dried over sodium sulphate, filtered and concentrated under reduced pressure. The crude product is purified by silica gel chromatography (mobile phase: n-hexane/ethyl acetate 9:1→3:1, in each case v/v).

This gives 0.71 g (64% of theory) of 5-{4-[5-(2,6-difluorophenyl)-3,4-dihydro-2H-pyrrol-2-yl]phenyl}-2-(2,2,2-trifluorethoxy)pyrimidine.

HPLC: log P (pH 2.3)=2.88 (purity: 98%) m.p. 112–114° C.

The compounds listed in the table below can be prepared analogously using one of the processes (A), (B), (C) or (D).

| No. | Structure | m.p. (° C.) | log P (pH 2.3) |
|---|---|---|---|
| 4 | 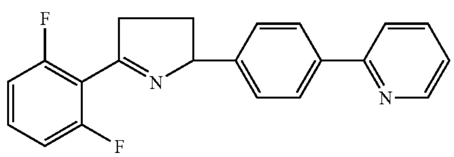 | oil | 1.24 |
| 5 | 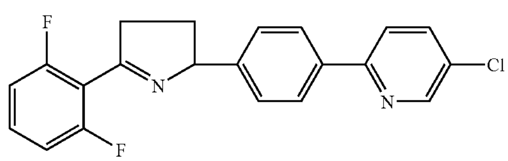 | 119–121 | 2.86 |
| 6 | 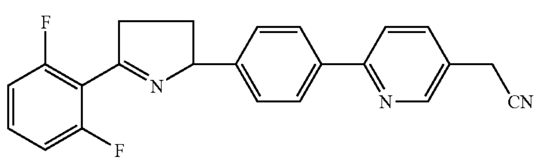 | 120–127 | 1.74 |
| 7 | 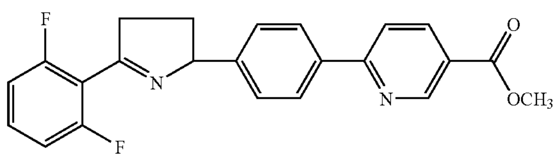 | oil | 2.39 |
| 8 | 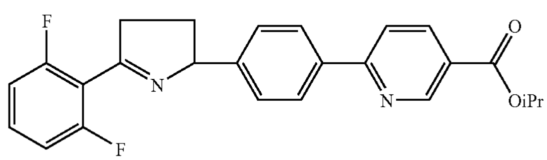 | oil | 3.89 |
| 9 | 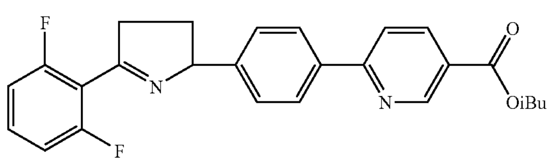 | 115–119 | 3.28 |
| 10 | 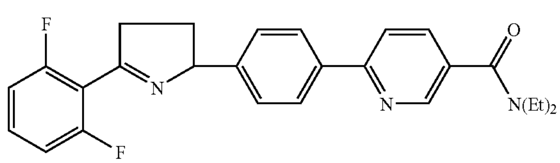 | oil | 2.02 |

-continued

| No. | Structure | m.p. (° C.) | log P (pH 2.3) |
|---|---|---|---|
| 11 | 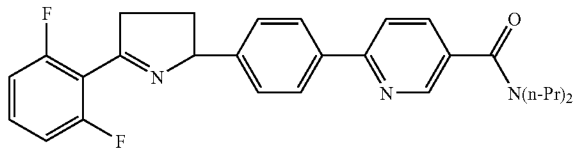 | oil | 2.70 |
| 12 | 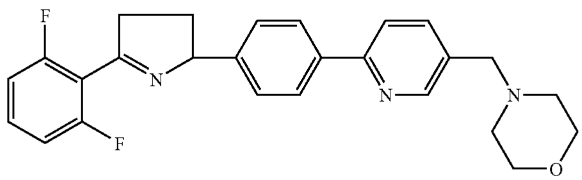 | | |
| 13 | 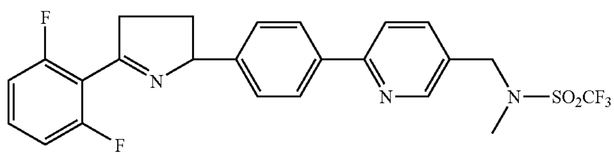 | | 3.06 |
| 14 | 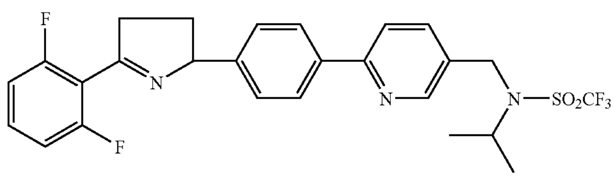 | oil | 3.48 |
| 15 | 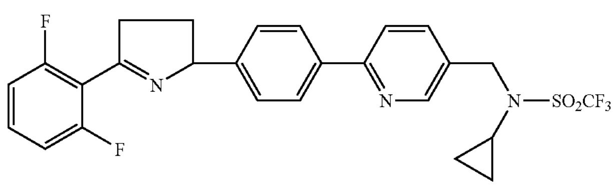 | | 3.39 |
| 16 | 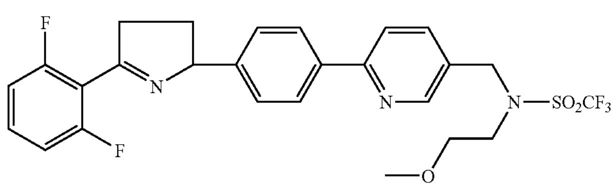 | | 3.21 |
| 17 | 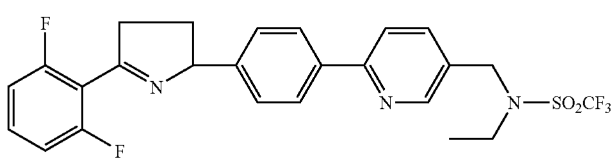 | | 3.35 |
| 18 | 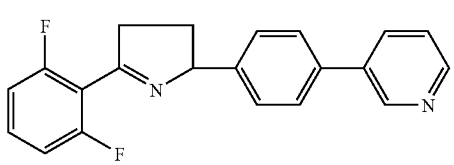 | 85–89 | 1.12 |
| 19 | 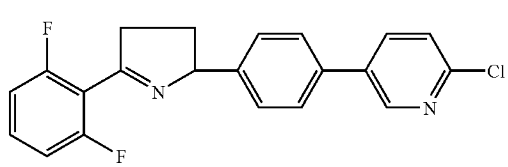 | 158 | 2.58 |

-continued

| No. | Structure | m.p. (°C.) | log P (pH 2.3) |
|---|---|---|---|
| 20 | 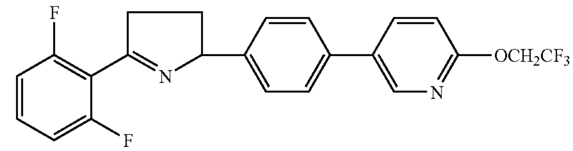 | 86–90 | 3.66 |
| 21 | 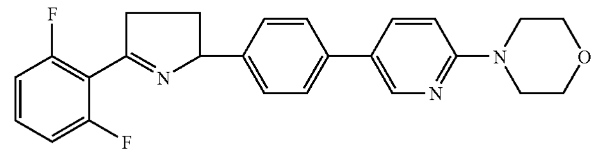 | 140–142 | 1.44 |
| 22 | 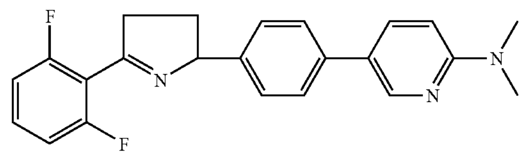 | | |
| 23 | 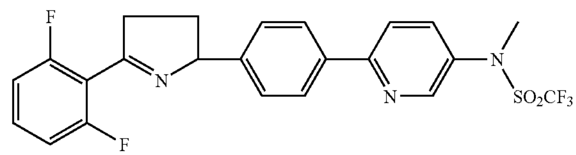 | | 2.63 |
| 24 | 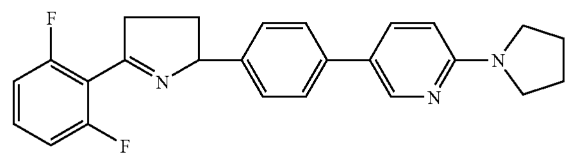 | | 1.45 |
| 25 | [α]$_D^{20}$ = +34.1 (c = 0.42, methanol) | 120–123 | |
| 26 | 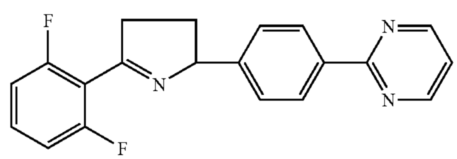 | | 1.79 |
| 27 | 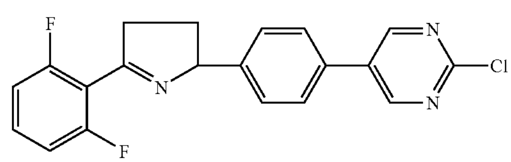 | 195–198 | 1.98 |
| 28 | 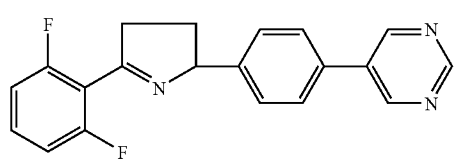 | 133–134 | 1.49 |

-continued
| No. | Structure | m.p. (° C.) | log P (pH 2.3) |
|---|---|---|---|
| 29 | 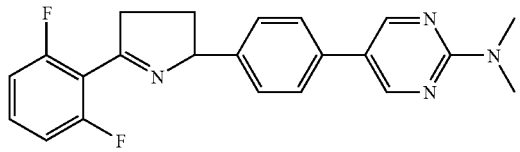 | 127–130 | 3.62 |
| 30 | 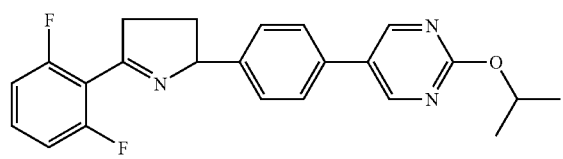 | 109 | 2.61 |
| 31 | 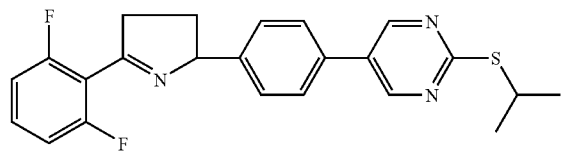 | 132 | 3.49 |
| 32 | 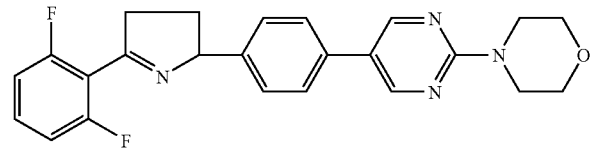 | 178 | 2.18 |
| 33 | 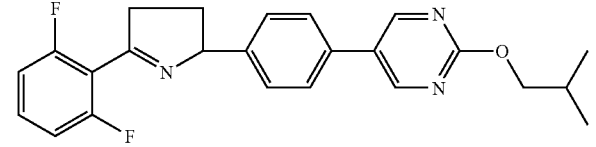 | 109–111 | 3.22 |
| 34 | 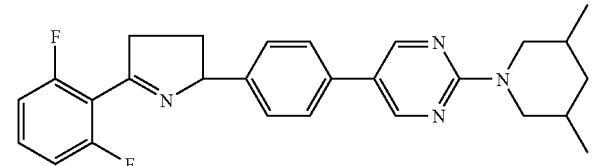 | 139–142 | 4.39 |
| 35 | 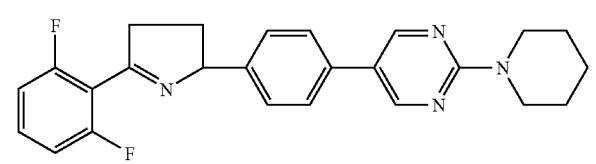 | 108–112 | 3.40 |
| 36 | 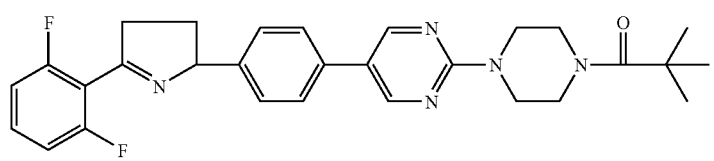 | 192–194 | 2.81 |
| 37 | 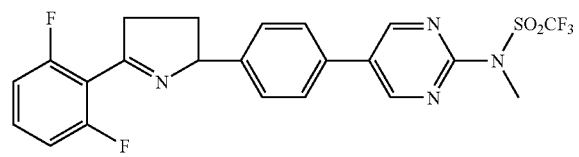 | | 3.50 |

-continued

| No. | Structure | m.p. (° C.) | log P (pH 2.3) |
|---|---|---|---|
| 38 | 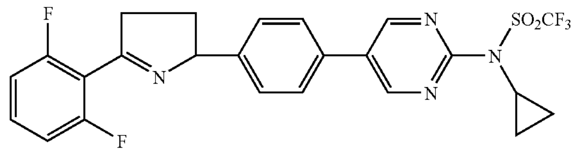 | | 3.63 |
| 39 | 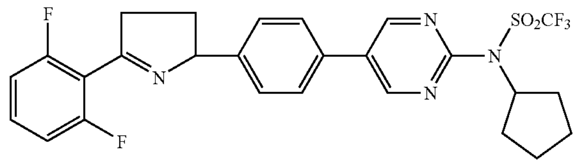 | | |
| 40 | 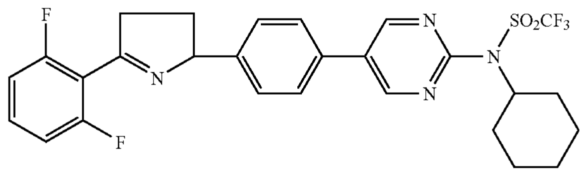 | | |
| 41 | 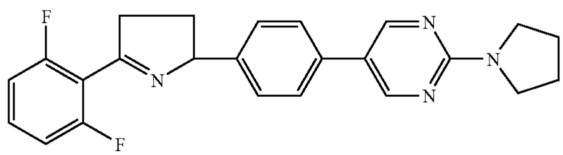 | | 2.11 |
| 42 | 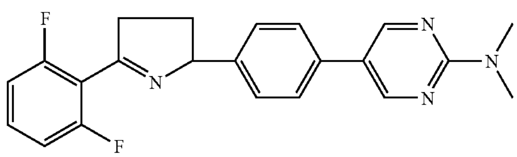 | | 2.40 |
| 43 | 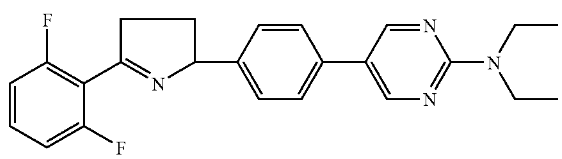 | | 3.00 |
| 44 | [α]$_D^{20}$ = +38.6 (c = 0.39, methanol) | 132 | |
| 45 | 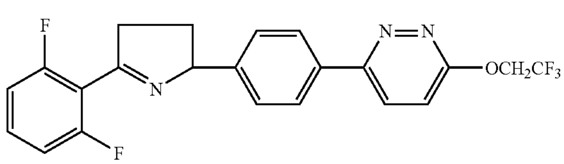 | 126 | 3.77 |
| 46 | 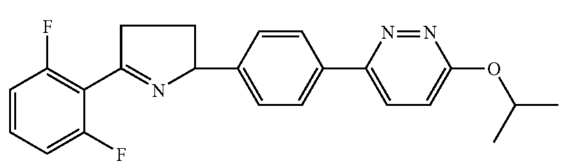 | | 2.50 |

-continued

| No. | Structure | m.p. (° C.) | log P (pH 2.3) |
|---|---|---|---|
| 47 | 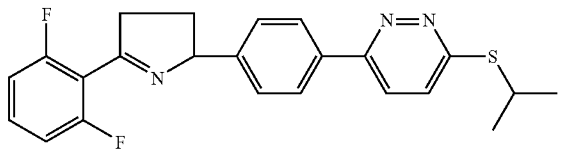 | 110–112 | 2.94 |
| 48 | 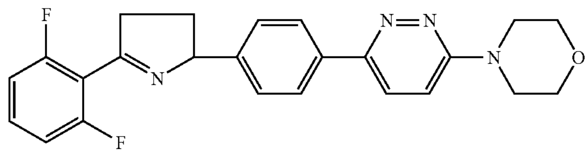 | 174 | 1.19 |
| 49 | 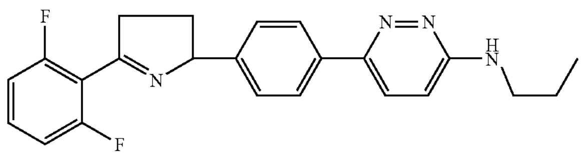 | 149 | 1.26 |
| 50 | 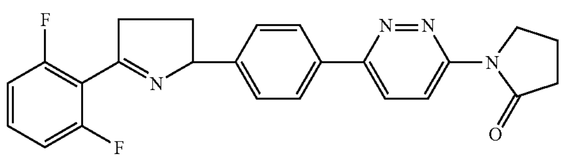 | 173 | 1.85 |
| 51 | 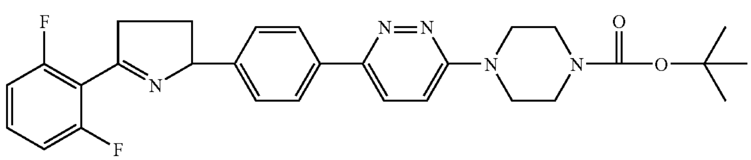 | 152–155 | 2.07 |
| 52 | 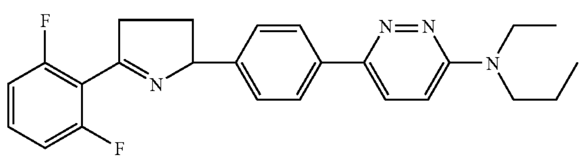 | oil | 1.60 |
| 53 | 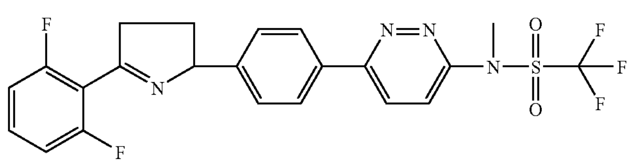 | 123–127 | 1.66 |
| 54 | 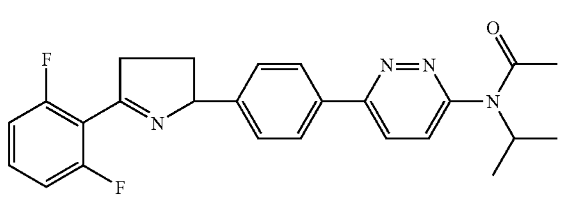 | oil | 2.03 |
| 55 | 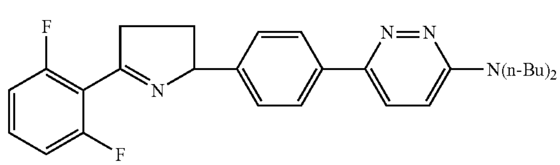 | oil | 2.56 |

-continued

| No. | Structure | m.p. (° C.) | log P (pH 2.3) |
|---|---|---|---|
| 56 | 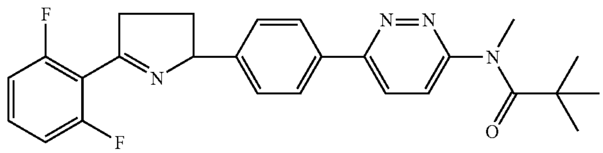 | 169–171 | 2.29 |
| 57 | 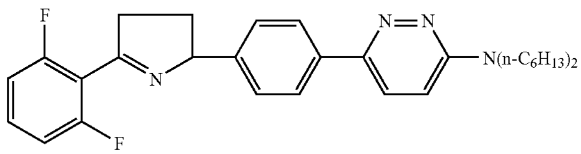 | oil | 3.71 |
| 58 | 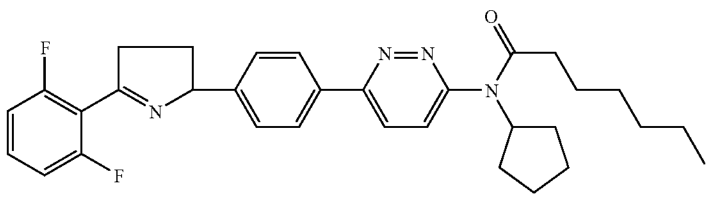 | oil | 4.82 |
| 59 | 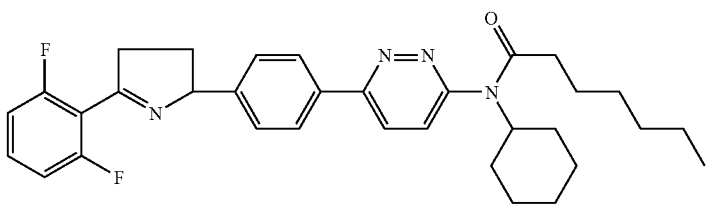 | oil | 4.35 |
| 60 | 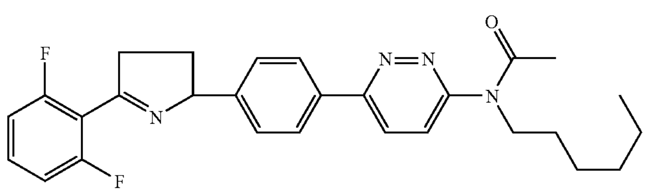 | oil | 3.11 |
| 61 | 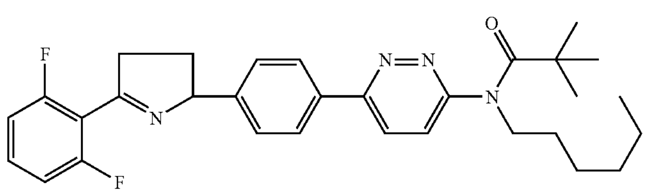 | 97–101 | 4.35 |
| 62 | 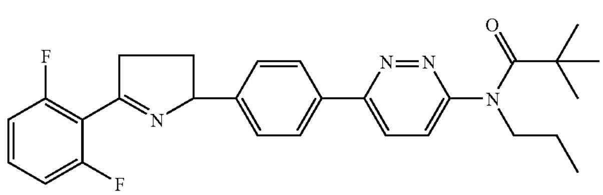 | oil | 2.95 |
| 63 | 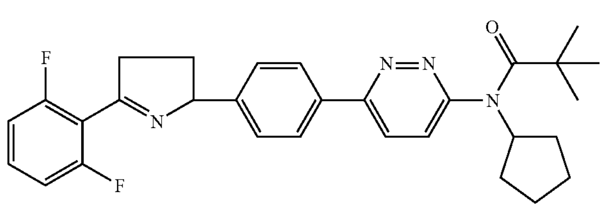 | 134–138 | 3.22 |

| No. | Structure | m.p. (° C.) | log P (pH 2.3) |
|---|---|---|---|
| 64 | 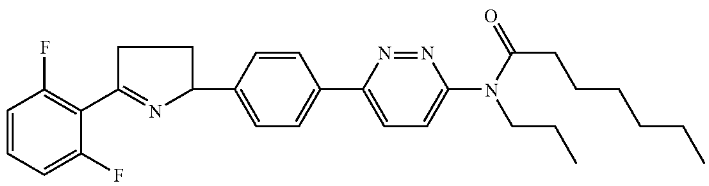 | | 3.89 |
| 65 | 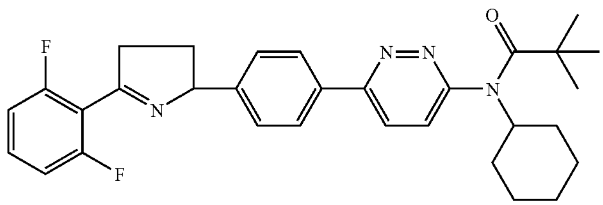 | oil | 3.56 |
| 66 | 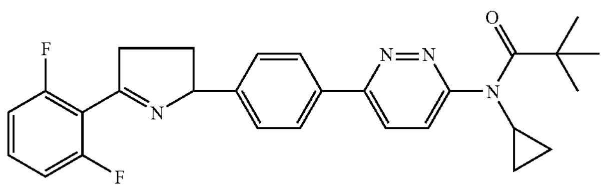 | 179–181 | 2.53 |
| 67 | 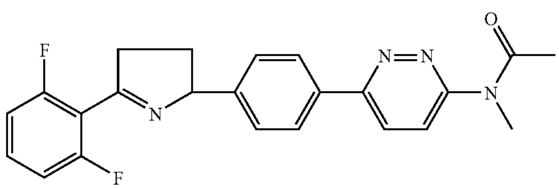 | 87–91 | 1.48 |
| 68 | 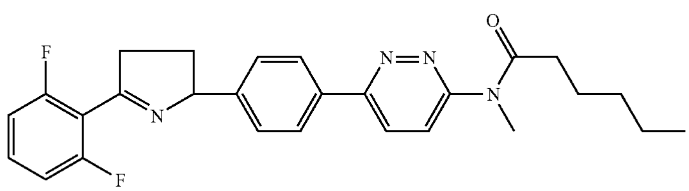 | 91–95 | 3.24 |
| 69 | 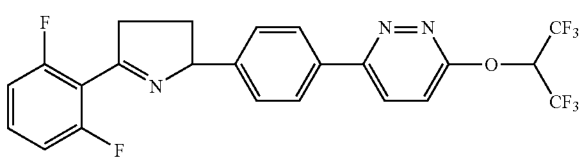 | 70–76 | 3.70 |
| 70 | 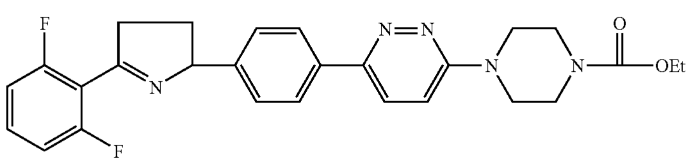 | oil | 1.63 |
| 71 | 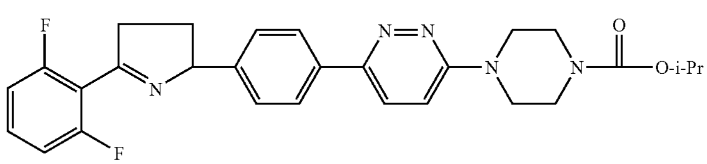 | | 1.91 |

| No. | Structure | m.p. (° C.) | log P (pH 2.3) |
|---|---|---|---|
| 72 | 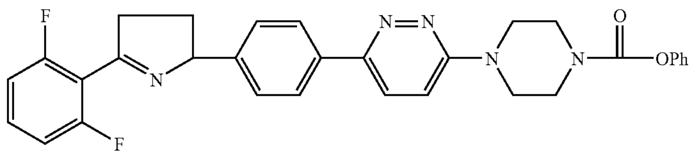 | | |
| 73 | 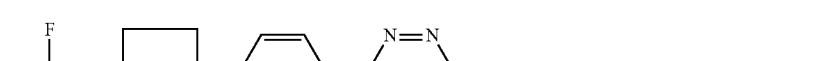 | | 3.58 |
| 74 | 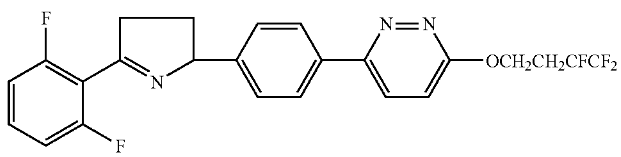 | | 2.95 |
| 75 | 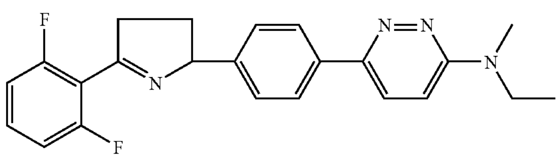 | | 1.23 |
| 76 | 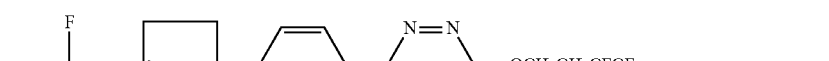 | | |
| 77 | 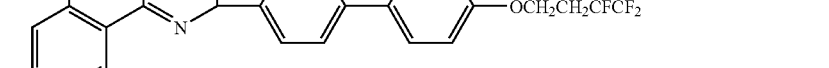 | | 1.82 |
| 78 | 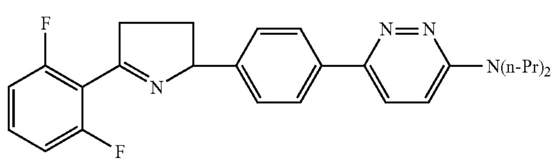 | | 1.86 |
| 79 | 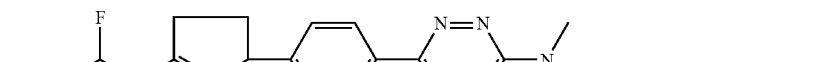 | | 1.08 |
| 80 | 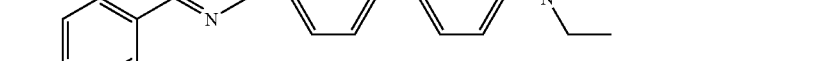 | | 1.39 |

-continued

| No. | Structure | m.p. (°C.) | log P (pH 2.3) |
|---|---|---|---|
| 81 | 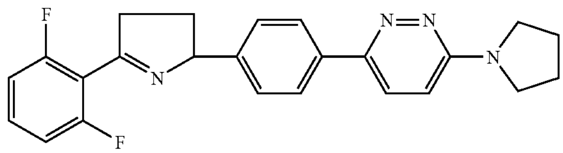 | | 1.28 |
| 82 | 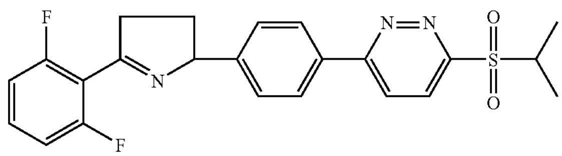 | | 1.40 |
| 83 | 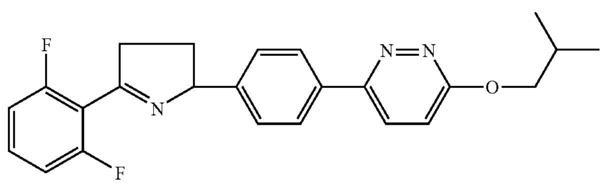 | | |
| 84 | 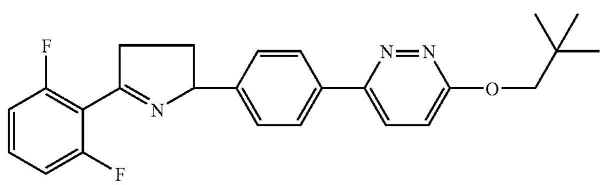 | | |
| 85 | 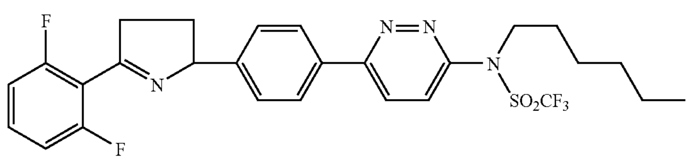 | | |
| 86 | 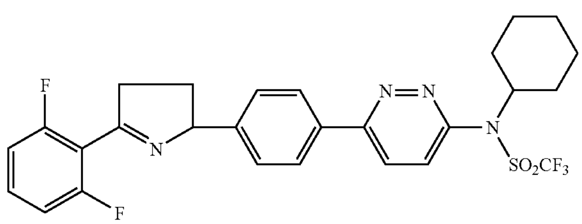 | | |
| 87 | 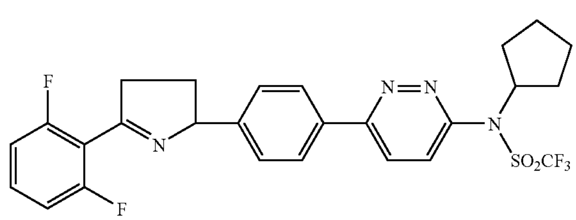 | | |
| 88 | 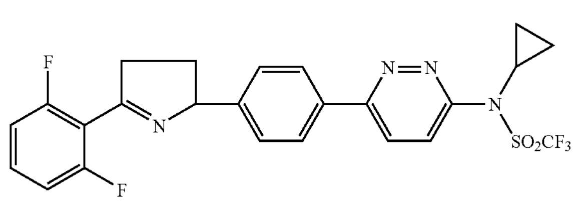 | | |

-continued

| No. | Structure | m.p. (° C.) | log P (pH 2.3) |
|-----|-----------|-------------|----------------|
| 89  | 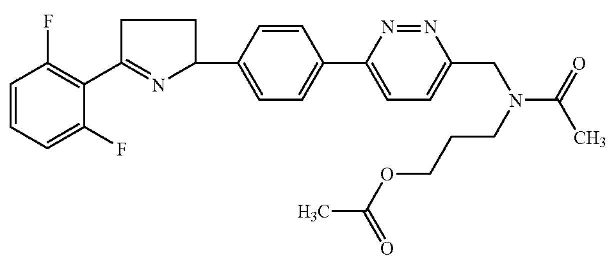          | oil         | 1.77           |
| 90  | 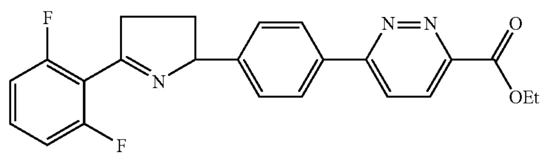          |             |                |
| 91  | 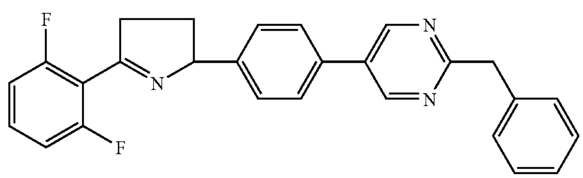          | 122–126     | 2.79           |
| 92  | 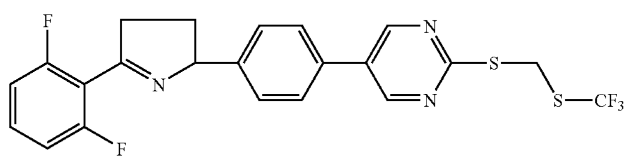          |             | 4.00           |
| 93  | 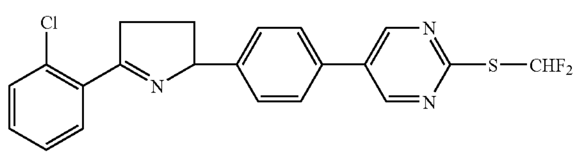          |             | 3.38           |
| 94  | 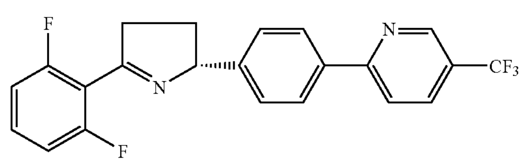          |             | 3.28           |
| 95  | 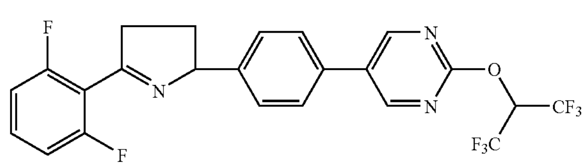          |             | 3.85           |
| 96  | 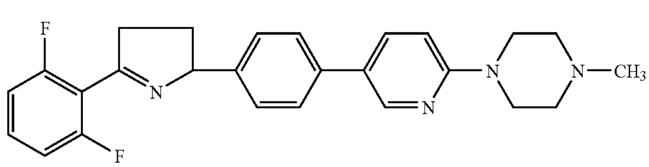          |             | 1.04           |

-continued

| No. | Structure | m.p. (° C.) | log P (pH 2.3) |
|---|---|---|---|
| 97 | 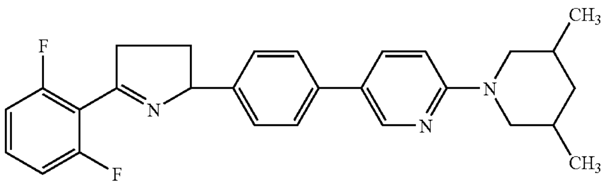 | | 2.10 |
| 98 | 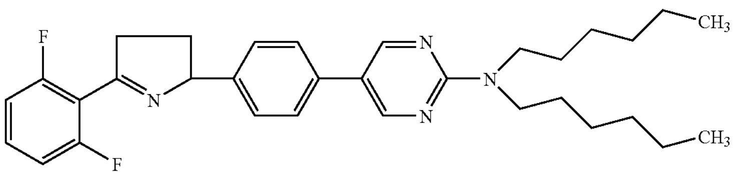 | | |
| 99 | 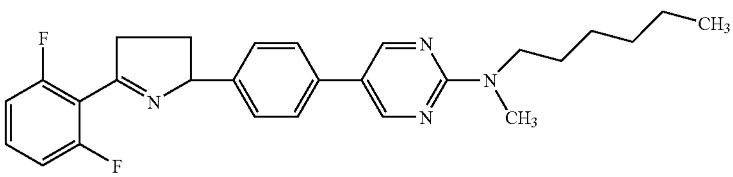 | | 4.94 |
| 100 | 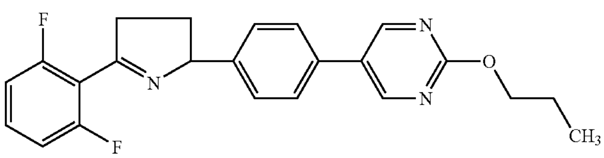 | | 2.72 |
| 101 | 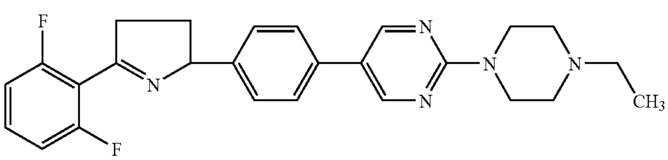 | | 1.24 |
| 102 | 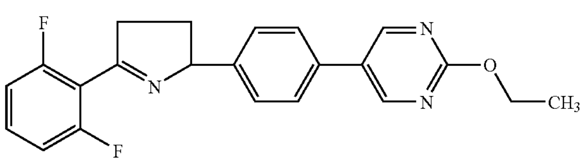 | | 2.21 |
| 103 | 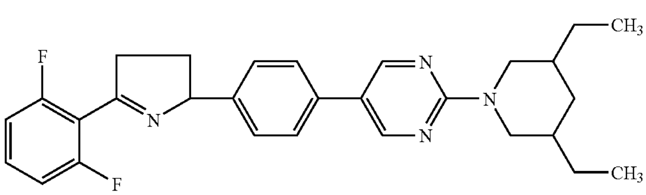 | | 5.82 |
| 104 | 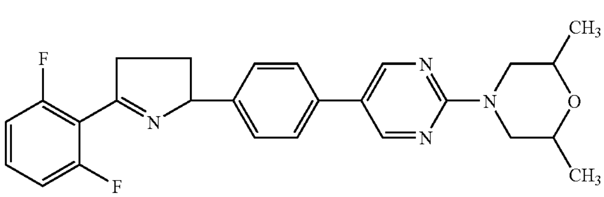 | | 3.00 |

-continued

| No. | Structure | m.p. (°C.) | log P (pH 2.3) |
|---|---|---|---|
| 105 | 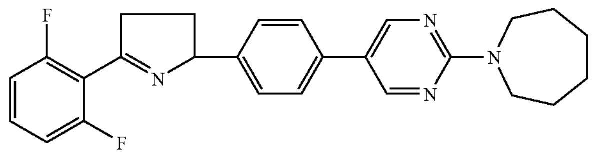 | | 3.41 |
| 106 | 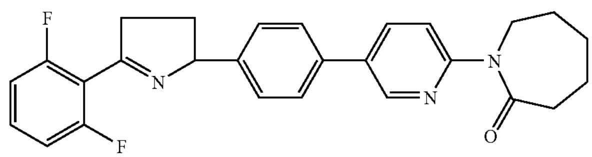 | | 2.25 |
| 107 | 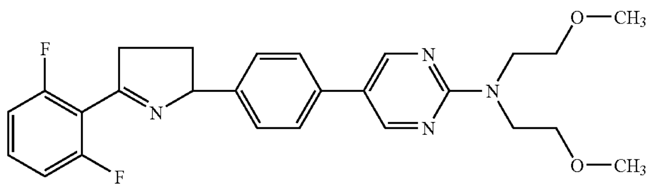 | | 2.48 |
| 108 | 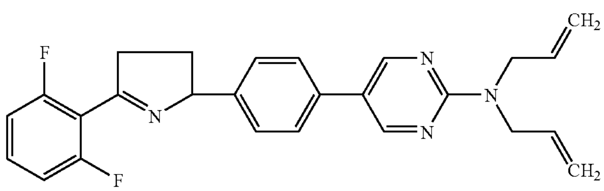 | | 3.74 |
| 109 | 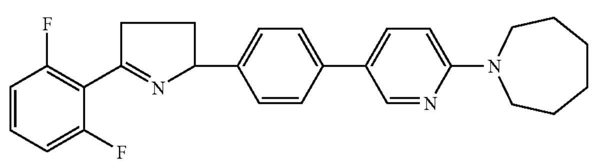 | | 1.65 |
| 110 | 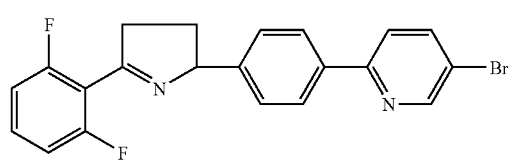 | | 3.07 |
| 111 | 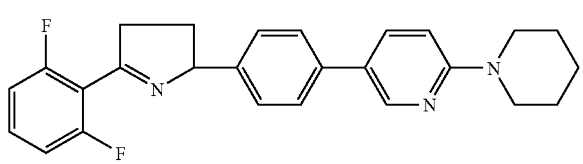 | | 1.49 |
| 112 | 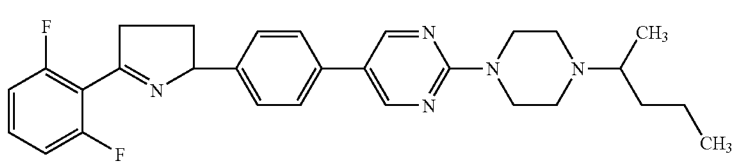 | | 1.65 |
| 113 | 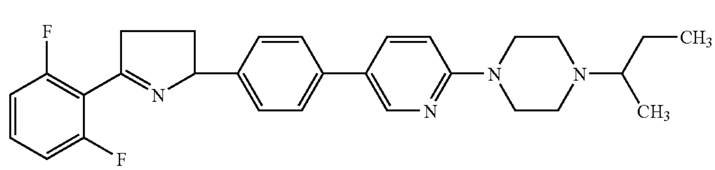 | | 1.30 |

-continued
| No. | Structure | m.p. (° C.) | log P (pH 2.3) |
|---|---|---|---|
| 114 | 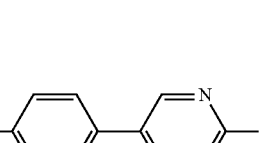 | | 1.28 |
| 115 | 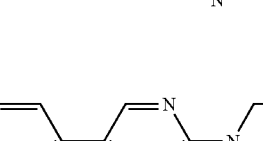 | | 2.29 |
| 116 | 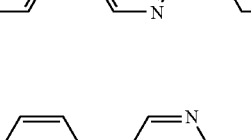 | | 3.88 |
| 117 | 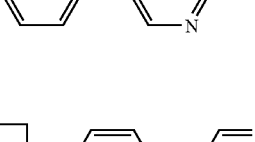 | | 2.70 |
| 118 | 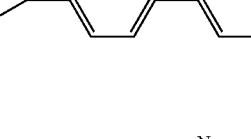 | | 1.55 |
| 119 | 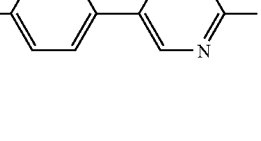 | | 5.47 |
| 120 | 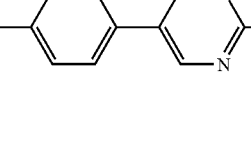 | | 4.38 |
| 121 | 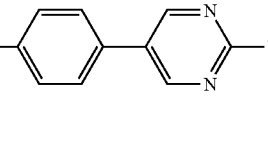 | | 4.58 |
| 122 | 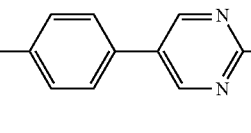 | | 3.84 |

-continued
| No. | Structure | m.p. (° C.) | log P (pH 2.3) |
|---|---|---|---|
| 123 | 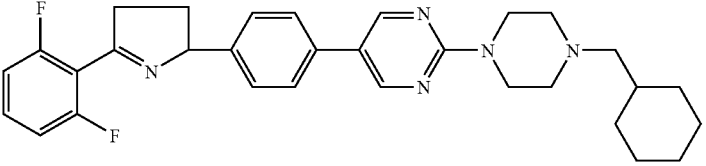 | | 2.12 |
| 124 | 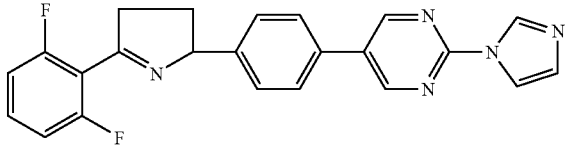 | | 1.25 |
| 125 | 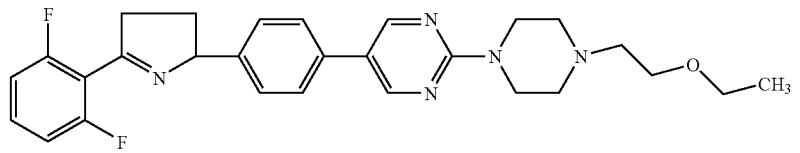 | | 1.47 |
| 126 | 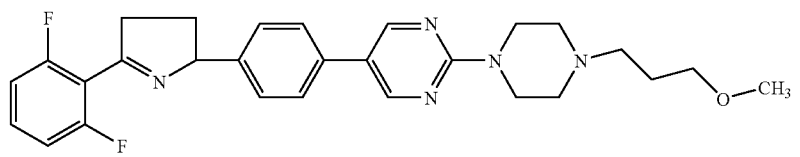 | | 1.38 |
| 127 | 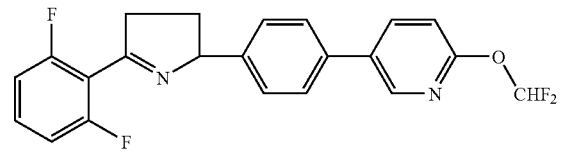 | | 3.13 |
| 128 | 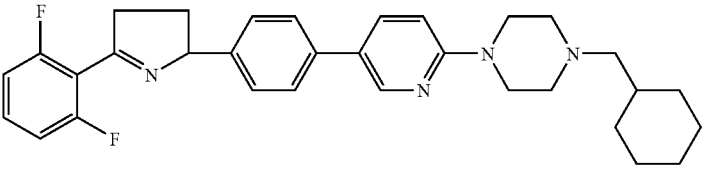 | | 6.70 |
| 129 | 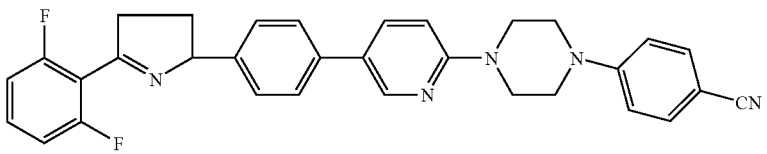 | | 2.29 |
| 130 | 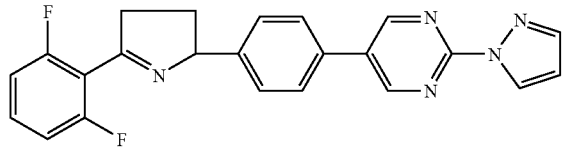 | | 1.98 |
| 131 | 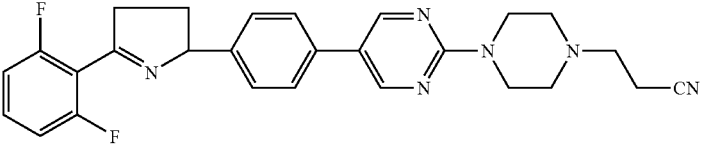 | | 1.69 |

-continued

| No. | Structure | m.p. (° C.) | log P (pH 2.3) |
|---|---|---|---|
| 132 | 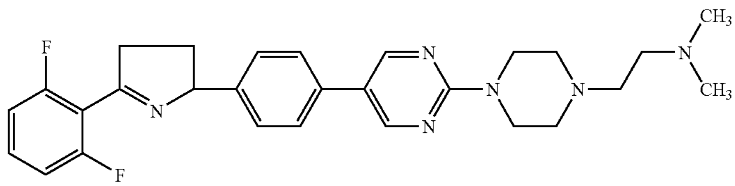 | | 3.00 |
| 133 | 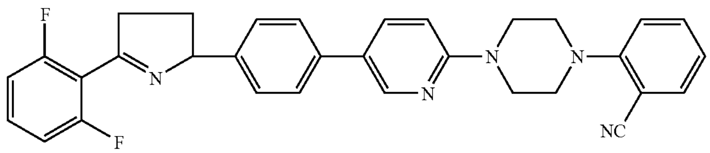 | | 2.30 |
| 134 | 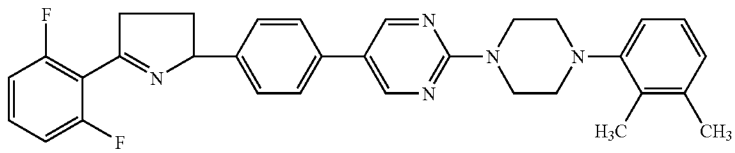 | | 5.78 |
| 135 | 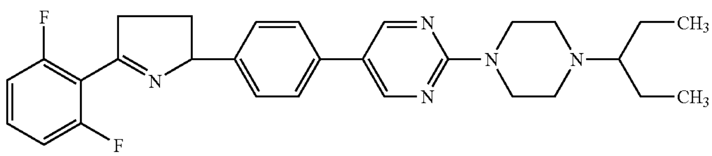 | | 2.13 |
| 136 | 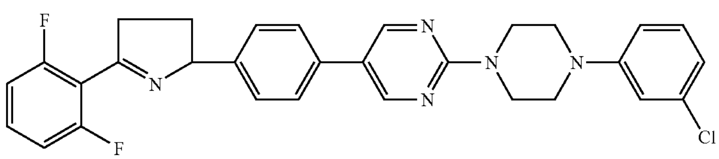 | | 4.83 |
| 137 | 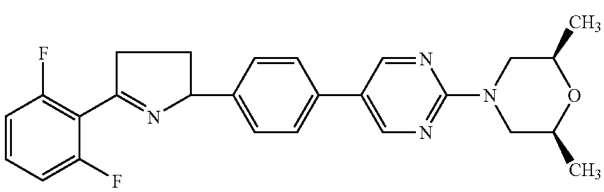 | | 3.03 |
| 138 | 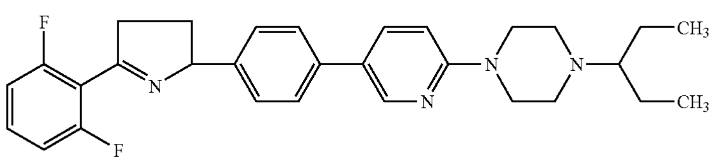 | | 1.39 |
| 139 | 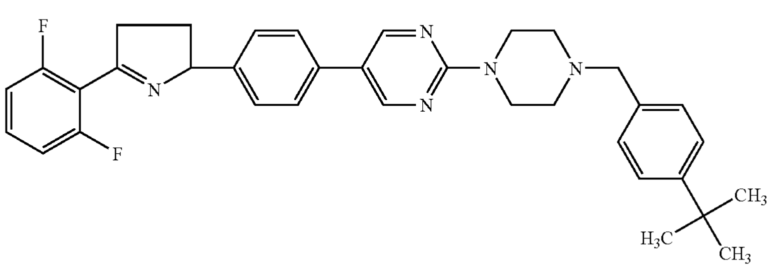 | | 3.30 |

-continued

| No. | Structure | m.p. (° C.) | log P (pH 2.3) |
|---|---|---|---|
| 140 | 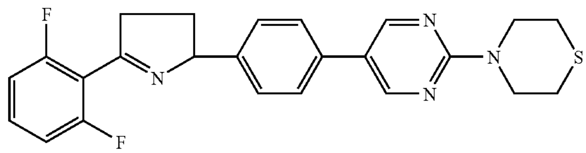 | | 3.13 |
| 141 | 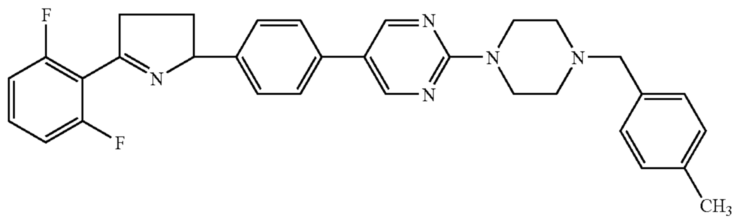 | | 2.28 |
| 142 | 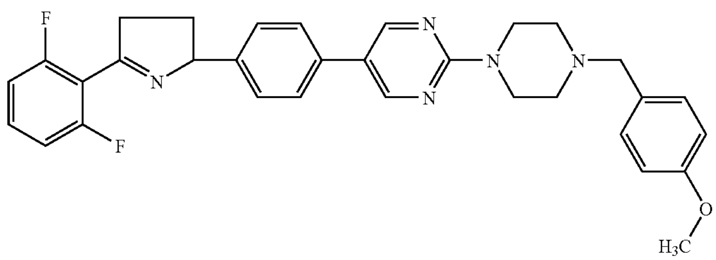 | | 2.22 |
| 143 | 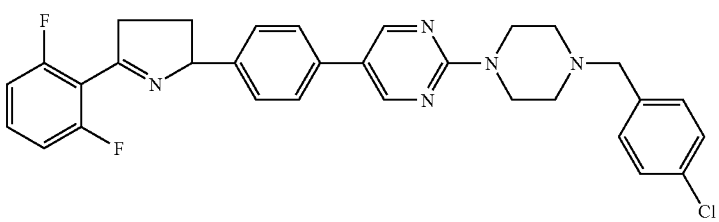 | | 2.25 |
| 144 | 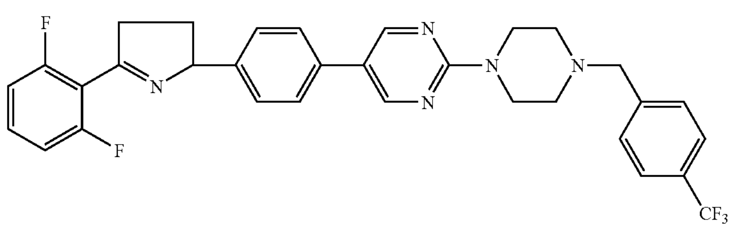 | | 4.70 |
| 145 | 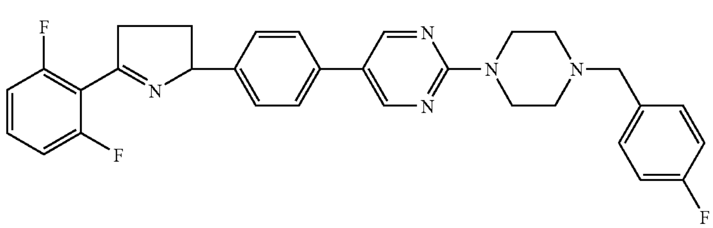 | | 1.78 |
| 146 | 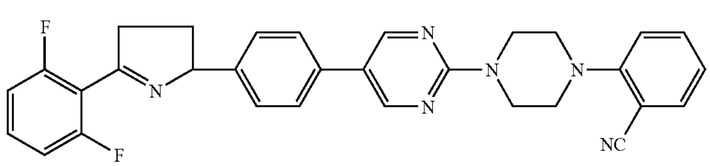 | | 3.78 |

-continued

| No. | Structure | m.p. (° C.) | log P (pH 2.3) |
|---|---|---|---|
| 147 | 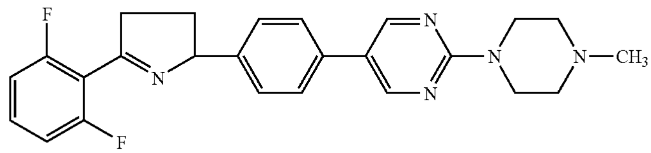 | | 1.48 |
| 148 | 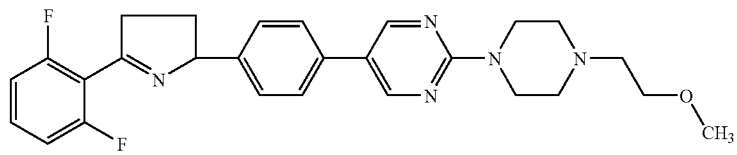 | | 1.49 |
| 149 | 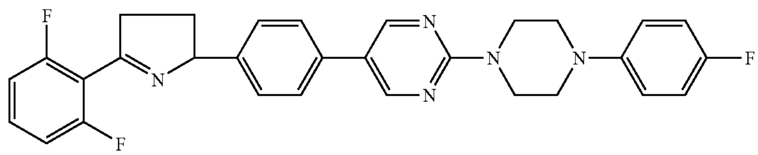 | | 3.95 |
| 150 | 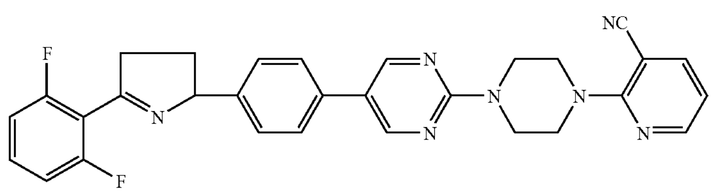 | | 3.28 |
| 151 | 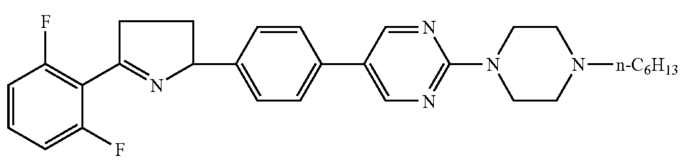 | | 2.40 |
| 152 | 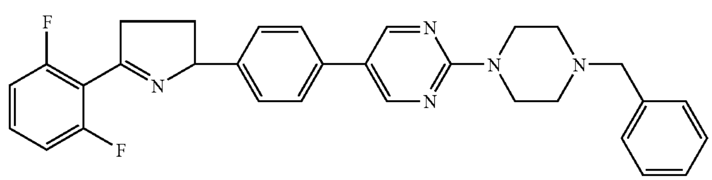 | | 1.92 |
| 153 | 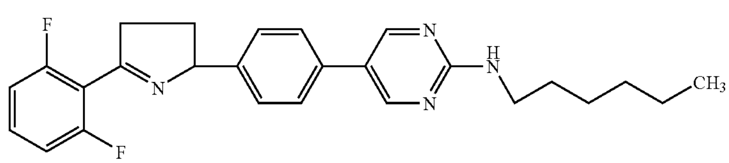 | | 3.10 |
| 154 | 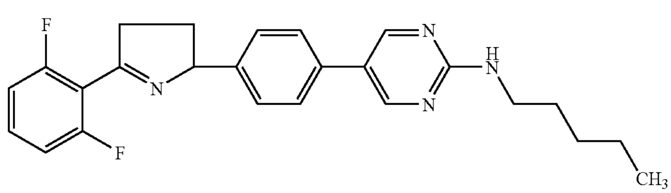 | | 2.90 |
| 155 | 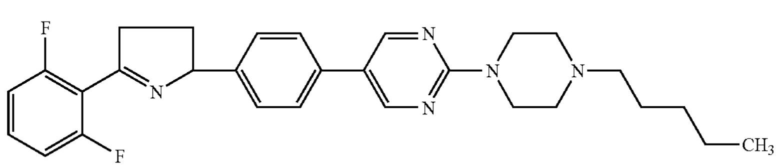 | | 2.02 |

-continued

| No. | Structure | m.p. (° C.) | log P (pH 2.3) |
|---|---|---|---|
| 156 | 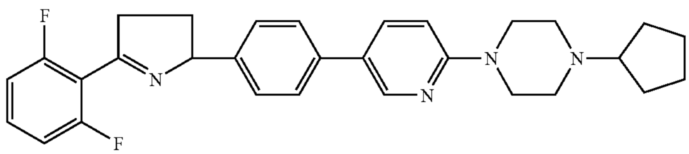 | | |
| 157 | 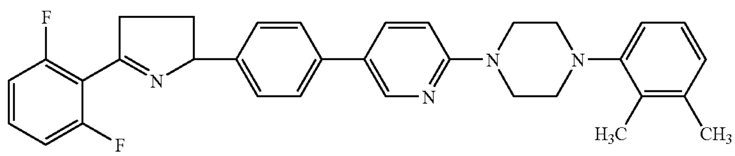 | | 3.63 |
| 158 | 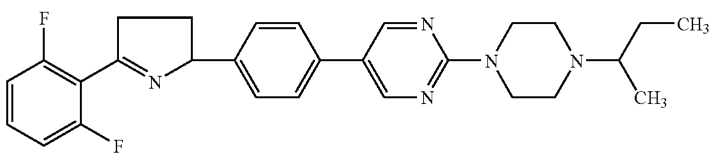 | | 1.65 |
| 159 | 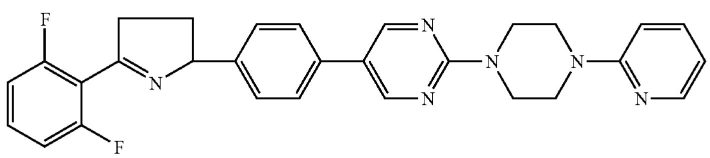 | | 2.06 |
| 160 | 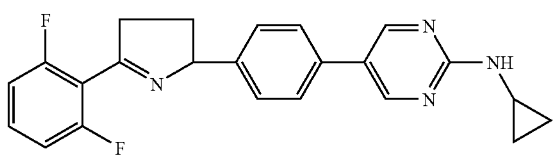 | | 1.65 |
| 161 | 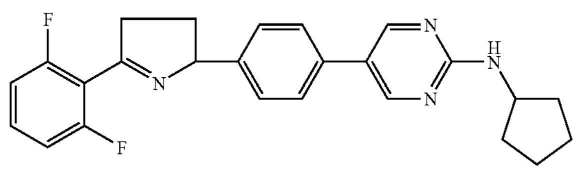 | | 2.58 |
| 162 | 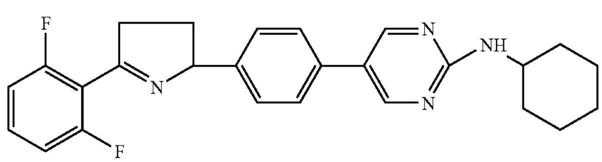 | | 3.00 |
| 163 | 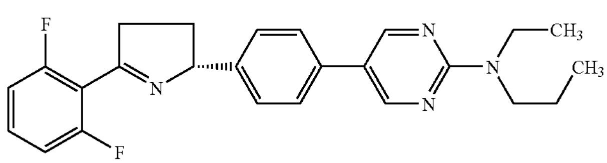 | 98–99 | 3.58 |
| 164 | 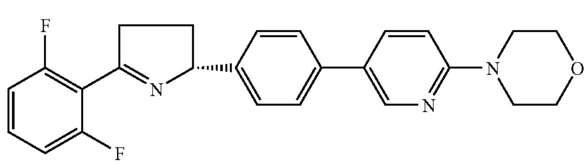 | 149–150 | 1.27 |

-continued
| No. | Structure | m.p. (° C.) | log P (pH 2.3) |
|---|---|---|---|
| 165 | 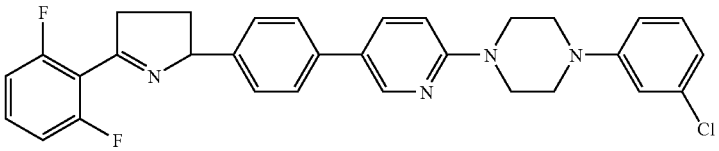 | | 3.17 |
| 166 | 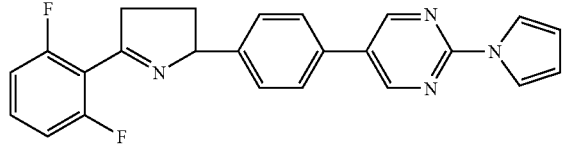 | | 3.58 |
| 167 | 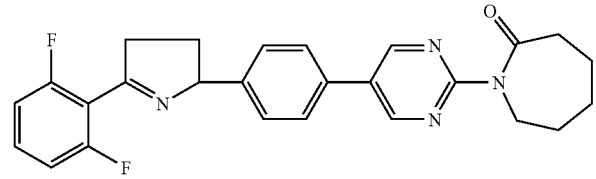 | | 1.89 |
| 168 | 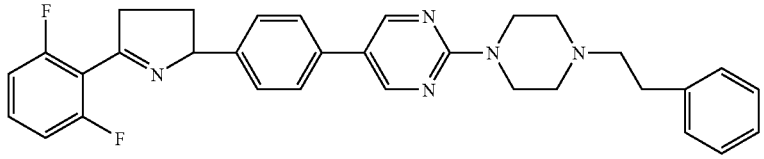 | | 1.84 |
| 169 | 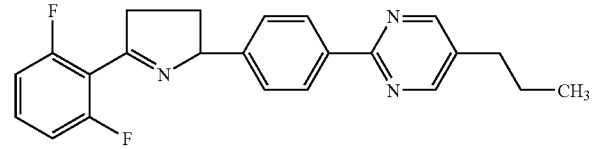 | | 2.96 |
| 170 | 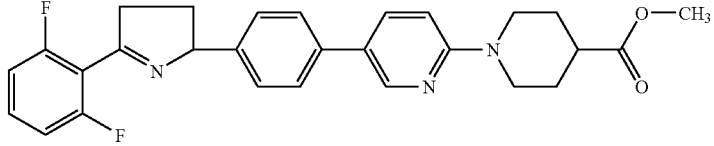 | | 1.61 |
| 171 | 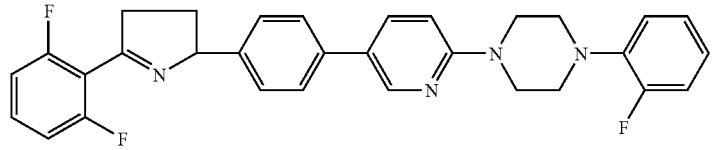 | | 2.51 |
| 172 | 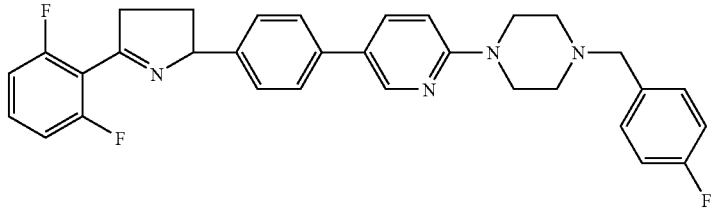 | | 1.64 |

-continued

| No. | Structure | m.p. (° C.) | log P (pH 2.3) |
|---|---|---|---|
| 173 | 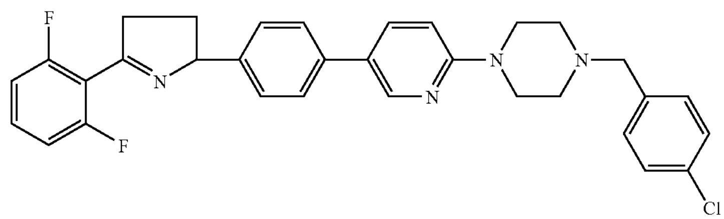 | | 1.83 |
| 174 | 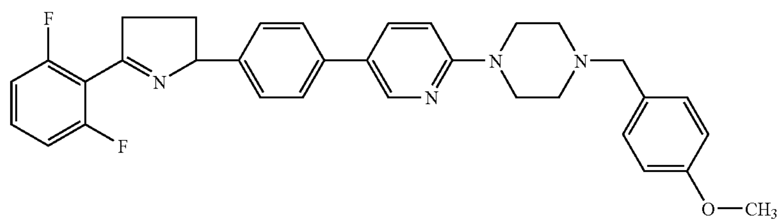 | | 1.59 |
| 175 | 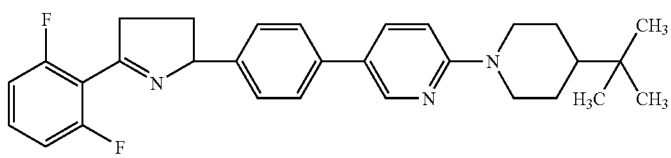 | | 2.89 |
| 176 | 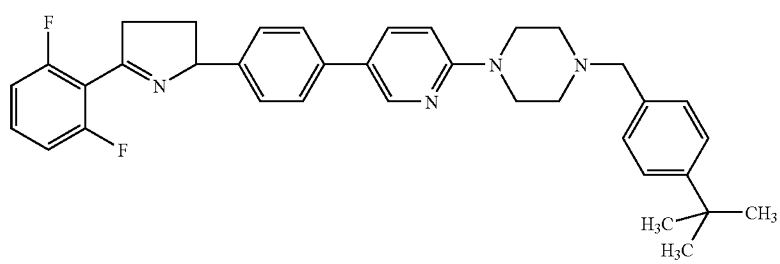 | | 2.23 |
| 177 | 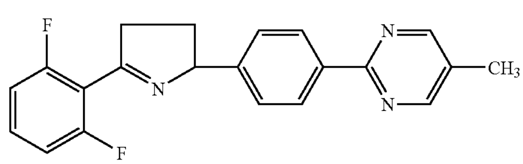 | | 2.02 |
| 178 | 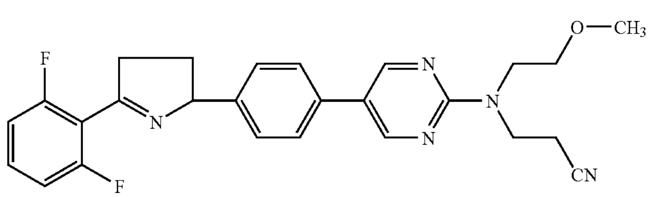 | | 2.45 |
| 179 | 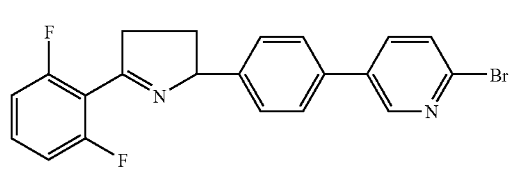 | | 2.69 |

-continued
| No. | Structure | m.p. (° C.) | log P (pH 2.3) |
|---|---|---|---|
| 180 | 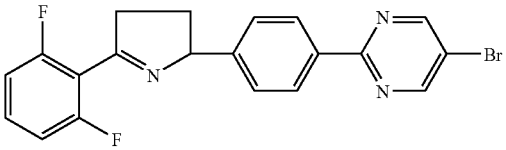 | | 3.08 |
| 181 | 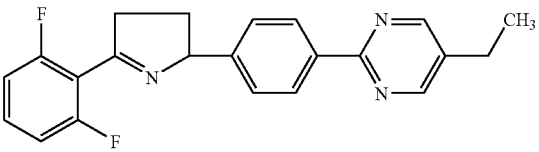 | | 2.46 |
| 182 | 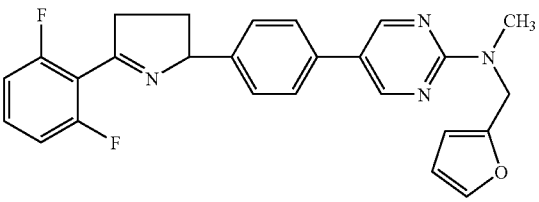 | | 3.10 |
| 183 | 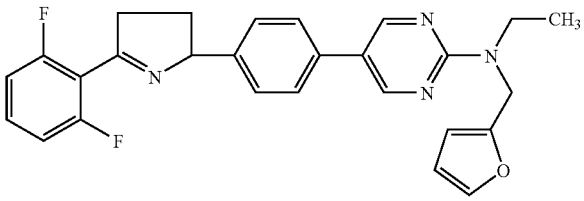 | | 3.59 |
| 184 | 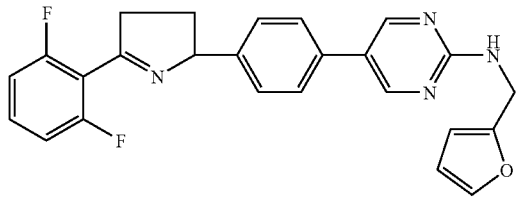 | | 2.31 |
| 185 | 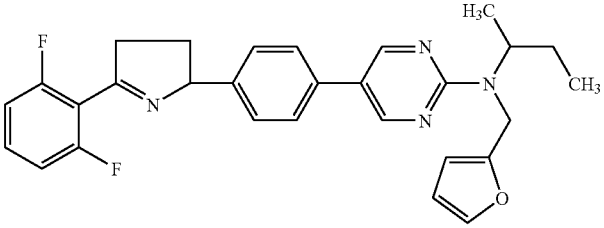 | | 4.54 |
| 186 | 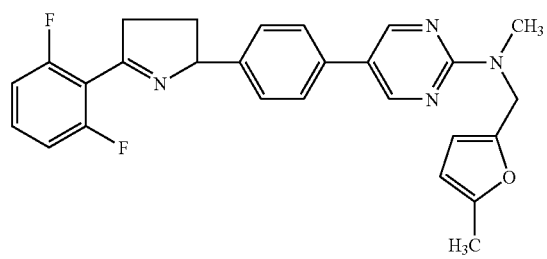 | | 3.40 |

-continued

| No. | Structure | m.p. (° C.) | log P (pH 2.3) |
|---|---|---|---|
| 187 | 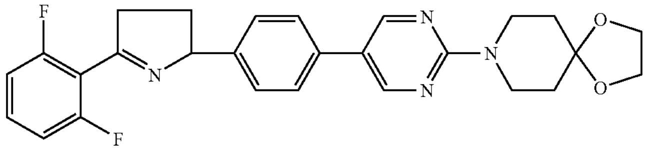 | | 2.51 |
| 188 | 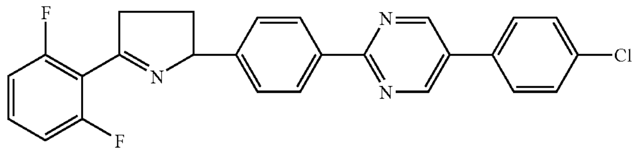 | | 4.12 |
| 189 | 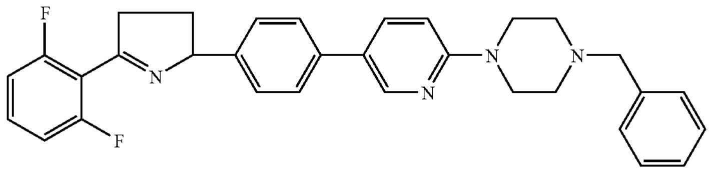 | | 1.50 |
| 190 | 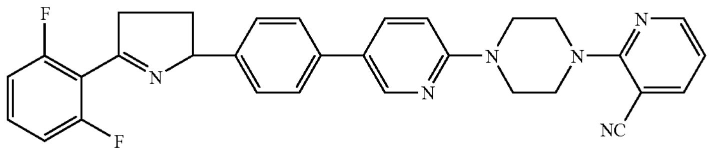 | | 3.09 |
| 191 | 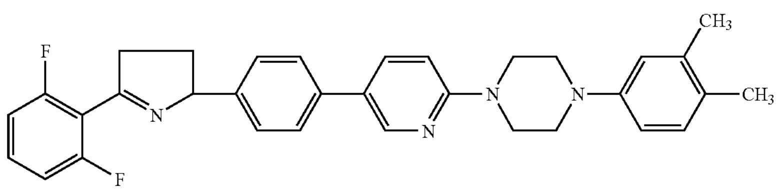 | | 2.58 |
| 192 | 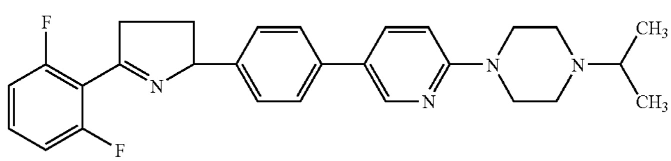 | | 1.14 |
| 193 | 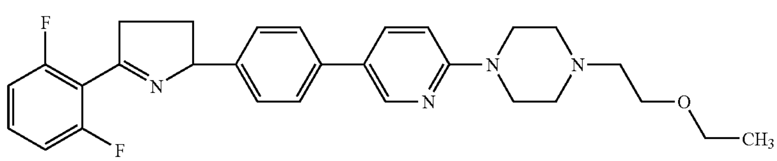 | | 1.26 |
| 194 | 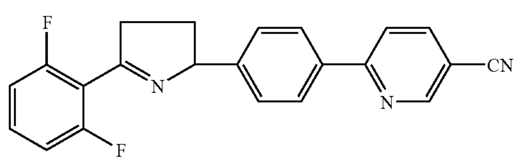 | | |
| 195 | 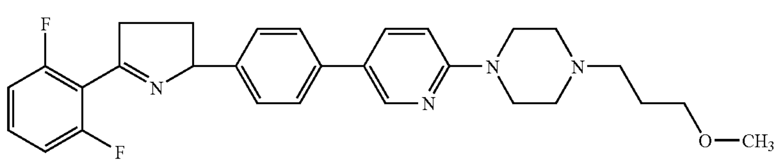 | | 1.16 |

-continued

| No. | Structure | m.p. (° C.) | log P (pH 2.3) |
|---|---|---|---|
| 196 | 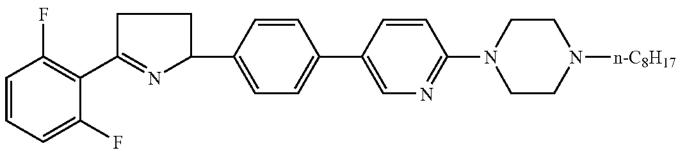 | | 2.28 |
| 197 | 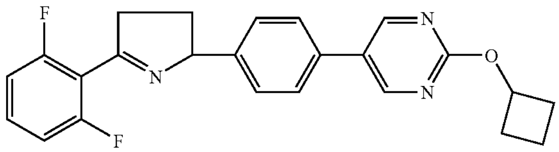 | | 2.88 |
| 198 | 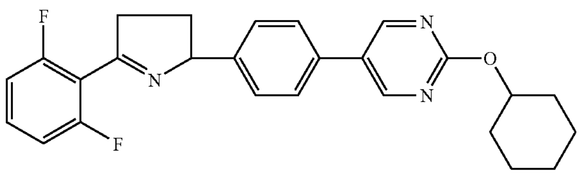 | | 3.67 |
| 199 | 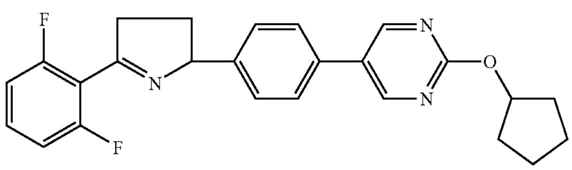 | | 3.21 |
| 200 | 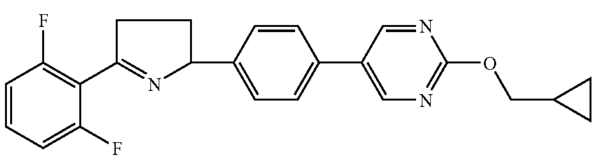 | | 2.74 |
| 201 | 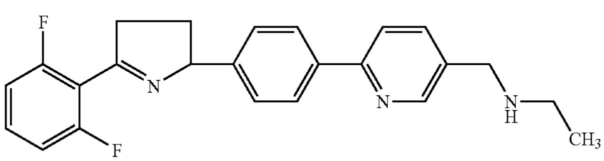 | | 0.90 |
| 202 | 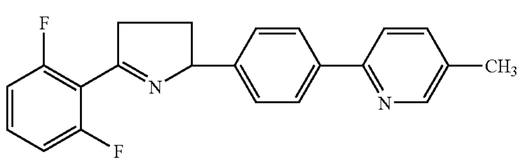 | | 1.24 |
| 203 | 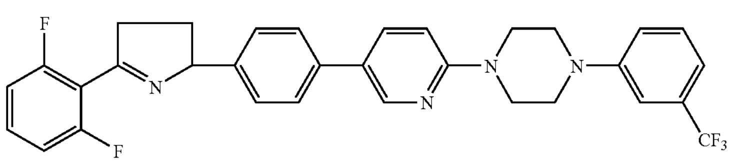 | | 3.00 |
| 204 | 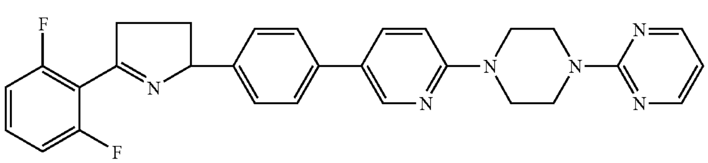 | | 1.50 |

-continued

| No. | Structure | m.p. (° C.) | log P (pH 2.3) |
|---|---|---|---|
| 205 | 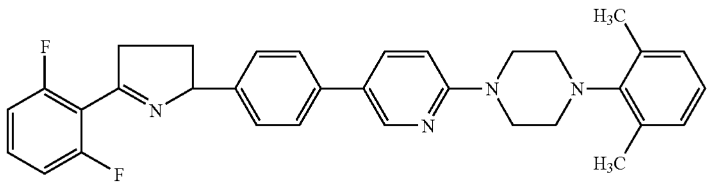 | | 3.76 |
| 206 | 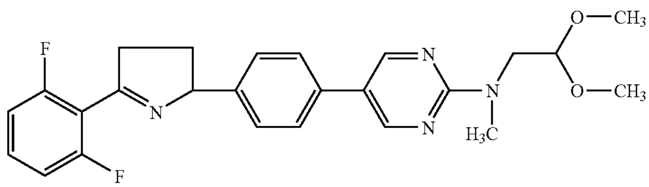 | | 2.32 |
| 207 | 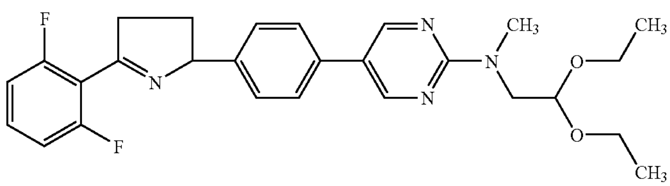 | | 3.09 |
| 208 | 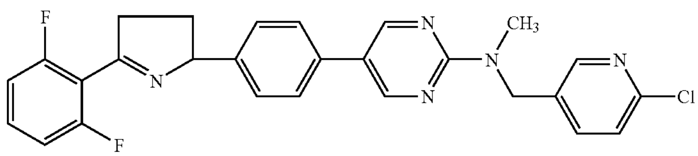 | | 2.89 |
| 209 | 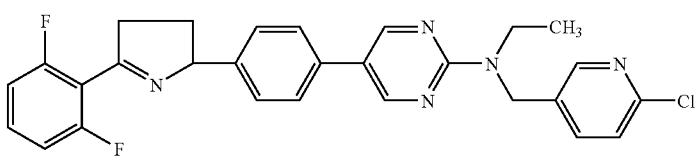 | | 3.60 |
| 210 | 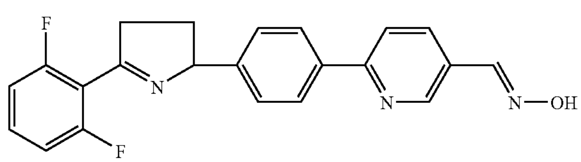 | | 1.58 |
| 211 | 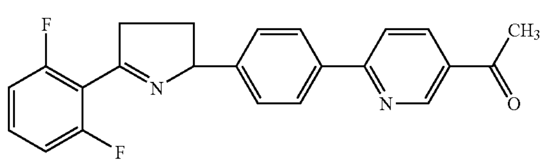 | | 2.00 |
| 212 | 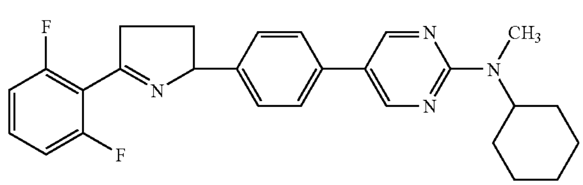 | | 4.11 |

-continued
| No. | Structure | m.p. (° C.) | log P (pH 2.3) |
|---|---|---|---|
| 213 | 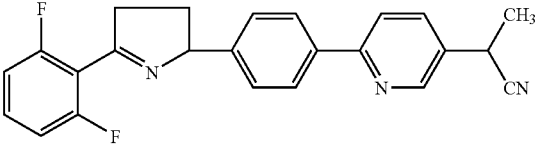 | | 1.98 |
| 214 | 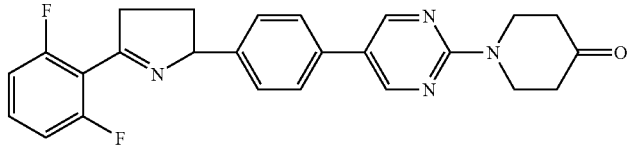 | | 2.00 |
| 215 | 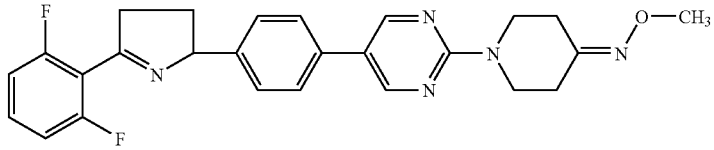 | | 2.65 |
| 216 | 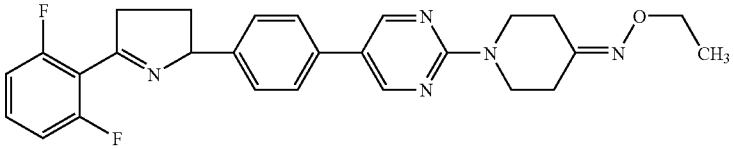 | | 3.10 |
| 217 | 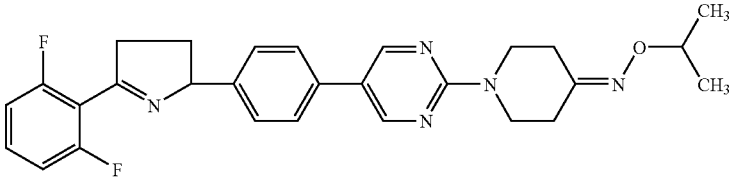 | | 3.83 |
| 218 | 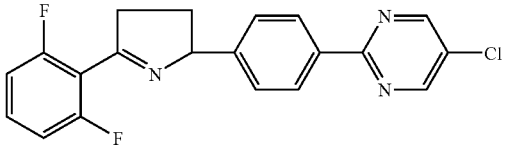 | | 2.87 |
| 219 | 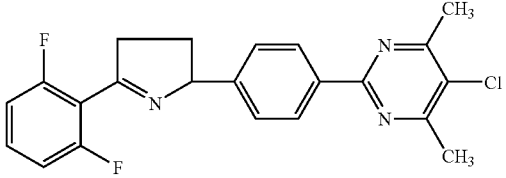 | | 3.90 |
| 220 | 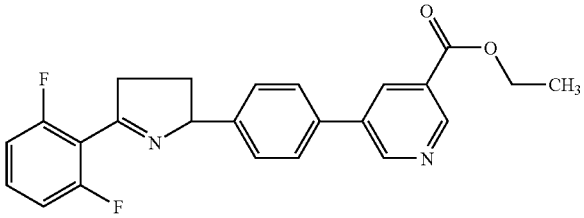 | | 2.42 |

| No. | Structure | m.p. (° C.) | log P (pH 2.3) |
|---|---|---|---|
| 221 | ![structure] | | 1.95 |

Preparation of Starting Materials of the Formula (III)

Example III-1

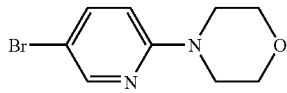

2,5-Dibromopyridine (50.00 g, 0.21 mol) and morpholine (38.62 g, 0.44 mmol) in toluene (300 ml) are heated at reflux for 24 hours. After cooling, the reaction mixture is concentrated and the residue is taken up in dichloromethane. The organic solution is washed with water, dried over magnesium sulphate, filtered and concentrated. The crude product is purified by silica gel chromatography (mobile phase: cyclohexane/ethyl acetate 10:1, v/v).

This gives 23.65 g (46% of theory) of 4-(5-bromo-2-pyridinyl)morpholine.

HPLC: log P (pH 2.3)=1.63 (purity: 100%) m.p. 65–68° C.

Example III-2

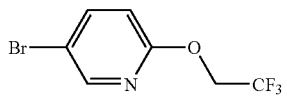

Under argon, sodium hydride (0.75 g, 18.64 mmol) is initially charged in DMF (50 ml) at 10° C., and 2,2,2-trifluoroethanol (1.71 g, 17.09 mmol) is added dropwise. The reaction mixture is then stirred at 10° C. for another hour. 2,5-Dibromopyridine (3.68 g, 15.53 mmol) is added a little at a time, and the reaction mixture is stirred at room temperature for another 16 hours. Water is added carefully, and the reaction mixture is extracted with ethyl acetate. The organic phase is dried over magnesium sulphate, filtered and concentrated.

This gives 3.15 g (69% of theory) of 5-bromo-2-(2,2,2-trifluoroethoxy)pyridine.

HPLC: log P (pH 2.3)=3.48 (purity: 87%)

Example III-3

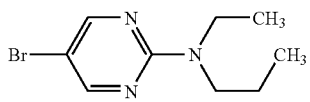

N-Ethyl-N-propylamine (4.80 g, 0.05 mol) is initially charged in acetonitrile (200 ml). After addition of potassium carbonate (7.60 g, 0.055 mol), the reaction mixture is stirred at room temperature for another hour. 5-Bromo-2-chloropyrimidine (9.67 g, 0.055 mol) is added, and the reaction mixture is stirred at reflux for another 16 hours. After cooling, the reaction mixture is stirred into water (500 ml) and then extracted with ethyl acetate (2×300 ml). The organic phase is dried over sodium sulphate, filtered and concentrated.

This gives 12.20 g (99% of theory) of N-(5-bromo-2-pyrimidinyl)-N-ethyl-N-propylamine.

HPLC: log P (pH 2.3)=4.38 (purity: 95%)

Example III-4

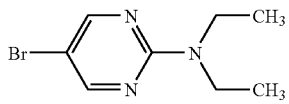

In an autoclave, N,N-dimethylamine hydrochloride (2.04 g, 25 mmol), potassium carbonate (6.91 g, 50 mmol), 5-bromo-2-chloropyrimidine (4.35 g, 22.50 mmol) and toluene (25 ml) are heated at 110° C. (bath temperature) for 20 hours. Ethyl acetate (50 ml) is added to the reaction mixture, and the organic phase is then washed with water (2×50 ml), dried over sodium sulphate, filtered and concentrated.

This gives 4.01 g (72% of theory) of N-(5-bromo-2-pyrimidinyl)-N,N-dimethylamine.

HPLC: log P (pH 2.3)=2.20 (purity: 91%) m.p. 68–69° C.

Example III-5

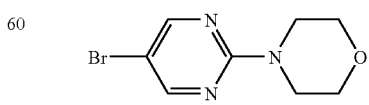

Morpholine (1.44 g, 16.5 mmol) is initially charged in acetonitrile (70 ml). Potassium carbonate (2.30 g, 16.5 mmol) is added, and the reaction mixture is stirred at room temperature for another hour. 5-Bromo-2-chloropyrimidine (2.90 g, 15.0 mmol) is added, and the reaction mixture is stirred at reflux for another 16 hours. After cooling, the reaction mixture is stirred into water (100 ml) and then extracted with ethyl acetate (2×50 ml). The organic phase is dried over sodium sulphate, filtered and concentrated.

This gives 2.95 g (81% of theory) of 4-(5-bromo-2-pyrimidinyl)morpholine.

HPLC: log P (pH 2.3)=2.15 (purity: 92%) m.p. 90° C.

Example III-6

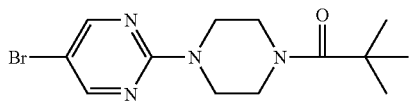

5-Bromo-2-(1-piperazinyl)pyrimidine (1.43 g, 5.90 mmol) and triethylamine (1 ml) are suspended in ethyl acetate (30 ml). At 10° C., pivaloyl chloride (0.8 ml, 6.5 mmol) is added dropwise, and the reaction mixture is stirred at room temperature for another 16 hours and then admixed successively with ethyl acetate and water. The organic phase is washed with saturated aqueous sodium chloride solution, dried over sodium sulphate, filtered and concentrated.

This gives 1.47 g (76% of theory) of 1-(tert-butylcarbonyl)-4-(5-bromo-2-pyrimidinyl)piperazine.

HPLC: log P (pH 2.3)=2.86 (purity: 99%) m.p. 166–172° C.

Example III-7

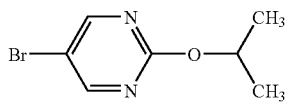

Isopropanol (25 ml) is initially charged, and sodium hydride (0.50 g, 60%, 16.5 mmol) is then added a little at a time under an atmosphere of argon, and the reaction mixture is stirred at 60° C. for another 30 minutes. 5-Bromo-2-chloropyrimidine (2.90 g, 15.0 mmol) is then added, and the reaction mixture is stirred at reflux for another 16 hours. After cooling, the reaction mixture is stirred into water (75 ml) and then extracted with ethyl acetate (2×75 ml). The organic phase is dried over sodium sulphate, filtered and concentrated. The crude product is purified by silica gel chromatography (mobile phase: n-hexane/ethyl acetate 9:1, v/v).

This gives 2.10 g (65% of theory) of 5-bromo-2-pyrimidinyl isopropyl ether.

HPLC: log P (pH 2.3)=2.39 (purity: 99%)

Example III-8

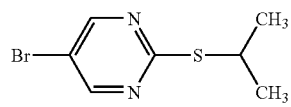

Sodium 2-propanethiolate (1.62 g, 16.5 mmol) is initially charged in DMF (40 ml). At room temperature, 5-bromo-2-chloropyrimidine (2.90 g, 15.0 mmol) is added, and the reaction mixture is stirred at room temperature for another 16 hours. The reaction mixture is then stirred into water (100 ml) and extracted with ethyl acetate (2×75 ml). The organic phase is washed with saturated sodium chloride solution, dried over sodium sulphate, filtered and concentrated. The crude product is purified by silica gel chromatography (mobile phase: n-hexane/ethyl acetate 20:1, v/v).

This gives 0.40 g (11% of theory) of 5-bromo-2-pyrimidinyl isopropyl sulphide.

HPLC: log P (pH 2.3)=3.34 (purity: 100%)

Example III-9

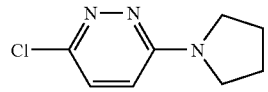

In an autoclave, 3,6-dichloropyridazine (3.35 g, 22.5 mmol), potassium carbonate (3.45 g, 25.0 mmol), pyrrolidine (1.78 g, 25.0 mmol) and toluene (25 ml) are heated at 110° C. (bath temperature) for 20 hours. The toluene is then removed under reduced pressure, the crude product is admixed with water and the product is then filtered off with suction.

This gives 3.57 g (86% of theory) of 3-chloro-6-(1–pyrrolidinyl)pyridazine. m.p. 129–131° C.

Example III-10

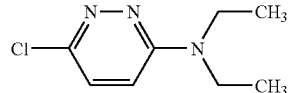

In an autoclave, 3,6-dichloropyridazine (3.35 g, 22.5 mmol), potassium carbonate (3.45 g, 25.0 mmol), N,N-diethylamine (1.83 g, 25.0 mmol) and toluene (25 ml) are heated at 110° C. (bath temperature) for 20 hours. Water (50 ml) and ethyl acetate (25 ml) are added to the reaction mixture, and the phases are separated. The aqueous phase is re-extracted with ethyl acetate (25 ml), and the combined organic phases are dried over sodium sulphate and filtered. Florisil (10 g) is added to the filtrate, and the mixture is concentrated. The crude product is purified by silica gel chromatography (mobile phase: n-hexane/ethyl acetate 3:1, v/v).

This gives 1.25 g (30% of theory) of N-(6-chloro-3-pyridazinyl)-N,N-diethylamine.

HPLC: log P (pH 2.3)=0.51 (purity: 97%) m.p. 4246° C.

Example III-11

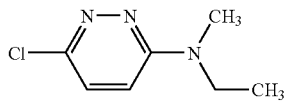

In an autoclave, 3,6-dichloropyridazine (3.35 g, 22.5 mmol), potassium carbonate (3.45 g, 25.0 mmol), N-methyl-N-ethylamine (1.48 g, 25.0 mmol) and toluene (25 ml) are heated at 110° C. (bath temperature) for 20 hours. Water (50 ml) and ethyl acetate (50 ml) are added to the reaction mixture, and the phases are separated. The aqueous phase is re-extracted with ethyl acetate (25 ml), and the combined organic phases are dried over sodium sulphate and filtered. Florisil (10 g) is added to the filtrate, and the mixture is concentrated. The crude product is purified by silica gel chromatography (mobile phase: n-hexane/ethyl acetate 4:1, v/v).

This gives 2.50 g (65% of theory) of N-(6-chloro-3-pyridazinyl)-N-ethyl-N-methylamine. m.p. 61–63° C.

Example III-12

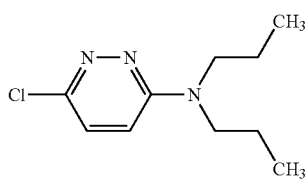

N,N-Dipropylamine (2.53 g, 25.0 mmol) and potassium carbonate (3.45 g, 25.0 mmol) are suspended in DMF (50 ml) and stirred for another 30 minutes. 3,6-Dichloropyridazine (3.35 g, 22.5 mmol) is added, and the reaction mixture is stirred at 110° C. for another 16 hours. DMF is removed under reduced pressure and water (50 ml) and ethyl acetate (50 ml) are added to the residue. The organic phase is dried over sodium sulphate and filtered. Florisil (10 g) is added to the filtrate, and the mixture is concentrated. The crude product is purified by silica gel chromatography (mobile phase: n-hexane/ethyl acetate 9:1→4:1, in each case v/v).

This gives 1.10 g (30% of theory) of N-(6-chloro-3-pyridazinyl)-N,N-dipropylamine.

HPLC: log P (pH 2.3)=1.82 (purity: 99%) m.p. 64–66° C.

Example III-13

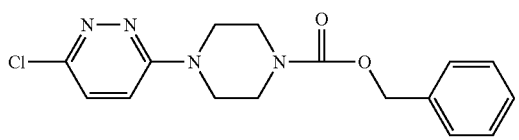

Benzyl piperazine-N-carboxylate (2.20 g, 0.01 mol) is initially charged in acetonitrile (50 ml). Potassium carbonate (1.38 g, 0.01 mol) is added, and the reaction mixture is stirred at room temperature for another 30 minutes. 3,6-Dichloropyridazine (1.49 g, 0.01 mol) is added, and the reaction mixture is stirred at 100° C. for another 16 hours.

After cooling to room temperature, the reaction mixture is stirred into water (100 ml). The product is filtered off with suction.

This gives 1.95 g (58% of theory) of benzyl 4-(6-chloro-3-pyridazinyl)-1-piperazinecarboxylate.

HPLC: log P (pH 2.3)=2.36 (purity: 95%) m.p. 124–125° C.

Example III-14

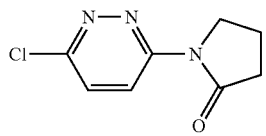

Sodium hydride (0.80 g, 60%, 0.02 mol) is suspended in DMF (40 ml). Under a stream of argon, 2-pyrrolidone (1.70 g, 0.02 mol) is added dropwise at 10° C. The reaction mixture is allowed to warm to room temperature, 3,6-dichloropyridazine (2.23 g, 0.015 mol) is added and the reaction mixture is stirred at room temperature 16 hours. The reaction mixture is then stirred into water (300 ml) and extracted with ethyl acetate (200 ml). The organic phase is washed with saturated aqueous sodium chloride solution, dried over sodium sulphate, filtered and concentrated. The crude product is purified by silica gel chromatography (mobile phase: n-hexane/ethyl acetate 1:1→3:7, in each case v/v).

This gives 0.68 g (17% of theory) of 1-(6-chloro-3-pyridazinyl)-2-pyrrolidinone.

HPLC: log P (pH 2.3)=1.09 (purity: 75%)

Example III-15

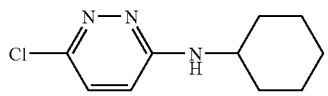

3,6-Dichlorpyridazine (11.20 g, 0.075 mol), cyclohexylamine (25.70 ml, 0.225 mol) and water (37.5 ml) are initially charged. At room temperature, concentrated hydrochloric acid (1.5 ml, 37% strength) is added, and the reaction mixture is stirred at 100° C. (bath temperature) for another 20 hours. After cooling, saturated aqueous sodium bicarbonate solution is added (30 ml). The precipitate is filtered off with suction and washed repeatedly with water.

This gives 12.30 g (78% of theory) of N-(6-chloro-3-pyridazinyl)-N-cyclohexylamine.

HPLC: log P (pH 2.3)=0.95 (purity: 99%) m.p. 161–163° C.

Example III-16

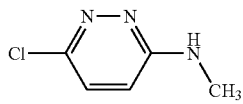

In an autoclave, 3,6-dichloropyridazine (25.0 g, 0.17 mol), methylamine (39.0 g, 40% strength solution in water, 0.50 mol), water (50 ml) and concentrated hydrochloric acid (3.4 ml, 37% strength) are heated at 100° C. (bath temperature) for 20 hours. After cooling, the precipitate is filtered off with suction and washed repeatedly with saturated aqueous sodium bicarbonate solution.

This gives 20.95 g (78% of theory) of N-(6-chloro-3-pyridazinyl)-N-methylamine.

m.p. 194–196° C. GC/MS: index 1472 (purity: 100%); $M^+=143/145$

Example III-17

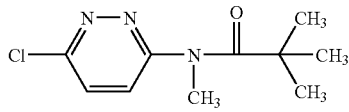

N-(6-Chloro-3-pyridazinyl)-N-methylamine (1.08 g, 0.0075 mol) and triethylamine (1.4 ml, 0.01 mol) are initially charged in ethyl acetate (50 ml). At 60° C., pivaloyl chloride (1.23 ml, 0.01 mol) is added dropwise, and the reaction mixture is stirred at 60° C. for another 16 hours. After cooling, the reaction mixture is washed with water and the organic phase is dried over sodium sulphate, filtered and concentrated.

This gives 1.21 g (71% of theory) of N-(6-chloro-3-pyridazinyl)-N-methyl-N-2,2-trimethylpropanamide.

HPLC: log P (pH 2.3)=1.69 (purity: 95%) m.p. 84–87° C.

Example III-18

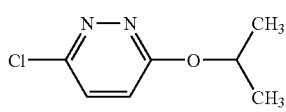

Isopropanol (60 ml) is initially charged, and under a stream of argon, sodium hydride (1.0 g, 80%, 0.033 mol) is added a little at a time at room temperature, and the mixture is then stirred at 60° C. for 30 minutes. At room temperature, 3,6-dichloropyridazine (4.50 g, 0.03 mol) is added, and the reaction mixture is stirred at reflux for 48 hours. The reaction mixture is stirred into water (100 ml) and extracted with ethyl acetate (2×100 ml). The organic phase is dried over sodium sulphate, filtered and concentrated. The crude product is purified by silica gel chromatography (mobile phase: n-hexane/ethyl acetate 9:1, v/v).

This gives 1.85 g (36% of theory) of 3-chloro-6-isopropoxypyridazine.

HPLC: log P (pH 2.3)=1.94 (purity: 98%) m.p. 83–85° C.

Example III-19

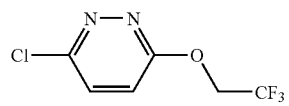

Trifluoroethanol (25.0 g, 0.25 mol) is initially charged in acetonitrile (200 ml). Potassium carbonate (6.90 g, 0.05 mol) is added, and the reaction mixture is stirred at room temperature for another hour. 3,6-Dichloropyridazine (11.20 g, 0.075 mol) is added, and the reaction mixture is then stirred at reflux for 16 hours. The reaction mixture is stirred in water (500 ml) and extracted with ethyl acetate (2×300 ml). The organic phase is dried over sodium sulphate, filtered and concentrated.

This gives 12.38 g (68% of theory) of 3-chloro-6-(2,2,2-trifluoroethoxy)pyridazine.

HPLC: log P (pH 2.3) 2.05 (purity: 88%)

Example III-20

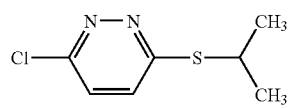

Sodium 2-propanethiolate (1.62 g, 16.5 mmol) is initially charged in DMF (30 ml). At room temperature, a solution of 3,6-dichloropyridazine (2.20 g, 15.0 mmol) in DMF (10 ml) is added. The reaction mixture is stirred at room temperature for another 16 hours, stirred into water (100 ml) and then extracted with ethyl acetate (2×75 ml). The organic phase is washed with saturated sodium chloride solution (2×75 ml), dried over sodium sulphate, filtered and concentrated. The crude product is purified by silica gel chromatography (mobile phase: n-hexane/ethyl acetate 9:1, v/v).

This gives 1.40 g (50% of theory) of 6-chloro-3-pyridazinyl isopropyl sulphide.

HPLC: log P (pH 2.3)=2.34 (purity: 100%) m.p. 90–91° C.

Example III-21

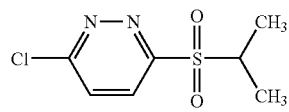

6-Chloro-3-pyridazinyl isopropyl sulphide (1.90 g, 0.01 mol) is initially charged in dichloromethane (100 ml). At room temperature, 3-chloroperoxybenzoic acid (5.06 g, 0.022 mol) is added a little at a time. The reaction mixture is stirred at room temperature for another 16 hours and the precipitate is filtered off with suction and discarded. The filtrate is washed successively with aqueous sodium dithionite solution, saturated aqueous sodium bicarbonate solution (2×50 ml) and water (1×50 ml), dried over sodium sulphate, filtered and concentrated.

This gives 1.93 g (76% of theory) of 6-chloro-3-pyridazinyl isopropyl sulphone.

HPLC: log P (pH 2.3)=1.20 (purity: 88%) m.p. 122–124° C.

Example III-22

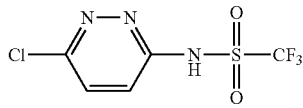

3-Amino-6-chloropyridazine (3.20 g, 0.025 mmol) is suspended in dichloromethane (100 ml). At room temperature, triethylamine (4.20 ml, 0.025 mol) and trifluoromethanesulphonic anhydride (4.20 ml, 0.025 mol) are successively added dropwise. The reaction mixture is stirred at room temperature for another hour, washed successively with saturated aqueous sodium bicarbonate solution (3×50 ml) and saturated aqueous sodium chloride solution (1×50 ml), dried over sodium sulphate, filtered and concentrated. The crude product is purified by silica gel chromatography (mobile phase: n-hexane/ethyl acetate 3:1→0:1, in each case v/v).

This gives 2.51 g (38% of theory) of N-(6-chloro-3-pyridazinyl)(trifluoro)methane-sulphonamide.

HPLC: log P (pH 2.3)=1.56 (purity: 99%)

Example III-23

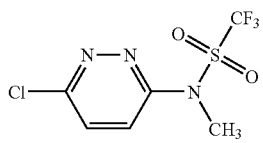

N-(6-Chloro-3-pyridazinyl)(trifluoro)methanesulphonamide (1.20 g, 4.6 mmol) is initially charged in acetonitrile (40 ml). At room temperature, potassium carbonate (0.95 g, 6.7 mmol) is added, and the mixture is stirred for another 30 minutes. At room temperature, iodomethane (0.42 ml, 6.7 mmol) is then added dropwise, and the reaction mixture is stirred at 40° C. for another 16 hours. The reaction mixture is stirred into water (50 ml) and the precipitate is filtered off with suction and washed with ethyl acetate (2×50 ml). The combined organic phases are washed with saturated aqueous sodium chloride solution (1×50 ml), dried over sodium sulphate, filtered and concentrated. The crude product is purified by silica gel chromatography (mobile phase: n-hexane/ethyl acetate 4:1, v/v).

This gives 0.68 g (54% of theory) of N-(6-chloro-3-pyridazinyl)(trifluoro)-N-methyl-methanesulphonamide.

HPLC: log P (pH 2.3)=2.18 (purity: 100%)

The stated log P values were determined in accordance with EEC Directive 79/831 Annex V.A8 by HPLC (High Performance Liquid Chromatography) using a reversed-phase column (C 18). Temperature: 43° C.

Mobile phases for determination in the acidic range: 0.1% aqueous phosphoric acid, acetonitrile; linear gradient from 10% acetonitrile to 90% acetonitrile.

Calibration was carried out using unbranched alkan-2-ones (having 3 to 16 carbon atoms) with known log P values (determination of the log P values by the retention times using linear interpolation between two successive alkanones).

The lambda max values were determined in the maxima of the chromatographic signals using the UV spectra from 200 nm to 400 nm.

USE EXAMPLES

Example A

*Heliothis Virescens* Test

| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Soya bean shoots (*Glycine max*) are treated by being dipped into the preparation of active compound of the desired concentration and are populated with *Heliothis virescens* caterpillars whilst the leaves are still moist.

After the desired period of time, the kill in % is determined. 100% means that all caterpillars have been killed; 0% means that none of the caterpillars have been killed.

Active compounds, active compound concentrations and test results are shown in the table below.

TABLE A

Plant-damaging insects
*Heliothis virescens* test

| Active compounds | Active compound concentration in ppm | Kill rate in % after 7[d] |
|---|---|---|
| 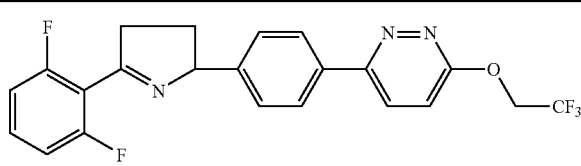 | 40 | 100 |

TABLE A-continued

Plant-damaging insects
*Heliothis virescens* test

| Active compounds | Active compound concentration in ppm | Kill rate in % after 7ᵈ |
|---|---|---|
| [structure: 2,6-difluorophenyl-pyrroline-phenyl-pyrimidine-O-isopropyl] | 40 | 100 |
| [structure: 2,6-difluorophenyl-pyrroline-phenyl-pyridine-CF₃] | 40 | 100 |
| [structure: 2,6-difluorophenyl-pyrroline-phenyl-pyridine-O-CH₂CF₃] | 500 | 100 |
| [structure: 2,6-difluorophenyl-pyrroline-phenyl-pyrimidine-N(ethyl)(propyl)] | 40 | 100 |
| [structure: 2,6-difluorophenyl-pyrroline-phenyl-pyridine-morpholine] | 500 | 100 |

Example B

*Phaedon* Larvae Test

| | |
|---|---|
| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) whilst the leaves are still moist.

After the desired period of time, the kill in % is determined. 100% means that all beetle larvae have been killed; 0% means that none of the beetle larvae have been killed.

Active compounds, active compound concentrations and test results are shown in the table below.

TABLE B

Plant-damaging insects
Phaedon larvae test

| Active compounds | Active compound concentration in ppm | Kill rate in % after 7$^d$ |
|---|---|---|
| [structure: 2,6-difluorophenyl-dihydropyrrole-phenyl-pyrimidine-O-CH(CH3)2] | 1000 | 100 |
| [structure: 2,6-difluorophenyl-dihydropyrrole-phenyl-pyridine-CF3] | 1000 | 100 |
| [structure: 2,6-difluorophenyl-dihydropyrrole-phenyl-pyrimidine-S-CH(CH3)2] | 1000 | 100 |
| [structure: 2,6-difluorophenyl-dihydropyrrole-phenyl-pyridine-O-CH2CF3] | 1000 | 100 |
| [structure: 2,6-difluorophenyl-dihydropyrrole-phenyl-pyrimidine-N(CH2CH3)2] | 1000 | 100 |
| [structure: 2,6-difluorophenyl-dihydropyrrole-phenyl-pyrimidine-3,5-dimethylpiperidine] | 1000 | 100 |
| [structure: 2,6-difluorophenyl-dihydropyrrole-phenyl-pyrimidine-piperidine] | 1000 | 100 |

Example C

*Spodoptera Exigua* Test

| | |
|---|---|
| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with army worm (*Spodoptera exigua*) caterpillars whilst the leaves are still moist.

After the desired period of time, the kill in % is determined. 100% means that all caterpillars have been killed; 0% means that none of the caterpillars have been killed.

Active compounds, active compound concentrations and test results are shown in the table below.

TABLE C

Plant-damaging insects
*Spodoptera exigua* test

| Active compounds | Active compound concentration in ppm | Kill rate in % after 7$^d$ |
|---|---|---|
| 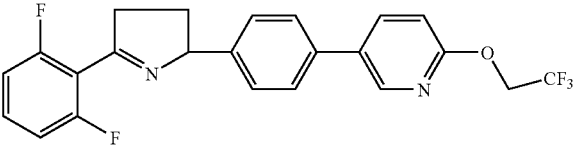 | 500 | 100 |
| 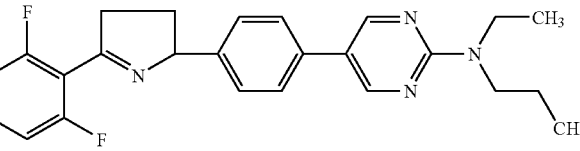 | 500 | 100 |
| 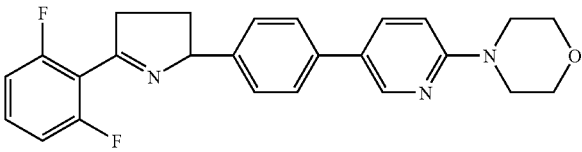 | 1000 | 100 |

Example D

*Spodoptera frugiperda* Test

| Solvent: | 30 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with army worm (*Spodoptera frugiperda*) caterpillars whilst the leaves are still moist.

After the desired period of time, the kill in % is determined. 100% means that all caterpillars have been killed; 0% means that none of the caterpillars have been killed.

Active compounds, active compound concentrations and test results are shown in the table below.

TABLE D

Plant-damaging insects
*Spodoptera frugiperda* test

| Active compounds | Active compound concentration in ppm | Kill rate in % after 7$^d$ |
|---|---|---|
| 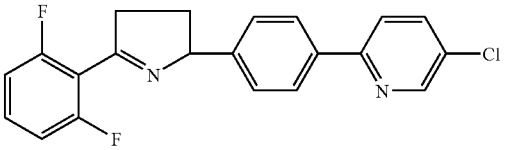 | 1000 | 100 |
| 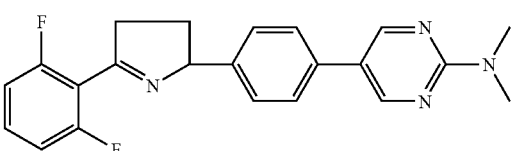 | 1000 | 100 |

TABLE D-continued
Plant-damaging insects
Spodoptera frugiperda test
| Active compounds | Active compound concentration in ppm | Kill rate in % after 7$^d$ |
|---|---|---|
| 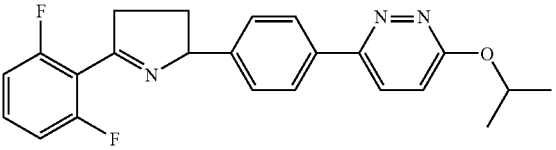 | 1000 | 100 |
| 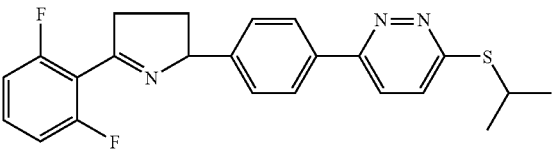 | 1000 | 100 |
| 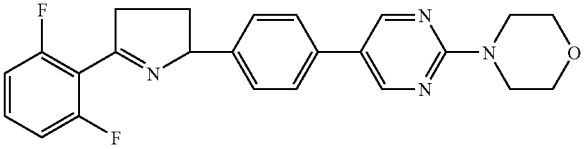 | 1000 | 100 |
| 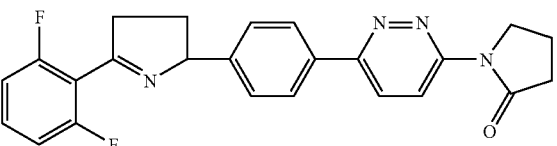 | 500 | 100 |
|  | 500 | 100 |
| 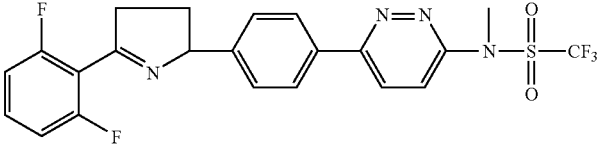 | 500 | 100 |
| 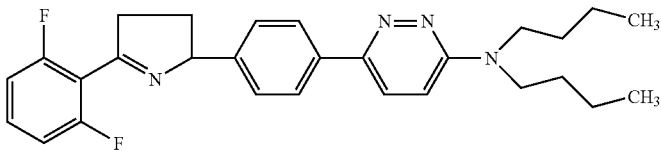 | 500 | 100 |
| 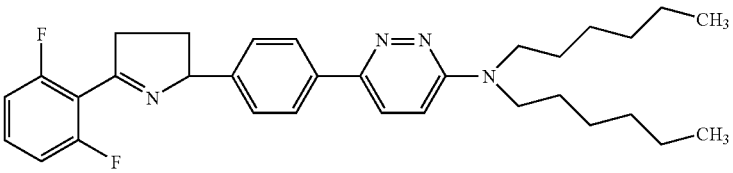 | 1000 | 100 |
| 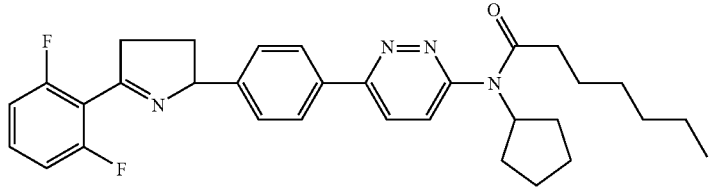 | 1000 | 100 |

TABLE D-continued

Plant-damaging insects
*Spodoptera frugiperda* test

| Active compounds | Active compound concentration in ppm | Kill rate in % after 7$^d$ |
|---|---|---|
| [structure] | 1000 | 100 |
| [structure] | 1000 | 100 |
| [structure] | 1000 | 100 |

Example E

*Tetranychus* Test (OP Resistant/Dip Treatment)

| Solvent: | 30 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (tetranychus urticae) are dipped into a preparation of active compound of the desired concentration.

After the desired period of time, the effect in % is determined. 100% means that all spider mites have been killed; 0% means that none of the spider mites have been killed.

Active compounds, active compound concentrations and test results are shown in the table below

TABLE E

Plant-damaging mites
Tetranychus test (OP-resistant/dip treatment)

| Active compounds | Active compound concentration in ppm | Kill rate in % after 7$^d$ |
|---|---|---|
| [structure] | 100 | 98 |
| [structure] | 100 | 98 |

TABLE E-continued

Plant-damaging mites
Tetranychus test (OP-resistant/dip treatment)

| Active compounds | Active compound concentration in ppm | Kill rate in % after $7^d$ |
|---|---|---|
| [structure] | 100 | 98 |
| [structure] | 100 | 98 |
|  | 100 | 98 |
|  | 100 | 98 |
| [structure] | 100 | 98 |
| [structure] | 100 | 98 |
| [structure] | 100 | 98 |

Example F

*Diabrotica Balteata* Test (Larvae in Soil)

Critical Concentration Test/Soil Insects—Treatment of Transgenic Plants

| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the corresponding test insects are placed into the treated soil. After a further 7 days, the efficacy of the active compound is determined by counting the number of maize plants that have emerged (1 plant=20% activity).

Example G

*Heliothis virescens* Test (Treatment of Transgenic Plants)

| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the cultivar Roundup Ready (trade mark of Monsanto Comp. USA) are treated by being dipped into the preparation of active compound of the desired concentration and populated with the tobacco budworm caterpillar Heliothis virescens whilst the leaves are still moist.

After the desired period of time, the kill in % is determined. 100% means that all caterpillars have been killed; 0% means that none of the caterpillars have been killed.

What is claimed is:

1. A $\Delta^1$-pyrroline of formula (I)

(I)

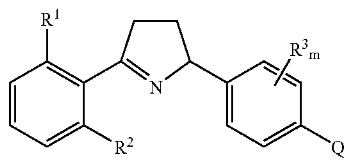

in which $R^1$ represents halogen or methyl, $R^2$ represents hydrogen or halogen, $R^3$ represents halogen or optionally substituted alkyl, alkoxy, or alkylthio, m represents 0, 1, 2, 3, or 4, Q represents one of the groupings $R^4$ represents hydrogen, halogen, cyano, formyl, nitro, or trialkylsilyl; represents optionally substituted alkyl, alkenyl, alkoxy, or alkenyloxy; represents pentafluorothio, $—S(O)_pR^6$, $—NR^7R^8$, $—COR^6$, $—CO_2R^6$, $—CONR^9R^{10}$, $—N(R^{11})COR^{12}$, or $—C(R^{13}){=}N—OR^{14}$; represents optionally substituted cycloalkyl, cycloalkylalkyl, aryl, arylalkyl, or saturated or unsaturated heterocyclyl or heterocyclylalkyl; represents $—CH{=}NOH$ or formyl; or represents optionally substituted cycloalkyloxy or cycloalkylalkoxy, $R^5$ represents halogen, cyano, formyl, nitro, or trialkylsilyl; represents optionally substituted alkyl, alkenyl, alkoxy, or alkenyloxy; represents pentafluorothio, $—S(O)_pR^6$, $—NR^7R^8$, $—COR^6$, $—SO_2R^6$, $—CONR^9R^{10}$, $—N(R^{11})COR^{12}$, or $—(R^{13}){=}N—OR^{14}$; or represents optionally substituted cycloalkyl, cycloalkylalkyl, aryl, arylalkyl, or saturated or unsaturated heterocyclyl or heterocyclylalkyl, p represents 0, 1, or 2, n represents 0, 1, 2, or 3, with the proviso that if n represents 2 or 3 then the substituents $R^5$ can be identical or different, r represents 0, 1, or 2, with the proviso that if r represents 2 then the substituents $R^5$ can be identical or different, $R^6$ represents optionally substituted alkyl, cycloalkyl, aryl, or arylalkyl, $R^7$ and $R^8$ independently of one another represent hydrogen, $—SO_2R^6$, $—COR^6$, or $—CO_2R^6$; or represent optionally substituted alkyl, alkenyl, cycloalkyl, cycloalkylalkyl, aryl, arylalkyl, or saturated or unsaturated heterocyclyl or heterocyclylalkyl, or $R^7$ and $R^8$ together represent optionally substituted alkenylene or alkylene, where the alkylene chain is optionally interrupted by —O—, —S—, or $—NR^{15}—$; or together represent optionally substituted alkylene, where the alkylene chain is interrupted either by $C{=}O$ or by $C{=}NO$-alkyl, $R^9$ and $R^{10}$ independently of one another represent hydrogen or $—SO_2R^6$; represent optionally substituted alkyl, alkenyl, cycloalkyl, cycloalkylalkyl, aryl, arylalkyl, or saturated or unsaturated heterocyclyl or heterocyclylalkyl, or $R^9$ and $R^{10}$ together represent optionally substituted alkylene, where the alkylene chain is optionally interrupted by —O—, —S—, or $—NR^{15}—$, $R^{11}$ and $R^{12}$ independently of one another represent hydrogen; represent optionally substituted alkyl, cycloalkyl, cycloalkylalkyl, aryl, or arylalkyl, or $R^{11}$ and $R^{12}$ together represent optionally substituted alkylene or alkenylene, $R^{13}$ and $R^{14}$ independently of one another represent hydrogen or represent optionally substituted alkyl or alkenyl, and $R^{15}$ represents hydrogen, $—SO_2R^6$, $—COR^6$, or $—CO_2R^6$; or represents optionally substituted alkyl, alkenyl, cycloalkyl, cycloalkylalkyl, aryl, arylalkyl, or saturated or unsaturated heterocyclyl or heterocyclylalkyl.

2. A $\Delta^1$-pyrroline of formula (I) according to claim 1 in which $R^1$ represents halogen or methyl, $R^2$ represents hydrogen or halogen, $R^3$ represents halogen; or represents optionally halogen-substituted alkyl, alkoxy, or alkylthio, m represents 0, 1, 2, 3, or 4, Q represents one of the groupings $R^4$ represents hydrogen, halogen, cyano, formyl, nitro, or trialkylsilyl; represents alkyl, alkenyl, alkoxy, or alkenyloxy, each of which is optionally mono- or polysubstituted by identical or different substituents selected from the group consisting of halogen, cyano, and —NR⁷R⁸; represents pentafluorothio, —S(O)$_p$R⁶, —NR⁷R⁸, —COR⁶, —CO₂R⁶, —CONR⁹R¹⁰, —N(R¹¹)COR¹², or —C(R¹³)=N—OR¹⁴; represents cycloalkyl, cycloalkylalkyl, aryl, arylalkyl, or saturated or unsaturated, 5- to 10-membered heterocyclyl or heterocyclylalkyl, each of which is optionally mono- or polysubstituted by identical or different substituents selected from the group consisting of halogen, cyano, nitro, alkyl, halogenoalkyl, alkenyl, halogenoalkenyl, alkoxy, halogenoalkoxy, alkylthio, and halogenoalkylthio; represents —CH=NOH, formyl; or represents cycloalkyloxy or cycloalkylalkoxy, each of which is optionally mono- or polysubstituted by identical or different substituents selected from the group consisting of halogen and alkyl, R⁵ represents halogen, cyano, formyl, nitro, or trialkylsilyl; represents alkyl, alkenyl, alkoxy, or alkenyloxy, each of which is optionally mono- or poly-substituted by identical or different substituents selected from the group consisting of halogen, cyano, and —NR⁷R⁸; represents pentafluorothio, —S(O)$_p$R⁶, —NR⁷R⁸, —COR⁶, —CO₂R⁶, —CONR⁹R¹⁰, —N(R¹¹)COR¹², or —C(R¹³)=N—OR¹⁴; or represents cycloalkyl, cycloalkylalkyl, aryl, arylalkyl, or saturated or unsaturated, 5- to 10-membered heterocyclyl or heterocyclylalkyl, each of which is optionally mono- or polysubstituted by identical or different substituents selected from the group consisting of halogen, alkyl, halogenoalkyl, alkenyl, halogenoalkenyl, alkoxy, halogenoalkoxy, alkylthio, and halogenoalkylthio, p represents 0, 1, or 2, n represents 0, 1, 2, or 3, with the proviso that if n represents 2 or 3 then the substituents R⁵ can be identical or different, r represents 0, 1, or 2, with the proviso that if r represents 2 then the substituents R⁵ can be identical or different, R⁶ represents alkyl that is optionally mono- or polysubstituted by identical or different substituents selected from the group consisting of halogen, —NR⁷R⁸, alkoxy, alkylthio, halogenoalkoxy, and halogenoalkylthio; or represents cycloalkyl, aryl, or arylalkyl, each of which is optionally mono- or polysubstituted by identical or different substituents selected from the group consisting of halogen, cyano, alkyl, halogenoalkyl, alkoxy, halogenoalkoxy, alkylthio, and halogenoalkylthio; represents alkyl that is mono- or polysubstituted by identical or different substituents selected from the group consisting of alkoxy, alkylthio, halogenoalkoxy, and halogenoalkylthio, R⁷ and R⁸ independently of one another represent hydrogen, —SO₂R⁶, —COR⁶, or —CO₂R⁶; represent alkyl or alkenyl, each of which is optionally mono- or polysubstituted by identical or different substituents selected from the group consisting of halogen, alkylcarbonyl, alkylcarbonyloxy, alkylamino, dialkylamino, alkoxy, halogenoalkoxy, alkylthio, and halogenoalkylthio; represents cycloalkyl, cycloalkylalkyl, aryl, arylalkyl, or saturated or unsaturated 5- to 10-membered heterocyclyl or heterocyclylalkyl, each of which is optionally mono- or polysubstituted by identical or different substituents selected from the group consisting of halogen, cyano, alkyl, halogenoalkyl, alkoxy, halogenoalkoxy, alkylthio, and halogenoalkylthio, or R⁷ and R⁸ together represent alkenylene that is optionally mono- or polysubstituted by identical or different substituents selected from the group consisting of halogen, cyano, alkoxy, halogenoalkoxy, alkylthio, and halogenoalkylthio; together represent alkylene that is optionally mono- or polysubstituted by identical or different substituents selected from the group consisting of halogen, cyano, alkyl, halogenoalkyl, alkoxy, halogenoalkoxy, alkylthio, and halogenoalkylthio, where the alkylene chain is optionally interrupted by —O—, —S—, or —NR¹⁵—; together represent alkylene that is mono- or polysubstituted by identical or different substituents selected from the group consisting of alkoxycarbonyl and oxyalkyleneoxy; or together represent alkylene, where the alkylene chain is interrupted either by C=O or by C=NO-alkyl, R⁹ and R¹⁰ independently of one another represent hydrogen or —SO₂R⁶; represent alkyl or alkenyl, each of which is optionally mono- or polysubstituted by identical or different substituents selected from the group consisting of halogen, alkylamino, dialkylamino, alkoxy, and alkylthio; or represent cycloalkyl, cycloalkylalkyl, aryl, arylalkyl, or saturated or unsaturated 5- to 10-membered heterocyclyl or heterocyclylalkyl, each of which is optionally mono- or polysubstituted by identical or different substituents selected from the group consisting of halogen, cyano, alkyl, halogenoalkyl, alkoxy, halogenoalkoxy, alkylthio and halogenoalkylthio, or R⁹ and R¹⁰ together represent alkylene that is optionally mono- or polysubstituted by identical or different substituents selected from the group consisting of halogen, cyano, alkyl, halogenoalkyl, alkoxy, halogenoalkoxy, alkylthio, and halogenoalkylthio, where the alkylene chain is optionally interrupted by —O—, —S—, or —NR¹⁵—, R¹¹ and R¹² independently of one another represent hydrogen; represent alkyl that is optionally mono- or polysubstituted by identical or different substituents selected from the group consisting of halogen, cyano, alkoxy, and alkylthio; represent cycloalkyl, cycloalkylalkyl, aryl, or arylalkyl, each of which is optionally mono- or polysubstituted by identical or different substituents selected from the group consisting of halogen, cyano, alkyl, halogenoalkyl, alkoxy, halogenoalkoxy, alkylthio, and halogenoalkylthio, or R¹¹ and R¹² together represent alkylene or alkenylene, each of which is optionally mono- or polysubstituted by identical or different substituents selected from the group consisting of halogen, alkyl, halogenoalkyl, alkoxy, halogenoalkoxy, alkylthio, and halogenoalkylthio, R¹³ and R¹⁴ independently of one another represent hydrogen; or represent alkyl or alkenyl, each of which is optionally mono- or polysubstituted by halogen, and R¹⁵ represents hydrogen, —SO₂R⁶, —COR⁶, or —CO₂R⁶; represents alkyl or alkenyl, each of which is optionally mono- or polysubstituted by identical or different substituents selected from the group consisting of halogen, cyano, alkylamino, dialkylamino, alkoxy, halogenoalkoxy, alkylthio and halogenoalkylthio; or represents cycloalkyl, cycloalkylalkyl, aryl, arylalkyl, or saturated or unsaturated 5- to 10-membered heterocyclyl or heterocyclylalkyl, each of which is optionally mono- or polysubstituted by identical or different substituents selected from the group consisting of halogen, cyano, alkyl, halogenoalkyl, alkoxy, halogenoalkoxy, alkylthio, and halogenoalkylthio.

3. A Δ¹-pyrroline of formula (I) according to claim 1 in which $R^1$ represents fluorine, chlorine, bromine, or methyl, $R^2$ represents hydrogen, fluorine, chlorine, or bromine, $R^3$ represents fluorine, chlorine, or bromine; or represents $C_1$–$C_6$-alkyl, $C_1$–$C_6$-alkoxy, or $C_1$–$C_6$-alkylthio, each of which is optionally mono- to octasubstituted by halogen, m represents 0, 1, 2, or 3, Q represents one of the groupings

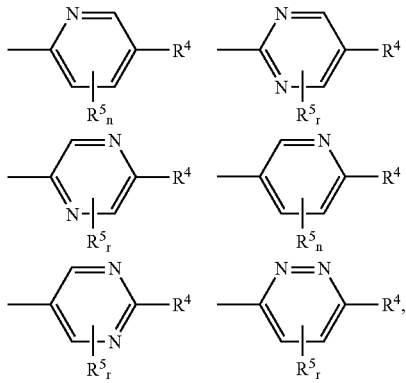

$R^4$ represents hydrogen, fluorine, chlorine, bromine, cyano, formyl, nitro, or tri-($C_1$–$C_6$-alkyl)silyl; represents $C_1$–$C_{20}$-alkyl, $C_2$–$C_{20}$-alkenyl, $C_1$–$C_{20}$-alkoxy, or $C_2$–$C_{20}$-alkenyloxy, each of which is optionally mono- or polysubstituted by identical or different substituents selected from the group consisting of halogen, cyano, and —$NR^7R^8$; represents pentafluorothio, —$S(O)_pR^6$, —$NR^7R^8$, —$COR^6$, —$CO_2R^6$, —$CONR^9R^{10}$, —$N(R^{11})COR^{12}$, or —$C(R^{13})$=N—$OR^{14}$; represents $C_3$–$C_{12}$-cycloalkyl, $C_3$–$C_7$-cyclo-$C_1$–$C_4$-alkyl, aryl, aryl-$C_1$–$C_4$-alkyl, or saturated or unsaturated, 5- to 10-membered heterocyclyl or heterocyclyl-$C_1$–$C_4$-alkyl having 1 to 4 heteroatoms comprising 0 to 4 nitrogen atoms, 0 to 2 nonadjacent oxygen atoms, and/or 0 to 2 nonadjacent sulphur atoms, each of which is optionally mono- to tetrasubstituted by identical or different substituents selected from the group consisting of halogen, cyano, nitro, $C_1$–$C_6$-alkyl, $C_1$–$C_6$-halogenoalkyl, $C_2$–$C_6$-alkenyl, $C_2$–$C_6$-halogenoalkenyl, $C_1$–$C_6$-alkoxy, $C_1$–$C_6$-halogenoalkoxy, $C_1$–$C_6$-alkylthio, and $C_1$–$C_6$-halogenoalkylthio; or represents —CH=NOH, formyl; represents $C_3$–$C_6$-cycloalkyloxy or $C_3$–$C_6$-cycloalkyl-$C_1$–$C_4$-alkoxy, each of which is optionally mono- to tetrasubstituted by identical or different substituents from the group consisting of fluorine, chlorine, bromine and $C_1$–$C_2$-alkyl, $R^5$ represents fluorine, chlorine, bromine, cyano, formyl, nitro, or tri-($C_1$–$C_6$-alkyl)silyl; represents $C_1$–$C_6$-alkyl, $C_2$–$C_6$-alkenyl, $C_1$–$C_6$-alkoxy, or $C_2$–$C_6$-alkenyloxy, each of which is optionally mono- to tridecasubstituted by halogen; or represents pentafluorothio, —$S(O)_pR^6$, —$NR^7R^8$, —$COR^6$, —$CO_2R^6$, —$CONR^9R^{10}$, or —$N(R^{11})COR^{12}$, p represents 0, 1, or 2, n represents 0, 1, 2, or 3, with the proviso that if n represents 2 or 3 then the substituents $R^5$ can be identical or different, r represents 0, 1, or 2, with the proviso that if r represents 2 then the substituents $R^5$ can be identical or different, $R^6$ represents $C_1$–$C_{20}$-alkyl that is optionally mono- or polysubstituted by identical or different substituents selected from the group consisting of halogen, —$NR^7R^8$, alkoxy, alkylthio, halogenoalkoxy, and halogenoalkylthio; or represents $C_3$–$C_6$-cycloalkyl, aryl or aryl-$C_1$–$C_4$-alkyl, each of which is optionally mono- to octasubstituted by identical or different substituents selected from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio, $R^7$ and $R^8$ independently of one another represent hydrogen, —$SO_2R^6$, —$COR^6$, or —$SO_2R^6$; represent $C_1$–$C_{20}$-alkyl or $C_2$–$C_{20}$-alkenyl, each of which is optionally mono- or polysubstituted by identical or different substituents selected from the group consisting of halogen, $C_1$–$C_6$-alkylcarbonyl, $C_1$–$C_6$-alkylcarbonyloxy, $C_1$–$C_6$-alkylamino, di($C_1$–$C_6$-alkyl)amino, $C_1$–$C_6$-alkoxy, $C_1$–$C_6$-halogenoalkoxy, $C_1$–$C_6$-alkylthio and $C_1$–$C_6$-halogenoalkylthio; represent $C_3$–$C_{12}$-cycloalkyl, $C_3$–$C_7$-cycloalkyl-$C_1$–$C_4$-alkyl, aryl, aryl-$C_1$–$C_4$-alkyl, or saturated or unsaturated 5- to 10-membered heterocyclyl or heterocyclyl-$C_1$–$C_4$-alkyl having 1 to 4 heteroatoms comprising 0 to 4 nitrogen atoms, 0 to 2 nonadjacent oxygen atoms, and/or 0 to 2 nonadjacent sulphur atoms, each of which is optionally mono- to tetrasubstituted by identical or different substituents selected from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio; represent heterocyclyl-$C_1$–$C_4$-alkyl having 1 to 4 heteroatoms comprising 0 to 4 nitrogen atoms, 0 to 2 nonadjacent oxygen atoms, and/or 0 to 2 nonadjacent sulphur atoms, each of which is optionally mono- to tetrasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, or $R^7$ and $R^8$ together represent $C_2$–$C_{12}$-alkenylene that is optionally mono- or polysubstituted by identical or different substituents selected from the group consisting of halogen, cyano, $C_1$–$C_6$-alkoxy, $C_1$–$C_6$-halogenoalkoxy, $C_1$–$C_6$-alkylthio, and $C_1$–$C_6$-halogenoalkylthio; together represent $C_3$–$C_{12}$-alkylene that is optionally mono- or polysubstituted in the alkylene moiety by identical or different substituents selected from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio, where the alkylene chain is optionally interrupted by —O—, —S—, or —$NR^{15}$—; together represent $C_3$–$C_{12}$-alkylene that is optionally mono- or polysubstituted by identical or different substituents selected from the group consisting of $C_1$–$C_4$-alkoxycarbonyl and oxy-($C_1$–$C_4$-alkylene)-oxy; or together represent $C_3$–$C_8$-alkylene, where the alkylene chain is interrupted either by C=O or C=NO—($C_1$–$C_6$-alkyl), $R^9$ and $R^{10}$ independently of one another represent hydrogen or —$SO_2R^6$; represent $C_1$–$C_6$-alkyl or $C_2$–$C_6$-alkenyl, each of which is optionally mono- to tridecasubstituted by identical or different substituents selected from the group consisting of halogen, $C_1$–$C_6$-alkylamino, di($C_1$–$C_6$-alkyl)amino, $C_1$–$C_6$-alkoxy, $C_1$–$C_6$-halogenoalkoxy, $C_1$–$C_6$-alkylthio, and $C_1$–$C_6$-halogenoalkylthio; or represent $C_3$–$C_7$-cycloalkyl, $C_3$–$C_7$-cycloalkyl-$C_1$–$C_4$-alkyl, aryl, aryl-$C_1$–$C_4$-alkyl, or saturated or unsaturated 5- to 10-membered heterocyclyl or heterocyclyl-$C_1$–$C_4$-alkyl having 1 to 4 heteroatoms comprising 0 to 4 nitrogen atoms, 0 to 2 nonadjacent oxygen atoms, and/or 0 to 2 nonadjacent sulphur atoms, each of which is optionally mono- to tetrasubstituted by identical or different substituents selected from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio, or $R^9$ and $R^{10}$ together represent $C_3$–$C_6$-alkylene, —$(CH_2)_2$—O—$(CH_2)_2$—, —$(CH_2)_2$—S—$(CH_2)_2$—, or —$(CH_2)_2$—$N(R^{15})$—$(CH_2)_2$—, each of which is optionally mono- to tetrasubstituted in the alkylene moiety by identical or different substituents selected from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio, $R^{11}$ and $R^{12}$ independently of one another represent hydrogen; represent $C_1$–$C_6$-alkyl that is optionally mono- to tridecasubstituted by identical or different substituents selected from the group consisting of halogen, cyano, $C_1$–$C_6$-alkoxy, and $C_1$–$C_6$-alkylthio; represent $C_3$–$C_7$-cycloalkyl, $C_3$–$C_7$-cycloalkyl-$C_1$–$C_4$-alkyl, aryl, or aryl-$C_1$–$C_4$-alkyl, each of which is optionally mono- to octasubstituted by identical or different substituents selected from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio, or $R^{11}$ and $R^{12}$ together represent $C_3$–$C_{10}$-alkylene or $C_3$–$C_{10}$-alkenylene, each of which is optionally mono- to octasubstituted by identical or different substituents selected from the group consisting of halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio, $R^{13}$ and $R^{14}$ independently of one another represent hydrogen; represent $C_1$–$C_6$-alkyl or $C_2$–$C_6$-alkenyl, each of which is optionally mono- or polysubstituted by halogen, and $R^{15}$ represents hydrogen, —$SO_2R^6$, —$COR^6$ or —$CO_2R^6$; represents $C_1$–$C_{20}$-alkyl or $C_2$–$C_{20}$-alkenyl, each of which is optionally mono- or polysubstituted by identical or different substituents selected from the group consisting of halogen, cyano, $C_1$–$C_6$-alkylamino, di($C_1$–$C_6$-alkyl)amino, $C_1$–$C_6$-alkoxy, $C_1$–$C_6$-halogenoalkoxy, $C_1$–$C_6$-alkylthio, and $C_1$–$C_6$-halogenoalkylthio; or represents $C_3$–$C_{12}$-cycloalkyl, $C_3$–$C_7$-cycloalkyl-$C_1$–$C_4$-alkyl, aryl, aryl-$C_1$–$C_4$-alkyl, or saturated or unsaturated 5- to 10-membered heterocyclyl or heterocyclyl-$C_1$–$C_4$-alkyl having 1 to 4 heteroatoms comprising 0 to 4 nitrogen atoms, 0 to 2 nonadjacent oxygen atoms, and/or 0 to 2 nonadjacent sulphur atoms, each of which is optionally mono- to tetrasubstituted by identical or different substituents selected from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio.

4. A $\Delta^1$-pyrroline of formula (I) according to claim 3 in which $R^4$ represents tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl, or isoquinolinyl, each of which is optionally mono- to tetrasubstituted by identical or different substituents selected from the group consisting of halogen, cyano, nitro, $C_1$–$C_6$-alkyl, $C_1$–$C_6$-halogenoalkyl, $C_2$–$C_6$-alkenyl, $C_2$–$C_6$-halogenoalkenyl, $C_1$–$C_6$-alkoxy, $C_1$–$C_6$-halogenoalkoxy, $C_1$–$C_6$-alkylthio, and $C_1$–$C_6$-halogenoalkylthio.

5. A $\Delta^1$-pyrroline of formula (I) according to claim 3 in which $R^7$ and $R^8$ independently of one another represent tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl, or isoquinolinyl, each of which is optionally mono- to tetrasubstituted by identical or different substituents selected from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio; or represent pyridinylmethyl, pyridinylethyl, pyrimidinylmethyl, pyrimidinylethyl, pyridazylmethyl, pyridazylethyl, pyrazinylmethyl or pyrazinylethyl, each of which is optionally mono- to tetrasubstituted by identical or different substituents selected from the group consisting of halogen, cyano, $C_1$–$C_6$alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

6. A $\Delta^1$-pyrroline of formula (I) according to claim 3 in which $R^9$ and $R^{10}$ independently of one another represent tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl, or isoquinolinyl, each of which is optionally mono- to tetrasubstituted by identical or different substituents selected from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio.

7. A $\Delta^1$-pyrroline of formula (I) according to claim 3 in which $R^{15}$ represents tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl, or isoquinolinyl, each of which is optionally mono- to tetrasubstituted by identical or different substituents selected from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, and $C_1$–$C_6$-halogenoalkylthio.

8. A $\Delta^1$-pyrroline of formula (I) according to claim 1 in which $R^1$ represents fluorine, chlorine, or methyl, $R^2$ represents hydrogen, fluorine, or chlorine, $R^3$ represents fluorine, chlorine, $C_1$–$C_4$-alkyl, $C_1$–$C_4$-alkoxy, or $C_1$–$C_4$-alkylthio; or represents $C_1$–$C_4$-halogenoalkyl, $C_1$–$C_4$-halogenoalkoxy, $C_1$–$C_4$-halogenoalkylthio, each having 1 to 9 fluorine, chlorine, and/or bromine atoms, m represents 0, 1, or 2, Q represents one of the groupings

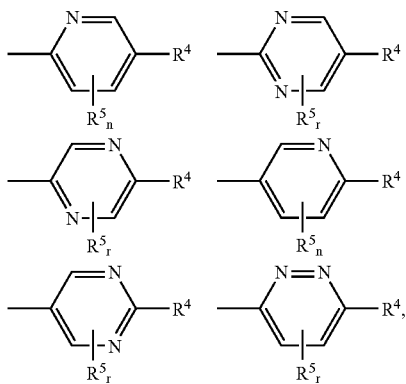

R[4] represents hydrogen, fluorine, chlorine, bromine, cyano, formyl, nitro, or tri-($C_1$–$C_4$-alkyl)silyl; represents $C_1$–$C_{16}$-alkyl, $C_2$–$C_{16}$-alkenyl, $C_1$–$C_{16}$-alkoxy, or $C_2$–$C_{16}$-alkenyloxy, each of which is optionally mono- or polysubstituted by identical or different substituents selected from the group consisting of fluorine, chlorine, bromine, cyano, and —NR[7]R[8]; represents —S(O)$_p$R[6], —NR[7]R[8], —COR[6], —CO$_2$R[6], —CONR[9]R[10], or —N(R[11])COR[12]; represents $C_3$–$C_{10}$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl, or isoquinolinyl, each of which is optionally mono- to trisubstituted by identical or different substituents selected from the group consisting of fluorine, chlorine, bromine, cyano, $C_1$–$C_4$-alkyl, $C_1$–$C_4$-halogenoalkyl, $C_2$–$C_6$-alkenyl, $C_2$–$C_6$-halogenoalkenyl, $C_1$–$C_4$-alkoxy, $C_1$–$C_4$-halogenoalkoxy, $C_1$–$C_4$-alkylthio, and $C_1$–$C_4$-halogenoalkylthio; represents —CH=NOH or formyl; or represents cyclopropyloxy, cyclobutyloxy, cyclopentyloxy, cyclohexyloxy, cyclopropylmethoxy, cyclobutylmethoxy, cyclopentylmethoxy or cyclohexylmethoxy, each of which is optionally mono- to trisubstituted by identical or different substituents selected from the group consisting of fluorine, chlorine, and methyl, R[5] represents fluorine, chlorine, or trimethylsilyl; represents $C_1$–$C_4$-alkyl, $C_2$–$C_6$-alkenyl, $C_1$–$C_4$-alkoxy, or $C_2$–$C_6$-alkenyloxy, each of which is optionally mono- to nonasubstituted by identical or different substituents selected from the group consisting of fluorine, chlorine and bromine, represents —S(O)$_p$R[6], —NR[7]R[8], —COR[6], —CO$_2$R[6], or —CONR[9]R[10], p represents 0, 1, or 2, n represents 0, 1, or 2, with the proviso that if n represents 2 then the substituents R[5] can be identical or different, r represents 0, 1, or 2, with the proviso that if r represents 2 then the substituents R[5] can be identical or different, R[6] represents $C_1$–$C_{10}$-alkyl that is optionally mono- or polysubstituted by identical or different substituents selected from the group consisting of fluorine, chlorine, bromine, NR[7]R[8], $C_1$–$C_4$-alkoxy, $C_1$–$C_4$-alkylthio, $C_1$–$C_4$-halogenoalkoxy, and $C_1$–$C_4$-halogenoalkylthio; or represents cyclopropyl, cyclopentyl, cyclohexyl, phenyl, or benzyl, each of which is optionally mono- to tetrasubstituted by identical or different substituents selected from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio, R[7] and R[8] independently of one another represent hydrogen, —SO$_2$R[6], —COR[6], or —CO$_2$R[6]; represent $C_1$–$C_{16}$-alkyl or $C_2$–$C_{16}$-alkenyl, each of which is optionally mono- or polysubstituted by identical or different substituents selected from the group consisting of fluorine, chlorine, bromine, $C_1$–$C_4$-alkylcarbonyl, $C_1$–$C_4$-alkylcarbonyloxy, $C_1$–$C_4$-alkylamino, di($C_1$–$C_4$-alkyl)amino, $C_1$–$C_4$-alkoxy, $C_1$–$C_4$-halogenoalkoxy, $C_1$–$C_4$-alkylthio, and $C_1$–$C_4$-halogenoalkylthio; represent $C_3$–$C_{10}$-cycloalkyl, $C_3$–$C_6$-cycloalkyl-C1–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl, or isoquinolinyl, each of which is optionally mono- to trisubstituted by identical or different substituents selected from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio; or represent pyridinylmethyl, pyridinylethyl, pyrimidinylmethyl, pyrimidinylethyl, pyridazylmethyl, pyridazylethyl, pyrazinylmethyl or pyrazinylethyl, each of which is optionally mono- to trisubstituted by identical or different substituents selected from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio, or R[7] and R[8] together represent $C_2$–$C_{10}$-alkenylene that is optionally mono- or polysubstituted by identical or different substituents selected from the group consisting of fluorine, chlorine, bromine, $C_1$–$C_4$-alkoxy, $C_1$–$C_4$-halogenoalkoxy, $C_1$–$C_4$-alkylthio, and $C_1$–$C_4$-halogenoalkylthio; together represent $C_3$–$C_{10}$-alkylene that is optionally mono- or polysubstituted in the alkylene moiety by identical or different substituents selected from the group consisting of fluorine, chlorine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio, where the alkylene chain is optionally interrupted by —O—, —S—, or —NR[15]—; together represent $C_3$–$C_{10}$-alkylene that is mono- to trisubstituted by identical or different substituents selected from n-propoxycarbonyl, isopropoxycarbonyl, ethoxycarbonyl, methoxycarbonyl, oxypropyleneoxy, oxyethyleneoxy, and oxymethyleneoxy; or together represent $C_3$–$C_6$-alkylene, where the alkylene chain is interrupted either by C=O or by C=NO—($C_1$–$C_4$-alkyl), R[9] and R[10] independently of one another represent hydrogen or —SO$_2$R[6]; represent $C_1$–$C_4$-alkyl or $C_2$–$C_6$-alkenyl, each of which is optionally mono- to nonasubstituted by identical or different substituents selected from the group consisting of fluorine, chlorine, bromine, $C_1$–$C_4$-alkylamino, di($C_1$–$C_4$-alkyl)-amino, $C_1$–$C_4$-alkoxy, $C_1$–$C_4$-halogenoalkoxy, $C_1$–$C_4$-alkylthio, and $C_1$–$C_4$-halogenoalkylthio; or represent $C_3$–$C_6$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl, or isoquinolinyl, each of which is optionally mono- to trisubstituted by identical or different substituents selected from the group consisting of fluorine, chlorine, bromine, $C_1$–$C_4$-alkyl, cyano, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio, or $R^9$ and $R^{10}$ together represent $C_4$–$C_5$-alkylene, —(CH$_2$)$_2$—O—(CH$_2$)$_2$—, —(CH$_2$)$_2$—S—(CH$_2$)$_2$—, or —(CH$_2$)$_2$—N($R^{15}$)—(CH$_2$)$_2$—, each of which is optionally mono- to tetrasubstituted in the alkylene moiety by identical or different substituents selected from the group consisting of fluorine, chlorine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio, $R^{11}$ and $R^{12}$ independently of one another represent hydrogen; represent $C_1$–$C_6$-alkyl that is optionally mono- to nonasubstituted by identical or different substituents selected from the group consisting of fluorine, chlorine, bromine, $C_1$–$C_4$-alkoxy, and $C_1$–$C_4$-alkylthio; or represent $C_3$–$C_6$-cycloalkyl, $C_3$–$C_6$-cycloalkyl-$C_1$–$C_4$-alkyl, phenyl, benzyl, or phenylethyl, each of which is optionally mono- to tetrasubstituted by identical or different substituents selected from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio, or $R^{11}$ and $R^{12}$ together represent $C_3$–$C_8$-alkylene or $C_3$–$C_8$-alkenylene, each of which is optionally mono- to tetrasubstituted by identical or different substituents selected from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio, and $R^{15}$ represents hydrogen or —SO$_2$$R^6$; represents —COR$^6$ or —CO$_2$$R^6$; represents $C_1$–$C_{16}$-alkyl or $C_2$–$C_{16}$-alkenyl, each of which is optionally mono- or polysubstituted by identical or different substituents selected from the group consisting of fluorine, chlorine, bromine, cyano, methylamino, ethylamino, di($C_1$–$C_6$-alkyl)amino, $C_1$–$C_4$-alkoxy, $C_1$–$C_4$-halogenoalkoxy, $C_1$–$C_4$-alkylthio, and $C_1$–$C_4$-halogenoalkylthio; or represents $C_3$–$C_{10}$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl, or isoquinolinyl, each of which is optionally mono- to trisubstituted by identical or different substituents selected from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio.

9. A $\Delta^1$-pyrroline of formula (I) according to claim 1 in which $R^1$ represents fluorine or chlorine, $R^2$ represents hydrogen or fluorine, $R^3$ represents fluorine, chlorine, methyl, ethyl, n-propyl, isopropyl, n-butyl, isobutyl, sec-butyl, tert-butyl, trifluoromethyl, trifluoroethyl, methoxy, ethoxy, n-propoxy, isopropoxy, n-butoxy, isobutoxy, sec-butoxy, tert-butoxy, trifluoromethoxy, trifluoroethoxy, methylthio, ethylthio, n-propylthio, isopropylthio, n-butylthio, isobutylthio, sec-butylthio, tert-butylthio, trifluoromethylthio or trifluoroethylthio, m represents 0 or 1, Q represents one of the groupings

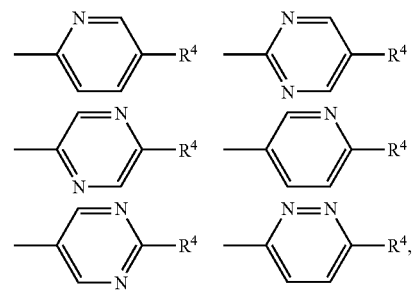

$R^4$ represents hydrogen, fluorine, chlorine, bromine, cyano, or formyl; represents $C_1$–$C_{16}$-alkyl, $C_2$–$C_{16}$-alkenyl, $C_1$–$C_{16}$-alkoxy, or $C_2$–$C_{16}$-alkenyloxy, each of which is optionally mono- or polysubstituted by identical or different substituents selected from the group consisting of fluorine, chlorine, bromine, cyano, and —NR$^7$R$^8$; represents —S(O)$_p$R$^6$, —NR$^7$R$^8$, —COR$^6$, —CO$_2$R$^6$, —CONR$^9$R$^{10}$, or —N(R$^{11}$)COR$^{12}$; represents cyclopropyl, cyclopentyl, cyclohexyl, cyclopropylmethyl, cyclopentylmethyl, cyclohexylmethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl, or isoquinolinyl, each of which is optionally mono- to trisubstituted by identical or different substituents selected from the group consisting of fluorine, chlorine, bromine, cyano, methyl, ethyl, n-propyl, isopropyl, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, vinyl, allyl, 1-propenyl, butenyl, —CF═CHF, —CF═CH$_2$, —CF═CCl$_2$, —CH═CF$_2$, —CF$_2$CF═CF$_2$, —CH═CFH, —CH$_2$CF═CF$_2$, —CF═CF$_2$, —CF$_2$CH═CF$_2$, methoxy, ethoxy, n-propoxy, isopropoxy, n-butoxy, isobutoxy, sec-butoxy, tert-butoxy, trifluoromethoxy, difluoromethoxy, chlorodifluoromethoxy, trifluoroethoxy, methylthio, ethylthio, n-propylthio, isopropylthio, n-butylthio, isobutylthio, sec-butylthio, tert-butylthio, trifluoromethylthio, difluoromethylthio, chlorodifluoromethylthio, and trifluoroethylthio; represents —CH═NOH or formyl; or represents cyclopropyloxy, cyclobutyloxy, cyclopentyloxy, cyclohexyloxy, cyclopropylmethoxy, cyclobutylmethoxy, cyclopentylmethoxy, or cyclohexylmethoxy, p represents 0, 1, or 2, $R^6$ represents methyl, ethyl, n-propyl, isopropyl, n-butyl, isobutyl, sec-butyl, tert-butyl, pentyl, hexyl, —$CF_3$, —$CHF_2$, —$CCl_3$, —$CCl_2F$, dimethylaminomethyl, dimethylaminoethyl, diethylaminomethyl, diethylaminoethyl, cyclopropyl, cyclopentyl, cyclohexyl, phenyl, benzyl, methoxymethyl, trifluoromethoxymethyl, methylthiomethyl, or trifluoromethylthiomethyl, $R^7$ and $R^8$ independently of one another represent hydrogen, —$SO_2R^6$, —$COR^6$, or —$CO_2R^6$; represent $C_1$–$C_{16}$-alkyl or $C_2$–$C_{16}$-alkenyl, each of which is optionally mono- or polysubstituted by identical or different substituents selected from the group consisting of fluorine, chlorine, bromine, $C_1$–$C_4$-alkylcarbonyl, $C_1$–$C_4$-alkylcarbonyloxy, $C_1$–$C_4$-alkylamino, di($C_1$–$C_4$-alkyl)amino, $C_1$–$C_4$-alkoxy, $C_1$–$C_4$-halogenoalkoxy, $C_1$–$C_4$-alkylthio, or $C_1$–$C_4$-halogenoalkylthio; represent $C_3$–$C_8$-cycloalkyl, cyclopropylmethyl, cyclopentylmethyl, cyclohexylmethyl, cyclopropylethyl, cyclopentylethyl, cyclohexylethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl, or isoquinolinyl, each of which is optionally mono- to trisubstituted by identical or different substituents selected from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio; or represent pyridinylmethyl, pyrimidinylmethyl, pyridazylmethyl or pyrazinylmethyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, and $C_1$–$C_4$-halogenoalkylthio, or $R^7$ and $R^8$ together represent $C_2$–$C_8$-alkenylene that is optionally mono- or polysubstituted by identical or different substituents selected from the group consisting of fluorine, chlorine, bromine, $C_1$–$C_4$-alkoxy, $C_1$–$C_4$-halogenoalkoxy, $C_1$–$C_4$-alkylthio, and $C_1$–$C_4$-halogenoalkylthio; together represent $C_3$–$C_8$-alkylene that is optionally mono- or polysubstituted in the alkylene moiety by identical or different substituents selected from the group consisting of fluorine, chlorine, cyano, methyl, ethyl, n-propyl, isopropyl, n-butyl, isobutyl, sec-butyl, tert-butyl, $C_1$–$C_4$-halogenoalkyl, methoxy, ethoxy, n-propoxy, isopropoxy, n-butoxy, isobutoxy, sec-butoxy, tert-butoxy, $C_1$–$C_4$-halogenoalkoxy, methylthio, ethylthio, n-propylthio, isopropylthio, n-butylthio, isobutylthio, sec-butylthio, tert-butylthio, and $C_1$–$C_4$-halogenoalkylthio, where the alkylene chain is optionally interrupted by —O—, —S—, or —$NR^{15}$—; together represent $C_3$–$C_8$-alkylene that is mono- or disubstituted by identical or different substituents selected from the group consisting of ethoxycarbonyl, methoxycarbonyl, and oxyethyleneoxy; or together represent —$CH_2$—$CH_2$—C(=O)—$CH_2$—$CH_2$—, —$CH_2$—$CH_2$—C(=NO-Me)—$CH_2$—$CH_2$—, —$CH_2$—$CH_2$—C(=NO-Et)—$CH_2$—$CH_2$—, or —$CH_2$—$CH_2$—C(=NO-iPr)—$CH_2$—$CH_2$—, $R^9$ and $R^{10}$ independently of one another represent hydrogen, —$SO_2OF_3$, methyl, ethyl, n-propyl, isopropyl, n-butyl, isobutyl, sec-butyl, tert-butyl, pentyl, hexyl, —$CF_3$, —$CH_2CF_3$, —$(CF_2)_3CF_3$, cyclopropyl, cyclopentyl, cyclohexyl, or methoxymethyl, methoxyethyl; or represent phenyl or benzyl, each of which is optionally substituted by fluorine, chlorine, bromine, methyl, trifluoromethyl, methoxy, or trifluoromethoxy, or $R^9$ and $R^{10}$ together represent —$(CH_2)_4$—, —$(CH_2)_5$—, —$(CH_2)_6$—, —$CH_2$—$CH(CH_3)$—$CH_2$—$CH(CH_3)$—$CH_2$—, —$(CH_2)_2$—O—$(CH_2)_2$—, —$(CH_2)_2$—S—$(CH_2)_2$—, or —$(CH_2)_2$—$N(R^{15})$—$(CH_2)_2$—, $R^{11}$ and $R^{12}$ independently of one another represent methyl, ethyl, n-propyl, isopropyl, n-butyl, isobutyl, sec-butyl, tert-butyl, n-hexyl, trifluoromethyl, trifluoroethyl, cyclopropyl, cyclopentyl, or cyclohexyl; or represent phenyl or benzyl, each of which is optionally substituted by fluorine, chlorine, bromine, methyl, trifluoromethyl, methoxy, or trifluoromethoxy, or $R^{11}$ and $R^{12}$ together represent —$(CH_2)_3$—, —$(CH_2)_4$—, —$(CH_2)_5$— or —$(CH_2)_6$—, each of which is optionally substituted by fluorine, chlorine, bromine, methyl, ethyl, methoxy, ethoxy, methylthio, ethylthio, trifluoromethyl, trifluoromethoxy, or trifluoromethylthio, and $R^{15}$ represents hydrogen or —$SO_2R^6$; represents —$COR^6$ or —$SO_2R^6$; represents $C_1$–$C_{16}$-alkyl, or $C_2$–$C_{16}$-alkenyl, each of which is optionally mono- or polysubstituted by identical or different substituents selected from the group consisting of fluorine, chlorine, bromine, cyano, methylamino, ethylamino, di($C_1$–$C_6$-alkyl)amino, $C_1$–$C_4$-alkoxy, $C_1$–$C_4$-halogenoalkoxy, $C_1$–$C_4$-alkylthio, and $C_1$–$C_4$-halogenoalkylthio; or represents $C_3$–$C_8$-cycloalkyl, cyclopropylmethyl, cyclopentylmethyl, cyclohexylmethyl, cyclopropylethyl, cyclopentylethyl, cyclohexylethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents selected from the group consisting of fluorine, chlorine, bromine, cyano, methyl, ethyl, n-propyl, isopropyl, n-butyl, isobutyl, sec-butyl, tert-butyl, $C_1$–$C_4$-halogenoalkyl, methoxy, ethoxy, n-propoxy, isopropoxy, n-butoxy, isobutoxy, sec-butoxy, tert-butoxy, $C_1$–$C_4$-halogenoalkoxy, methylthio, ethylthio, n-propylthio, isopropylthio, n-butylthio, isobutylthio, sec-butylthio, tert-butylthio, and $C_1$–$C_4$-halogenoalkylthio.

10. A $\Delta^1$-pyrroline of formula (I) according to claim 1 in which $R^1$ and $R^2$ each represent fluorine.

11. A $\Delta^1$-pyrroline of formula (I) according to claim 1 in which Q represents

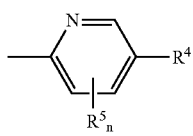

in which $R^4$, $R^5$, and n have the meanings given in claim 1.

12. A $\Delta^1$-pyrroline of formula (I) according to claim 1 in which Q represents

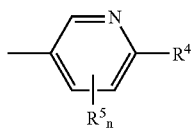

in which $R^4$, $R^5$, and n have the meanings given in claim 1.

13. A $\Delta^1$-pyrroline of formula (I) according to claim 1 in which Q represents

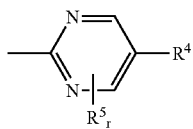

in which $R^4$, $R^5$, and r have the meanings given in claim 1.

14. A $\Delta^1$-pyrroline of formula (I) according to claim 1 in which Q represents

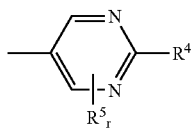

in which $R^4$, $R^5$, and r have the meanings given in claim 1.

15. A $\Delta^1$-pyrroline of formula (I) according to claim 1 in which Q represents

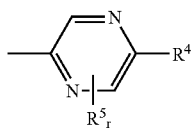

in which $R^4$, $R^5$, and r have the meanings given in claim 1.

16. A $\Delta^1$-pyrroline of formula (I) according to claim 1 in which Q represents

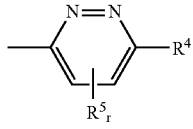

in which $R^4$, $R^5$, and r have the meanings given in claim 1.

17. A compound of formula (I-a) to (I-f)

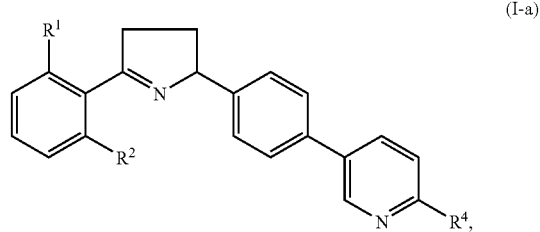

(I-a)

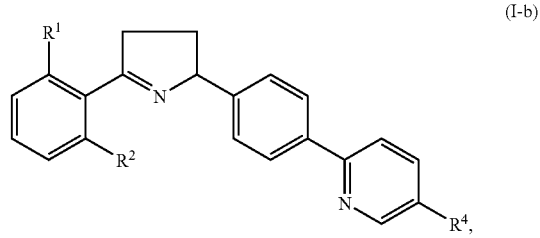

(I-b)

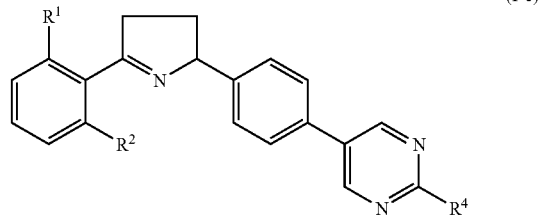

(I-c)

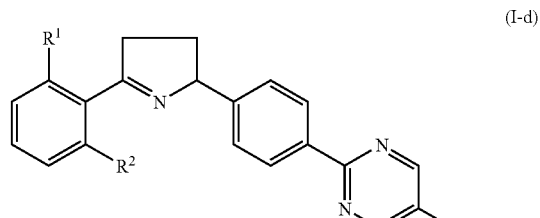

(I-d)

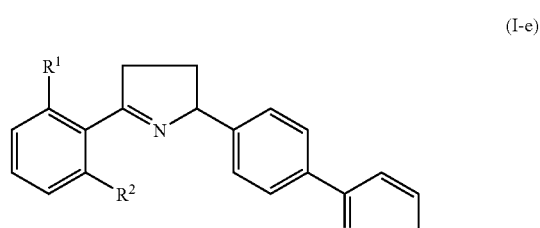

(I-e), or

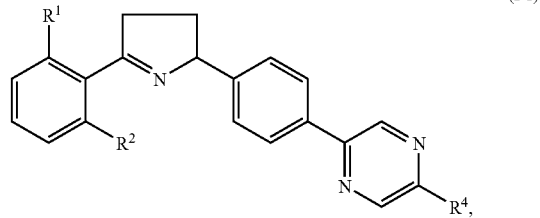

(I-f)

in which
$R^1$ represents fluorine or chlorine,
$R^2$ represents hydrogen or fluorine, and
$R^4$ has the meanings given in claim 1.

18. An (R)-configured compound of formula (I-g) to (I-l)

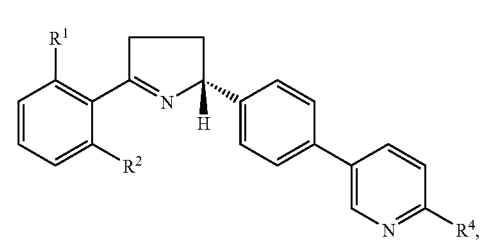 (I-g)

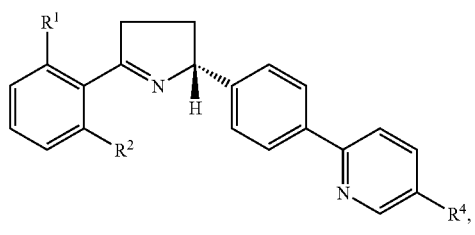 (I-h)

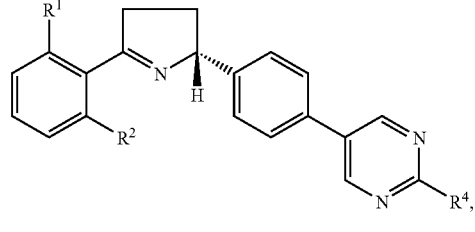 (I-i)

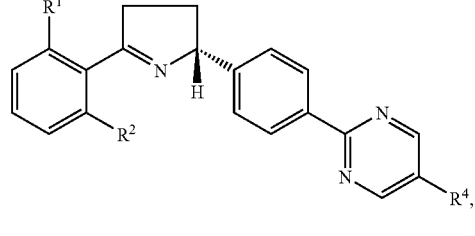 (I-j)

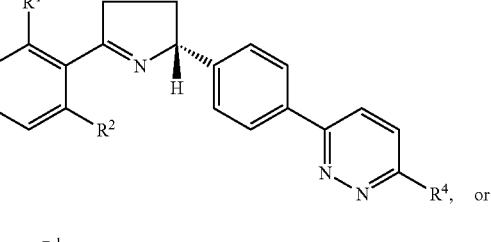 (I-k)

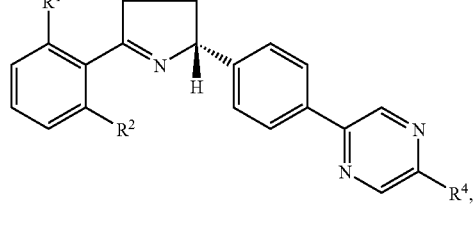 (I-l)

in which
$R^1$ represents fluorine or chlorine,
$R^2$ represents hydrogen or fluorine, and
$R^4$ has the meanings given in claim 1.

19. A process for preparing a compound of formula (I) according to claim 1 comprising (A) reacting a $\Delta^1$-pyrroline of formula (II)

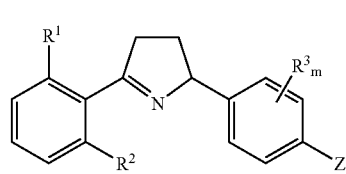 (II)

in which
$R^1$, $R^2$, $R^3$, and m have the meanings given in claim 1, and
Z represents chlorine, bromine, iodine, —OSO$_2$CF$_3$, or —OSO$_2$(CF$_2$)$_3$CF$_3$,
in a tandem reaction with a heterocycle of formula (III)

Q—X  (III)

in which
Q has the meaning given in claim 1, and
X represents chlorine, bromine, iodine, —OSO$_2$CF$_3$, or —OSO$_2$(CF$_2$)$_3$CF$_3$,
in the presence of a catalyst, in the presence of a diboronic acid ester, and optionally in the presence of an acid binder and optionally in the presence of a diluent, or (B) reacting a $\Delta^1$-pyrroline of formula (IV)

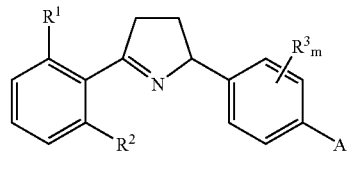 (IV)

in which
$R^1$, $R^2$, $R^3$, and m have the meanings given in claim 1, and
A represents —B(OH)$_2$, (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl, or 1,3,2-benzodioxaborol-2-yl,
with a heterocycle of formula (III)

Q—X  (III)

in which Q and X have the meanings given in claim 1, in the presence of a catalyst, optionally in the presence of an acid binder, and optionally in the presence of a diluent, or (C) reacting a $\Delta^1$-pyrroline of formula (II)

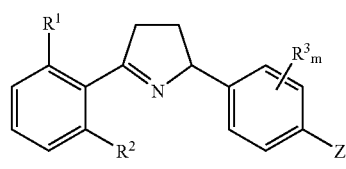 (II)

in which $R^1$, $R^2$, $R^3$, m, and Z have the meanings given in claim 1, with a boronic acid derivative of formula (V)

Q—A  (V)

in which Q and A have the meanings given in claim 1, in the presence of a catalyst, optionally in the presence of an acid binder, and optionally in the presence of a diluent, or (D) reacting a $\Delta^1$-pyrroline of formula (II-a)

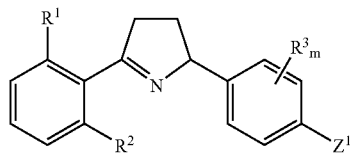

(II-a)

in which
$R^1$, $R^2$, $R^3$, and m have the meanings given in claim 1, and
$Z^1$ represents bromine or iodine,
with an organometallic compound of formula (VI)

Q—M  (VI)

in which
Q has the meanings given in claim 1, and
M represents $ZnCl$, $Sn(Me)_3$, or $Sn(n-Bu)_3$,
in the presence of a catalyst, optionally in the presence of an acid binder, and optionally in the presence of a diluent.

20. A $\Delta^1$-pyrroline of formula (IV)

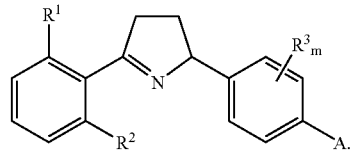

(IV)

in which
$R^1$ represents halogen or methyl,
$R^2$ represents hydrogen or halogen,
$R^3$ represents halogen or optionally substituted alkyl, alkoxy, or alkylthio,
m represents 0, 1, 2, 3, or 4, and
A represents —$B(OH)_2$, (4,4,5,5-tetramethyl-1,3,2-dioxaborolan)-2-yl, (5,5-di-methyl-1,3,2-dioxaborinan)-2-yl, (4,4,6-trimethyl-1,3,2-dioxaborinan)-2-yl, or 1,3,2-benzodioxaborol-2-yl.

21. A pesticide comprising at least one compound of formula (I) according to claim 1 and one or more extenders and/or surfactants.

22. Method for controlling pests comprising allowing a compound of formula (I) according to claim 1 to act on pests and/or their habitat.

23. A process for preparing a pesticide comprising mixing a compound of formula (I) according to claim 1 with one or more extenders and/or surfactants.

* * * * *